(12) United States Patent
Khanna et al.

(10) Patent No.: US 9,901,632 B2
(45) Date of Patent: Feb. 27, 2018

(54) HUMAN HERPESVIRUS IMMUNOTHERAPY

(71) Applicant: The Council of the Queensland Institute of Medical Research, Herston, Queensland (AU)

(72) Inventors: Rajiv Khanna, Herston (AU); Dasari Vijayendra, Herston (AU)

(73) Assignee: The Council of the Queensland Institute of Medical Research, Herston (AU)

(*) Notice: Subject to any disclaimer, the term of this patent is extended or adjusted under 35 U.S.C. 154(b) by 0 days.

(21) Appl. No.: 14/436,239

(22) PCT Filed: Oct. 21, 2013

(86) PCT No.: PCT/AU2013/001216
§ 371 (c)(1),
(2) Date: Apr. 16, 2015

(87) PCT Pub. No.: WO2014/059489
PCT Pub. Date: Apr. 24, 2014

(65) Prior Publication Data
US 2015/0273051 A1    Oct. 1, 2015

(30) Foreign Application Priority Data
Oct. 19, 2012   (AU) .............................. 2012904604

(51) Int. Cl.
| A61K 39/245 | (2006.01) |
| C12N 7/00 | (2006.01) |
| C07K 14/005 | (2006.01) |
| C12N 5/0783 | (2010.01) |
| A61K 39/00 | (2006.01) |

(52) U.S. Cl.
CPC .......... *A61K 39/245* (2013.01); *C07K 14/005* (2013.01); *C12N 5/0638* (2013.01); *C12N 7/00* (2013.01); *A61K 2039/572* (2013.01); *A61K 2039/6031* (2013.01); *A61K 2039/70* (2013.01); *C07K 2319/00* (2013.01); *C07K 2319/21* (2013.01); *C07K 2319/40* (2013.01); *C12N 2501/998* (2013.01); *C12N 2710/16122* (2013.01); *C12N 2710/16134* (2013.01); *C12N 2710/16222* (2013.01); *C12N 2710/16234* (2013.01)

(58) Field of Classification Search
None
See application file for complete search history.

(56) References Cited

U.S. PATENT DOCUMENTS

| 7,524,503 B2 * | 4/2009 | Khanna | C07K 14/005 424/186.1 |
| 7,976,845 B2 * | 7/2011 | Khanna | A61K 38/162 424/192.1 |
| 2005/0054107 A1 * | 3/2005 | Chulay | C07K 14/005 435/456 |
| 2008/0107620 A1 * | 5/2008 | Khanna | A61K 38/162 424/85.1 |
| 2010/0183647 A1 * | 7/2010 | Khanna | C07K 14/005 424/186.1 |

FOREIGN PATENT DOCUMENTS

| WO | WO-03/000720 A1 | 1/2003 |
| WO | WO 2004/007556 A1 | 1/2004 |
| WO | WO-2004/041849 A1 | 5/2004 |
| WO | WO 2005/007689 A1 | 1/2005 |
| WO | WO-2005/007689 A1 | 1/2005 |
| WO | WO 2006/056027 A1 | 6/2006 |
| WO | WO-2006/056027 A1 | 6/2006 |
| WO | WO 2010/014567 A2 | 2/2010 |
| WO | WO-2010/014567 A2 | 2/2010 |

OTHER PUBLICATIONS

Bowie JU, Reidhaar-Olson JF, Lim WA, Sauer RT. Deciphering the message in protein sequences: tolerance to amino acid substitutions. Science. Mar. 16, 1990;247(4948):1306-10.*
Ackerman, A.L. et al. (2006) "*A Role for the Endoplasmic Reticulum Protein Retrotranslocation Machinery During Crosspresentation by Dendritic Cells*," Immunity 25(4):607-617.
Anderson, R.J. et al. (2007) "*Plasmid DNA and Viral Vector-Based Vaccines for the Treatment of Cancer*," Vaccine 25 Suppl. 2:B24-B34.
Arvin, A.M. et al. (2004) "*Vaccine Development to Prevent Cytomegalovirus Disease: Report from the National Vaccine Advisory Committee*," Clin. Infect. Dis. 39(2):233-239.
Bazhan, S.I. et al. (2010) "*Rational Design Based Synthetic Polyepitope DNA Vaccine for Eliciting HIV-Specific CD8+ T Cell Responses*," Mol. Immunol 47(7-8):1507-1515.
Bernstein, D.I. et al. (2009) "*Randomized, Double-Blind, Phase I Trial of an Alphavirus Replicon Vaccine for Cytomegalovirus in CMV Seronegative Adult Volunteers*," Vaccine 28(2):484-493.
Betts, M.R. et al. (2006) "*Antigen-Specific T-Cell-Mediated Immunity After HIV-1 Infection: Implications for Vaccine Control of HIV Development*," Expert Rev. Vaccines 5(4):505-516.
Brytting, M. et al. (1992) "*Variations in the Cytomegalovirus Major Immediate-Early Gene Found by Direct Genomic Sequencing*," J. Clin. Microbiol. 30(4):955-960.

(Continued)

*Primary Examiner* — Benjamin P Blumel
(74) *Attorney, Agent, or Firm* — Foley Hoag LLP

(57) ABSTRACT

An isolated protein comprises respective amino acid sequences of each of a plurality of CTL epitopes from two or more different herpesvirus antigens and further comprises an intervening amino acid or amino acid sequence between at least two of said CTL epitopes comprising proteasome liberation amino acids or amino acid sequences and, optionally, Transporter Associated with Antigen Processing recognition motifs. The isolated protein is capable of rapidly expanding human cytotoxic T lymphocytes (CTL) in vitro and eliciting a CTL immune response in vivo upon administration to an animal as an exogenous protein. Typically, the isolated protein comprises no more than twenty (20) CTL epitopes derived from cytomegalovirus and/or Epstein-Barr virus antigens.

22 Claims, 19 Drawing Sheets

(56) References Cited

OTHER PUBLICATIONS

Darrah, P.A. et al. (2007) "*Multifunctional TH1 Cells Define a Correlate of Vaccine-Mediated Protection Against Leishmania Major*," Nat. Med. 13(7):843-850.
Dasari, V. et al. (2011) "*Recombinant Glycoprotein B Vaccine Formulation with Toll-Like Receptor 9 Agonist and Immune-Stimulating Complex Induces Specific Immunity Against Multiple Strains of Cytomegalovirus*," J. Gen. Virol. 92:1021-1031.
Ding, W.X. et al. (2007) "*Linking of Autophagy to Ubiquitin-Proteasome System is Important for the Regulation of Endoplasmic Reticulum Stress and Cell Viability*," Am. J. Pathol. 171(2):513-524.
Drulak, M.W. et al. (2000) "*Vaccination of Seropositive Subjects with CHIRON CMV gB Subunit Vaccine Combined with MF59 Adjuvant for Production of CMV Immune Globulin*," Viral Immunol. 13:49-56.
Elkington, R. et al. (2003) "*Ex Vivo Profiling of CD8+—T-Cell Response to Human Cytomegalovirus Reveals Broad and Multispecific Reactivities in Healthy Virus Carriers*," J. Virol. 77(9):5226-5240.
Elkington, R. et al. (2004) "*Cross-Reactive Recognition of Human and Primate Cytomegalovirus Sequences by Human CD4 Cytotoxic T Lymphocytes Specific for Glycoprotein B and H*," Eur. J. Immunol. 34(11):3216-3266.
Frankenberg, N. et al. (2002) "*Identification of a Conserved HLA-A2-Restricted Decapeptide from the IE1 Protein (pUL123) of Human Cytomegalovirus*," Virology 295(2):208-216.
Guermonprez, P. et al. (2003) "*ER-Phagosome Fusion Defines an MHC Class I Cross-Presentation Compartment in Dendritic Cells*," Nature 425(6956):397-402.
Houde, M. et al. (2003) "*Phagosomes are Competent Organelles for Antigen Cross-Presentation*," Nature 425(6956):402-406.
Huang, A.Y. et al. (1996) "*In Vivo Cross-Priming of MHC Class I-Restricted Antigens Requires the Tap Transporter*," Immunity 4(4):349-355.
International Search Report, PCT/AU2013/001216 dated (2013), 5 Pages.
Ishioka, G.Y. et al. (1999) "*Utilization of MHC Class I Transgenic Mice for Development of Minigene DNA Vaccines Encoding Multiple HLA-Restricted CTL Epitopes*," J. Immunol 162(7):3915-3925.
Jacobson, M.A. et al. (2006) "*Antigen-Specific T Cell Response Induced by Towne Cytomegalovirus (CMV) Vaccine in CMV-Seronegative Vaccine Recipients*," J. Clin. Virol. 35(3):332-337.
Khan, N. et al. (2005) "*Identification of Cytomegalovirus-Specific Cytotoxic T Lymphocytes in Vitro is Greatly Enhanced by the Use of Recombinant Virus Lacking the US2 to US11 Region or Modified Vaccinia Virus Ankara Expressing Individual Viral Genes*," J. Virol. 79(5):2869-2879.
Kuttler, C. et al. (2000) "*An Algorithm for the Prediction of Proteasomal Cleavages*," J. Mol. Biol. 298(3):417-429.
Liu, M.A. (2010) "*Immunologic Basis of Vaccine Vectors*," Immunity 33(4):504-515.
Livingston, B.D. et al. (2001) "*Optimization of Epitope Processing Enhances Immunogenicity of Multiepitope DNA Vaccines*," Vaccine 19(32):4652-4660.
Manley, T.J. et al. (2004) "*Immune Evasion Proteins of Human Cytomegalovirus Do Not Prevent a Diverse CD8+ Cytotoxic T-Cell Response in Natural Infection*," Blood 104(4):1075-1082.
Millington, K.A. et al. (2007) "*Dynamic Relationship Between IFN-Gamma and IL-2 Profile of Mycobacterium Tuberculosis-Specific T Cells and Antigen Load*," J. Immunol 178(8):5217-5226.
Mizushima, N. et al. (1998) "*A New Protein Conjugation System in Human. The Counterpart of the Yeast Apg12p Conjugation System Essential for Autophagy*," J. Biol. Chem. 273(51):33889-33892.
Mizushima, N. et al. (1998) "*A Protein Conjugation System Essential for Autophagy*," Nature 395(6700):395-398.
Mutter, W. et al. (1988) "*Failure in Generating Hemopoietic Stem Cells is the Primary Cause of Death from Cytomegalovirus Disease in the Immunocompromised Host*," J. Exp. Med 167(5):1645-1658.

Nebbia, G. et al. (2008) "*Polyfunctional Cytomegalovirus-Specific CD4+ and pp65 CD8+ T Cells Protect Against High-Level Replication After Liver Transplantation*," Am. J. Transplant 8(12):2590-2599.
Palella, F.J. et al. (1998) "*Declining Morbidity and Mortality Among Patients with Advanced Human Immunodeficiency Virus Infections. HIV Outpatient Study Investigators*," N. Engl. J. Med. 338(13):853-860.
Quinnan, G.V. et al. (1982) "*Cytotoxic T Cells in Cytomegalovirus Infections: HLA-Restricted T-Lymphocyte and Non-T-Lymphocyte Cytotoxic Response Correlate with Recovery from Cytomegalovirus Infection in Bone-Marrow-Transplant Recipients*," N. Engl. J. Med. 307:7-13.
Reddehase, M.J. et al. (1985) "*Interstitial Murine Cytomegalovirus Pneumonia After Irradiation: Characterization of Cells that Limit Viral Replication During Established Infection of the Lungs*," J. Virol. 55(2):264-273.
Retiere, C. et al. (1998) "*A Polymorphism in the Major Immediate-Early Gene Delineates Groups Among Cytomegalovirus Clinical Isolates*," Virus. Res. 57:43-51.
Riddell, S.R. et al. (1992) "*Restoration of Viral Immunity in Immunodeficient Humans by the Adoptive Transfer of T Cell Clones*," Science 257(5067):238-241.
Rock, K.L. (2006) "*Exiting the Outside World for Cross-Presentation*," Immunity 25(4):523-525.
Rock, K.L. et al. (2005) "*Cross-Presentation: Underlying Mechanisms and Role in Immune Surveillance*," Immunol. Rev. 207:166-183.
Rook, A.H. et al. (1984) "*Importance of Cytotoxic Lymphocytes During Cytomegalovirus Infection in Renal Transplant Recipients*," Am. J. Med. 76(3):385-392.
Salmon-Ceron, D. et al. (2000) "*Plasma Cytomegalovirus DNA, pp65 Antigenaemia and a Low CD4 Cell Count Remain Risk Factors for Cytomegalovirus Disease in Patients Receiving Highly Active Antiretroviral Therapy*," AIDS 14(8):1041-1049.
Seder, R.A. et al. (2008) "*T-Cell Quality in Memory and Protection: Implications for Vaccine Design*," Nat. Rev. Immunol 8(4):247-258.
Shen, L. et al. (2004) "*Important Role of Cathepsin S in Generating Peptides for TAP-Independent MHC Class I Crosspresentation in Vivo*," Immunity 21(2):155-165.
Soderberg-Naucler, C. (2006) "*Does Cytomegalovirus Play a Causative Role in the Development of Various Inflammatory Diseases and Cancer?*" J. Intern. Med. 259(3):219-246.
Solache, A. et al. (1999) "*Identification of Three HLA-A*0201-Restricted Cytotoxic T Cell Epitopes in the Cytomegalovirus Protein pp65 That are Conserved Between Eight Strains of the Virus*," J. Immunol. 163(10):5512-5518.
Sylwester, A.W. et al. (2005) "*Broadly Targeting Human Cytomegalovirus-Specific CD4+ and CD8+ T Cells Dominate the Memory Compartments of Exposed Subjects*," J. Exp. Med. 202(5):673-685.
Uebel, S. et al. (1999) "*Peptide Libraries in Cellular Immune Recognition*," Curr. Top. Microbiol. Immunol 243:1-21.
Walter, E.A. et al. (1995) "*Reconstitution of Cellular Immunity Against Cytomegalovirus in Recipients of Allogeneic Bone Marrow by Transfer of T-Cell Clones from the Donor*," N. Engl. J. Med. 333(16):1038-1044.
Webb, J.L. et al. (2003) "*Alpha-Synuclein is Degraded by Both Autophagy and the Proteasome*," J. Biol. Chem. 278(27):25009-25013.
Wloch, M.K. et al. (2008) "*Safety and Immunogenicity of a Bivalent Cytomegalovirus DNA Vaccine in Healthy Adult Subjects*," J. Infect. Dis. 197(12):1634-1642.
Written Opinion, PCT/AU2013/001216 dated (2013), 6 Pages.
Zhong, J. et al. (2008) "*Induction of Pluripotent Protective Immunity Following Immunisation with a Chimeric Vaccine Against Human Cytomegalovirus*," PLoS One 3(9):e3256.
Zhong, J. et al. (2009) "*Ad-gBCMVpoly: A Novel Chimeric Vaccine Strategy for Human Cytomegalovirus-Associated Diseases*," J. Clin. Virol. 46(Suppl. 4):S68-S72.
Bazhan, et al., "Rational design based synthetic polyepitope DNA vaccine for eliciting HIV-specific CD8+ T cell responses," Mol Immunol, 47(7-8): 1507-1515 (2010).

(56) References Cited

OTHER PUBLICATIONS

Extended European Search Report for EP Application No. 13847496.0 dated Oct. 28, 2016.

Nielsen, et al., "An in vitro-transcribed-mRNA polyepitope construct encoding 32 distinct HLA class I-restricted epitopes from CMV, EBV, and Influenza for use as a functional control in human immune monitoring studies," J Immunol Methods, 360(1-2): 149-156 (2010).

Rist, et al., "Ex vivo expansion of human cytomegalovirus-specific cytotoxic T cells by recombinant polyepitope: implications for HCMV immunotherapy," Eur J Immunol, 35(3): 996-1007 (2005).

Smith, et al., "Functional reversion of antigen-specific CD8+ T cells from patients with Hodgkin Lymphoma following in Vitro stimulation with recombinant polyepitope," J Immunol, 177(7): 4897-4906 (2006).

Zhao, et al., "The development of Chinese specific human cytomegalovirus polyepitope recombinant vaccine," Antiviral Res, 93(2): 260-269 (2011).

\* cited by examiner

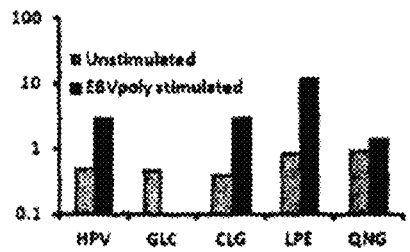
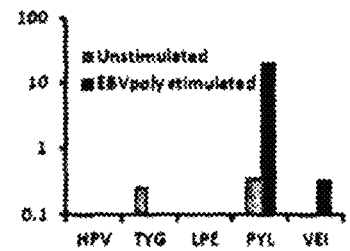
Fig. 14a　　　Fig. 14b
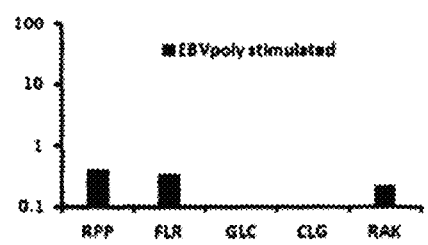
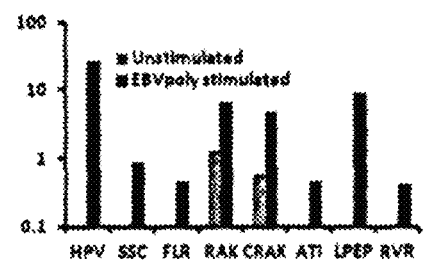
Fig. 14c　　　Fig. 14d
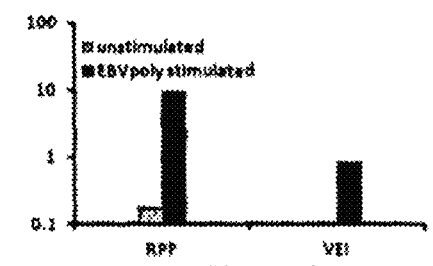
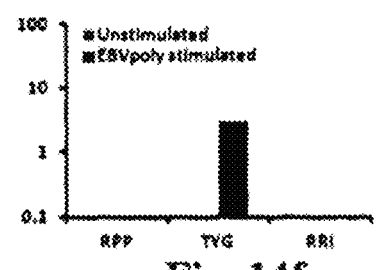
Fig. 14e　　　Fig. 14f
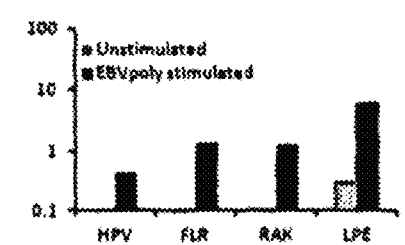
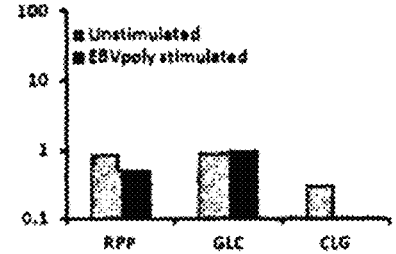
Fig. 14g　　　Fig. 14h

A  CMVpoly with proteasome and TAP linkers with his tag

```
  1  M  F  P  T  K  D  V  A  L  A  D  R  I  W  G  P  I  S  H  G
  1  ATGTTCCCAACCAAAGACGTCGCACTCGCTGACCGCATCTGGGGCCCTATTAGCCATGGT
 21  H  V  L  K  A  D  N  Q  Y  Q  Y  D  P  V  A  A  L  F  A  D
 61  CACGTCCTGAAAGCGGACAATCAATATCAGTATGACCCGGTTGCCGCGTTGTTTGCGGAT
 41  R  Q  W  Q  E  F  F  W  D  A  N  D  I  Y  A  D  R  I  W  T
121  CGTCAATGGCAGGAGTTCTTCTGGGACGCTAACGACATCTACGCAGATCGTATCTGGACT
 61  P  R  V  T  G  G  A  M  R  N  I  W  Q  I  K  V  R  V  D
181  CCGCGCGTTACGGGCGGTGGCGCCATGCGCAACATTTGGCAGATCAAAGTCCGCGTGGAT
 81  M  V  R  N  Q  Y  I  P  S  I  N  V  H  H  Y  R  N  Q  Y  K
241  ATGGTACGCAATCAGTATATTCCGTCCATTAATGTTCACCACTACCGTAACCAGTACAAA
101  L  G  G  A  L  Q  A  K  A  D  R  I  W  R  F  H  E  R  N  G
301  CTGGGTGGTGCCCTGCAGGCGAAGGCGGATCGTATTTGGCGTCCGCACGAGCGCAATGGT
121  F  T  V  L  R  N  I  W  E  L  R  R  K  M  M  Y  M  A  D  N
361  TTTACGGTGCTGCGTAATATCTGGGAGCTGCGTCGTAAGATGATGTACATGGCGGATAAC
141  I  W  V  T  E  H  D  T  L  L  Y  K  R  Q  W  N  L  V  P  M
421  ATTTGGGTGACCGAACATGATACCCTGTTGTACAAACGTCAATGGAACCTGGTGCCGATG
161  V  A  T  V  K  R  Q  W  V  E  E  T  S  V  M  L  K  N  I
481  GTTGCAACGGTGAAGCGTCAATGGGTTCTGGAAGAAACCAGCGTCATGCTGAAGAACATC
181  W  H  H  H  H  H  H  *
541  TGGCATCATCATCACCACCACTAA
```

B  CMVpoly with proteasome and TAP linkers with no his tag

```
  1  M  F  P  T  K  D  V  A  L  A  D  R  I  W  G  P  I  S  H  G
  1  ATGTTCCCAACCAAAGACGTCGCACTCGCTGACCGCATCTGGGGCCCTATTAGCCATGGT
 21  H  V  L  K  A  D  N  Q  Y  Q  Y  D  P  V  A  A  L  F  A  D
 61  CACGTCCTGAAAGCGGACAATCAATATCAGTATGACCCGGTTGCCGCGTTGTTTGCGGAT
 41  R  Q  W  Q  E  F  F  W  D  A  N  D  I  Y  A  D  R  I  W  T
121  CGTCAATGGCAGGAGTTCTTCTGGGACGCTAACGACATCTACGCAGATCGTATCTGGACT
 61  P  R  V  T  G  G  A  M  R  N  I  W  Q  I  K  V  R  V  D
181  CCGCGCGTTACGGGCGGTGGCGCCATGCGCAACATTTGGCAGATCAAAGTCCGCGTGGAT
 81  M  V  R  N  Q  Y  I  P  S  I  N  V  H  H  Y  R  N  Q  Y  K
241  ATGGTACGCAATCAGTATATTCCGTCCATTAATGTTCACCACTACCGTAACCAGTACAAA
101  L  G  G  A  L  Q  A  K  A  D  R  I  W  R  F  H  E  R  N  G
301  CTGGGTGGTGCCCTGCAGGCGAAGGCGGATCGTATTTGGCGTCCGCACGAGCGCAATGGT
121  F  T  V  L  R  N  I  W  E  L  R  R  K  M  M  Y  M  A  D  N
361  TTTACGGTGCTGCGTAATATCTGGGAGCTGCGTCGTAAGATGATGTACATGGCGGATAAC
141  I  W  V  T  E  H  D  T  L  L  Y  K  R  Q  W  N  L  V  P  M
421  ATTTGGGTGACCGAACATGATACCCTGTTGTACAAACGTCAATGGAACCTGGTGCCGATG
161  V  A  T  V  K  R  Q  W  V  E  E  T  S  V  M  L  K  N  I
481  GTTGCAACGGTGAAGCGTCAATGGGTTCTGGAAGAAACCAGCGTCATGCTGAAGAACATC
181  W  *
541  TGGTAA
```

Figure 15

C CMVpoly14mer

```
  1  M  F  P  T  K  D  V  A  L  A  D  R  I  W  G  P  I  S  H  G
  1  ATGTTTCCAACCAAAGACGTTGCACTCGCTGACCGCATCTGGGGCCCTATTTCTCACGGT
 21  H  V  L  K  A  D  N  Q  Y  Q  Y  D  P  V  A  A  L  F  A  D
 61  CATGTTCTGAAGGCCGATAACCAATATCAGTACGACCCGGTCGCGGCATTGTTCGCGGAC
 41  R  Q  W  Q  E  F  F  W  D  A  N  D  I  Y  A  D  R  I  W  T
121  CGCCAGTGGCAAGAGTTCTTTTGGGATGCCAACGATATCTATGCGGATCGTATTTGGACG
 61  P  R  V  T  G  G  A  M  R  N  I  W  Q  I  K  V  R  V  D
181  CCGCGTGTGACGGGTGGTGGCGCGATGCGTAACATCTGGCAAATCAAAGTGCGTGTCGAC
 81  M  V  R  N  Q  Y  I  P  S  I  N  V  H  H  Y  R  N  Q  Y  T
241  ATGGTGCGTAATCAGTATATTCCGAGCATTAACGTGCATCACTACCGCAATCAATATACC
101  T  V  Y  P  S  S  T  A  K  A  D  N  Q  Y  R  P  H  E  R
301  ACGGTCTACCCGCCGAGCAGCACCGCAAAAGCTGACAATCAGTATCGTCCGCATGAGCGC
121  N  G  F  T  V  L  R  N  I  W  E  L  R  R  K  M  M  Y  M  A
361  AATGGTTTTACCGTGCTGCGTAATATCTGGGAACTGCGTCGTAAAATGATGTACATGGCG
141  D  N  I  W  V  T  E  H  D  T  L  L  Y  K  R  Q  W  N  L  V
421  GACAACATCTGGGTCACGGAGCACGATACCCTGCTGTACAAGCGCCAGTGGAATCTGGTC
161  P  M  V  A  T  V  K  R  Q  W  V  L  E  T  S  V  M  L  K
481  CCGATGGTTGCGACCGTTAAACGCCAGTGGGTTCTGGAAGAAACTTCCGTTATGCTGAAA
181  N  I  W  A  Y  A  Q  K  I  F  K  I  L  K  R  Q  W  H  H
541  AACATTTGGGCATACGCCCAAAAGATTTTCAAGATCCTGAAGCGTCAATGGCACCATCAC
201  H  H  H  *
601  CACCACCATTAA
```

D CMVpoly15mer

```
  1  M  F  P  T  K  D  V  A  L  A  D  R  I  W  G  P  I  S  H  G
  1  ATGTTTCCAACCAAAGACGTTGCACTCGCTGACCGCATCTGGGGCCCTATTTCTCACGGT
 21  H  V  L  K  A  D  N  Q  Y  Q  Y  D  P  V  A  A  L  F  A  D
 61  CATGTTCTGAAGGCCGATAACCAATATCAGTACGACCCGGTCGCGGCATTGTTCGCGGAC
 41  R  Q  W  Q  E  F  F  W  D  A  N  D  I  Y  A  D  R  I  W  T
121  CGCCAGTGGCAAGAGTTCTTTTGGGATGCCAACGATATCTATGCGGATCGTATTTGGACG
 61  P  R  V  T  G  G  A  M  R  N  I  W  Q  I  K  V  R  V  D
181  CCGCGTGTGACGGGTGGTGGCGCGATGCGTAACATCTGGCAAATCAAAGTGCGTGTCGAC
 81  M  V  R  N  Q  Y  I  P  S  I  N  V  H  H  Y  R  N  Q  Y  T
241  ATGGTGCGTAATCAGTATATTCCGAGCATTAACGTGCATCACTACCGCAATCAATATACC
101  T  V  Y  P  S  S  T  A  K  A  D  N  Q  Y  R  P  H  E  R
301  ACGGTCTACCCGCCGAGCAGCACCGCAAAAGCTGACAATCAGTATCGTCCGCATGAGCGC
121  N  G  F  T  V  L  R  N  I  W  E  L  R  R  K  M  M  Y  M  A
361  AATGGTTTTACCGTGCTGCGTAATATCTGGGAACTGCGTCGTAAAATGATGTACATGGCG
141  D  N  I  W  V  T  E  H  D  T  L  L  Y  K  R  Q  W  N  L  V
421  GACAACATCTGGGTCACGGAGCACGATACCCTGCTGTACAAGCGCCAGTGGAATCTGGTC
161  P  M  V  A  T  V  K  R  Q  W  V  L  E  T  S  V  M  L  K
481  CCGATGGTTGCGACCGTTAAACGCCAGTGGGTTCTGGAAGAAACTTCCGTTATGCTGAAA
181  N  I  W  A  Y  A  Q  K  I  F  K  I  L  K  R  Q  W  T  R  A
541  AACATTTGGGCATACGCCCAAAAGATTTTCAAGATCCTGAAGCGTCAATGGACCCGTGCG
201  T  K  M  Q  V  I  A  D  R  I  W  H  H  H  H  H  H  *
601  ACCAAGATGCAGGTGATCGCGGATCGCATTTGGCACCATCACCACCACCATTAA
```

Figure 15

E   CMVpoly20mer

```
  1   M   F   P   T   K   D   V   A   L   A   D   R   I   W   G   P   I   S   G   H
  1 ATGTTCCCGACTAAAGACGTTGCACTGGCCGACCGCATCTGGGGTCCGATTAGCGGTCAC
 21   V   L   K   A   D   N   Q   Y   Q   Y   D   P   V   A   A   L   F   A   D   R
 61 GTGCTGAAAGCAGACAACCAATACCAGTATGACCCGGTCGCAGCGCTGTTTGCGGATCGC
 41   Q   W   Q   E   F   F   W   D   A   N   D   I   Y   A   D   R   I   W   T   P
121 CAGTGGCAAGAGTTCTTTTGGGACGCAAATGACATTTATGCCGATCGCATCTGGACGCCT
 61   R   V   T   G   G   G   A   M   R   N   I   W   Q   I   K   V   R   V   D   M
181 CGTGTGACCGGTGGTGGCGCAATGCGTAATATCTGGCAGATTAAGGTGCGTGTGGATATG
 81   V   R   N   Q   Y   I   P   S   I   N   V   H   H   Y   R   N   Q   Y   K   L
241 GTGCGTAATCAGTATATTCCGAGCATCAATGTTCACCATTATCGTAATCAATACAAGCTG
101   G   G   A   L   Q   A   K   A   D   R   I   W   R   P   H   E   R   N   G   F
301 GGTGGCGCCCTGCAGGCTAAGGCAGATCGTATCTGGCGTCCGCATGAGCGTAACGGTTTT
121   T   V   R   N   I   W   E   L   R   R   K   M   M   Y   M   A   D   N   I   W
361 ACGGTCCGTAACATCTGGGAATTGCGTCGCAAAATGATGTATATGGCCGACAACATTTGG
141   V   T   E   H   D   T   L   L   Y   K   R   Q   W   N   L   V   P   M   V   A
421 GTTACCGAGCATGACACCCTGCTGTACAAACGCCAGTGGAATCTGGTGCCGATGGTTGCG
161   T   V   K   R   Q   W   V   L   E   E   T   S   V   M   L   K   N   I   W   A
481 ACGGTTAAGCGCCAATGGGTTCTGGAAGAAACCTCTGTCATGCTGAAGAATATCTGGGCG
181   Y   A   Q   K   I   F   K   I   L   A   D   R   I   W   T   R   A   T   K   M
541 TATGCCCAGAAGATTTTCAAGATTCTGGCCGATCGTATTTGGACGCGTGCAACCAAAATG
201   Q   V   I   A   D   R   Q   W   A   R   V   Y   E   I   K   C   R   R   N   Q
601 CAGGTCATTGCGGACCGTCAGTGGGCGCGTGTCTACGAAATCAAGTGCCGCCGTAACCAG
221   Y   C   P   S   Q   E   P   M   S   I   Y   V   V   K   R   Q   W   C   E   D
661 TATTGTCCGAGCCAGGAGCCGATGAGCATCTACGTGTACAAGCGTCAGTGGTGTGAGGAC
241   V   P   S   G   K   L   R   N   I   W   Y   A   Y   I   Y   T   T   Y   L   K
721 GTTCCGAGCGGCAAGCTGCGCAATATCTGGTACGCCTACATCTACACCACCTATCTGAAA
261   R   Q   W   Q   A   I   R   E   T   V   E   L   K   R   Q   W   H   H   H   H
781 CGTCAATGGCAAGCGATTCGTGAAACCGTTGAGCTGAAAAGACAATGGCACCACCATCAC
281   H   H   *
841 CACCATTAA
```

Figure 15

F   CMVpoly with no linkers

```
  1  M  F  P  T  K  D  V  A  L  G  P  I  S  H  G  H  V  L  K  Q
  1  ATGTTCCCAACTAAAGATGTAGCACTCGGTCCAATTTCGCACGGTCACGTTCTGAAGCAA
 21  Y  D  P  V  A  A  L  F  Q  E  F  F  W  D  A  N  D  I  Y  T
 61  TACGATCCGGTTGCCGCTCTGTTCCAGGAGTTCTTTTGGGACGCAAACGACATCTACACG
 41  P  R  V  T  G  G  A  M  Q  I  K  V  R  V  D  M  V  I  P
121  CCGCGTGTTACCGGCGGTGGCGCGATGCAGATCAAGGTGCGCGTGGATATGGTGATTCCG
 61  S  I  N  V  H  H  Y  K  L  G  G  A  L  Q  A  K  R  P  H  E
181  AGCATCAATGTGCACCACTATAAACTGGGTGGTGCGTTGCAAGCGAAACGTCCGCATGAG
 81  R  N  G  F  T  V  L  E  L  R  R  K  M  M  Y  M  V  T  E  H
241  CGTAACGGCTTTACGGTTCTGGAACTGCGTCGCAAGATGATGTACATGGTGACCGAGCAT
101  D  T  L  L  Y  N  L  V  P  M  V  A  T  V  V  L  E  E  T  S
301  GACACCCTGTTGTATAATCTGGTCCCGATGGTTGCGACCGTCGTCCTGGAAGAAACGAGC
121  V  M  L  H  H  H  H  H  H  *
361  GTCATGCTGCACCACCATCATCATCACTAA
```

G   CMVpoly with proteasome linkers

```
  1  M  F  P  T  K  D  V  A  L  A  D  G  P  I  S  H  G  H  V  L
  1  ATGTTCCCAACTAAAGATGTCGCACTCGCAGATGGTCCAATTTCTCACGGTCACGTATTG
 21  K  A  D  Q  Y  D  P  V  A  A  L  F  A  D  Q  E  F  F  W  D
 61  AAGGCGGATCAGTACGACCCGGTTGCCGCTCTGTTTGCCGATCAAGAGTTCTTCTGGGAC
 41  A  N  D  I  Y  A  D  T  P  R  V  T  G  G  A  M  R  Q  I
121  GCTAACGATATCTATGCCGACACCCCGCGTGTGACGGGTGGTGGCGCAATGCGCCAAATC
 61  K  V  R  V  D  M  V  R  I  P  S  I  N  V  H  H  Y  R  K  L
181  AAGGTCCGTGTTGACATGGTTCGCATTCCGAGCATCAATGTTCATCATTATCGCAAACTG
 81  G  G  A  L  Q  A  K  A  D  R  P  H  E  R  N  G  F  T  V  L
241  GGCGGTGCGCTGCAGGCGAAAGCGGACCGTCCGCACGAGCGTAATGGCTTTACGGTGTTG
101  R  E  L  R  R  K  M  M  Y  M  A  D  V  T  E  H  D  T  L  L
301  CGCGAGCTGCGTCGTAAGATGATGTACATGGCGGACGTCACGGAACACGATACCCTGCTG
121  Y  K  N  L  V  P  M  V  A  T  V  K  V  L  E  E  T  S  V  M
361  TACAAAAACCTGGTCCCGATGGTTGCGACCGTGAAGGTGCTGGAAGAAACCAGCGTGATG
141  L  K  H  H  H  H  H  H  *
421  CTGAAACATCACCATCACCACCATTAA
```

Figure 15

H EBVpoly

```
  1  M  H  P  V  G  E  A  D  Y  F  E  Y  R  S  S  C  S  S  C  P
  1 ATGCATCCAGTTGGTGAAGCAGACTACTTTGAATACCGTTCCTCTTGCAGCTCGTGTCCG
 21  L  S  K  I  A  D  R  P  P  I  F  I  R  R  L  K  F  L  R  G
 61 CTGAGCAAGATTGCAGATCGTCCGCCGATCTTCATCCGTCGTTTGAAATTTCTGCGCGGT
 41  R  A  Y  G  L  R  G  L  C  T  L  V  A  M  L  A  D  E  C
121 CGCGCGTACGGCTTGCGTGGTCTGTGCACCCTGGTGGCCATGCTGGCGGACGAGGAGTGT
 61  D  S  E  L  E  I  K  R  Y  K  C  L  G  G  L  L  T  M  V  A
181 GATAGCGAGCTCGAAATCAAACGCTATAAGTGCCTGGGTGGCCTTCTGACGATGGTTGCT
 81  D  R  A  K  F  K  Q  L  L  R  A  T  I  G  T  A  M  Y  K  A
241 GACCGTGCGAAGTTTAAGCAACTGCTGCGCGCCACCATTGGTACGGCAATGTATAAAGCT
101  D  T  Y  G  P  V  F  M  C  L  K  L  P  E  P  L  P  Q  G  Q
301 GACACCTATGGCCCGGTTTTCATGTGTCTGAAGCTGCCGGAGCCGCTGCCGCAGGGTCAA
121  L  T  A  Y  K  I  E  D  P  P  F  N  S  L  A  D  V  S  F  I
361 CTGACCGCATACAAGATTGAGGACCCGCCGTTCAATAGCCTGGCGGACGTGAGCTTCATT
141  E  F  V  G  W  K  E  E  N  L  L  D  F  V  R  F  M  G  V  K
421 GAATTTGTCGGCTGGAAAGAAGAGAATTTGCTGGACTTCGTCCGCTTCATGGGCGTGAAA
161  Q  N  G  A  L  A  I  N  T  F  R  P  Y  L  F  W  L  A  A  I
481 CAGAACGGTGCTCTGGCAATCAACACGTTTCGTCCGTACCTGTTCTGGCTGGCGGCCATT
181  R  A  Y  S  S  W  M  Y  S  Y  A  D  R  V  R  A  Y  T  Y  S
541 CGTGCGTATAGCAGCTGGATGTACAGCTATGCCGATCGTGTCCGCGCGTACACCTACTCC
201  K  A  D  R  R  I  Y  D  L  I  E  L  R  V  E  I  T  P  Y  K
601 AAAGCGGATCGTCGTATCTACGATCTGATCGAGCTGCGTGTTGAAATTACCCCGTATAAA
221  P  T  W  A  D  H  H  H  H  H  H  *
661 CCTACTTGGGCGGATCACCATCATCACCACCACTAA
```

Figure 15

SEQUENCE LISTING

```
<160> NUMBER OF SEQ ID NOS: 77

<210> SEQ ID NO 1
<211> LENGTH: 8
<212> TYPE: PRT
<213> ORGANISM: Human cytomegalovirus

<400> SEQUENCE: 1

Phe Pro Thr Lys Asp Val Ala Leu
1               5

<210> SEQ ID NO 2
<211> LENGTH: 10
<212> TYPE: PRT
<213> ORGANISM: Human cytomegalovirus

<400> SEQUENCE: 2

Gly Pro Ile Ser His Gly His Val Leu Lys
```

```
1               5                   10

<210> SEQ ID NO 3
<211> LENGTH: 9
<212> TYPE: PRT
<213> ORGANISM: Human cytomegalovirus

<400> SEQUENCE: 3

Gln Tyr Asp Pro Val Ala Ala Leu Phe
1               5

<210> SEQ ID NO 4
<211> LENGTH: 11
<212> TYPE: PRT
<213> ORGANISM: Human cytomegalovirus

<400> SEQUENCE: 4

Gln Glu Phe Phe Trp Asp Ala Asn Asp Ile Tyr
1               5                   10

<210> SEQ ID NO 5
<211> LENGTH: 10
<212> TYPE: PRT
<213> ORGANISM: Human cytomegalovirus

<400> SEQUENCE: 5

Thr Pro Arg Val Thr Gly Gly Gly Ala Met
1               5                   10

<210> SEQ ID NO 6
<211> LENGTH: 9
<212> TYPE: PRT
<213> ORGANISM: Human cytomegalovirus

<400> SEQUENCE: 6

Gln Ile Lys Val Arg Val Asp Met Val
1               5

<210> SEQ ID NO 7
<211> LENGTH: 9
<212> TYPE: PRT
<213> ORGANISM: Human cytomegalovirus

<400> SEQUENCE: 7

Ile Pro Ser Ile Asn Val His His Tyr
1               5

<210> SEQ ID NO 8
<211> LENGTH: 9
<212> TYPE: PRT
<213> ORGANISM: Human cytomegalovirus

<400> SEQUENCE: 8

Lys Leu Gly Gly Ala Leu Gln Ala Lys
1               5

<210> SEQ ID NO 9
<211> LENGTH: 11
<212> TYPE: PRT
<213> ORGANISM: Human cytomegalovirus

<400> SEQUENCE: 9

Arg Pro His Glu Arg Asn Gly Phe Thr Val Leu
1               5                   10
```

```
<210> SEQ ID NO 10
<211> LENGTH: 9
<212> TYPE: PRT
<213> ORGANISM: Human cytomegalovirus

<400> SEQUENCE: 10

Glu Leu Arg Arg Lys Met Met Tyr Met
1               5

<210> SEQ ID NO 11
<211> LENGTH: 9
<212> TYPE: PRT
<213> ORGANISM: Human cytomegalovirus

<400> SEQUENCE: 11

Val Thr Glu His Asp Thr Leu Leu Tyr
1               5

<210> SEQ ID NO 12
<211> LENGTH: 9
<212> TYPE: PRT
<213> ORGANISM: Human cytomegalovirus

<400> SEQUENCE: 12

Asn Leu Val Pro Met Val Ala Thr Val
1               5

<210> SEQ ID NO 13
<211> LENGTH: 9
<212> TYPE: PRT
<213> ORGANISM: Human cytomegalovirus

<400> SEQUENCE: 13

Val Leu Glu Glu Thr Ser Val Met Leu
1               5

<210> SEQ ID NO 14
<211> LENGTH: 11
<212> TYPE: PRT
<213> ORGANISM: Human cytomegalovirus

<400> SEQUENCE: 14

Thr Thr Val Tyr Pro Pro Ser Ser Thr Ala Lys
1               5                   10

<210> SEQ ID NO 15
<211> LENGTH: 10
<212> TYPE: PRT
<213> ORGANISM: Human cytomegalovirus

<400> SEQUENCE: 15

Ala Tyr Ala Gln Lys Ile Phe Lys Ile Leu
1               5                   10

<210> SEQ ID NO 16
<211> LENGTH: 9
<212> TYPE: PRT
<213> ORGANISM: Human cytomegalovirus

<400> SEQUENCE: 16

Ala Arg Val Tyr Glu Ile Lys Cys Arg
1               5

<210> SEQ ID NO 17
```

```
<211> LENGTH: 12
<212> TYPE: PRT
<213> ORGANISM: Human cytomegalovirus

<400> SEQUENCE: 17

Cys Pro Ser Gln Glu Pro Met Ser Ile Tyr Val Tyr
1               5                   10

<210> SEQ ID NO 18
<211> LENGTH: 9
<212> TYPE: PRT
<213> ORGANISM: Human cytomegalovirus

<400> SEQUENCE: 18

Cys Glu Asp Val Pro Ser Gly Lys Leu
1               5

<210> SEQ ID NO 19
<211> LENGTH: 9
<212> TYPE: PRT
<213> ORGANISM: Human cytomegalovirus

<400> SEQUENCE: 19

Tyr Ala Tyr Ile Tyr Thr Thr Tyr Leu
1               5

<210> SEQ ID NO 20
<211> LENGTH: 9
<212> TYPE: PRT
<213> ORGANISM: Human cytomegalovirus

<400> SEQUENCE: 20

Gln Ala Ile Arg Glu Thr Val Glu Leu
1               5

<210> SEQ ID NO 21
<211> LENGTH: 9
<212> TYPE: PRT
<213> ORGANISM: Human cytomegalovirus

<400> SEQUENCE: 21

Thr Arg Ala Thr Lys Met Gln Val Ile
1               5

<210> SEQ ID NO 22
<211> LENGTH: 9
<212> TYPE: PRT
<213> ORGANISM: Epstein-Barr virus

<400> SEQUENCE: 22

Gly Leu Cys Thr Leu Val Ala Met Leu
1               5

<210> SEQ ID NO 23
<211> LENGTH: 9
<212> TYPE: PRT
<213> ORGANISM: Epstein-Barr virus

<400> SEQUENCE: 23

Cys Leu Gly Gly Leu Leu Thr Met Val
1               5

<210> SEQ ID NO 24
<211> LENGTH: 9
<212> TYPE: PRT
```

<213> ORGANISM: Epstein-Barr virus

<400> SEQUENCE: 24

Arg Val Arg Ala Tyr Thr Tyr Ser Lys
1               5

<210> SEQ ID NO 25
<211> LENGTH: 9
<212> TYPE: PRT
<213> ORGANISM: Epstein-Barr virus

<400> SEQUENCE: 25

Ala Thr Ile Gly Thr Ala Met Tyr Lys
1               5

<210> SEQ ID NO 26
<211> LENGTH: 11
<212> TYPE: PRT
<213> ORGANISM: Epstein-Barr virus

<400> SEQUENCE: 26

Ser Ser Cys Ser Ser Cys Pro Leu Ser Lys Ile
1               5                   10

<210> SEQ ID NO 27
<211> LENGTH: 9
<212> TYPE: PRT
<213> ORGANISM: Epstein-Barr virus

<400> SEQUENCE: 27

Pro Tyr Leu Phe Trp Leu Ala Ala Ile
1               5

<210> SEQ ID NO 28
<211> LENGTH: 9
<212> TYPE: PRT
<213> ORGANISM: Epstein-Barr virus

<400> SEQUENCE: 28

Thr Tyr Gly Pro Val Phe Met Cys Leu
1               5

<210> SEQ ID NO 29
<211> LENGTH: 9
<212> TYPE: PRT
<213> ORGANISM: Epstein-Barr virus

<400> SEQUENCE: 29

Ala Tyr Ser Ser Trp Met Tyr Ser Tyr
1               5

<210> SEQ ID NO 30
<211> LENGTH: 9
<212> TYPE: PRT
<213> ORGANISM: Epstein-Barr virus

<400> SEQUENCE: 30

Arg Pro Pro Ile Phe Ile Arg Arg Leu
1               5

<210> SEQ ID NO 31
<211> LENGTH: 9
<212> TYPE: PRT
<213> ORGANISM: Epstein-Barr virus

```
<400> SEQUENCE: 31

Phe Leu Arg Gly Arg Ala Tyr Gly Leu
1               5

<210> SEQ ID NO 32
<211> LENGTH: 8
<212> TYPE: PRT
<213> ORGANISM: Epstein-Barr virus

<400> SEQUENCE: 32

Arg Ala Lys Phe Lys Gln Leu Leu
1               5

<210> SEQ ID NO 33
<211> LENGTH: 10
<212> TYPE: PRT
<213> ORGANISM: Epstein-Barr virus

<400> SEQUENCE: 33

Gln Asn Gly Ala Leu Ala Ile Asn Thr Phe
1               5                   10

<210> SEQ ID NO 34
<211> LENGTH: 9
<212> TYPE: PRT
<213> ORGANISM: Epstein-Barr virus

<400> SEQUENCE: 34

Arg Arg Ile Tyr Asp Leu Ile Glu Leu
1               5

<210> SEQ ID NO 35
<211> LENGTH: 11
<212> TYPE: PRT
<213> ORGANISM: Epstein-Barr virus

<400> SEQUENCE: 35

His Pro Val Gly Glu Ala Asp Tyr Phe Glu Tyr
1               5                   10

<210> SEQ ID NO 36
<211> LENGTH: 13
<212> TYPE: PRT
<213> ORGANISM: Epstein-Barr virus

<400> SEQUENCE: 36

Leu Pro Glu Pro Leu Pro Gln Gly Gln Leu Thr Ala Tyr
1               5                   10

<210> SEQ ID NO 37
<211> LENGTH: 9
<212> TYPE: PRT
<213> ORGANISM: Epstein-Barr virus

<400> SEQUENCE: 37

Ile Glu Asp Pro Pro Phe Asn Ser Leu
1               5

<210> SEQ ID NO 38
<211> LENGTH: 13
<212> TYPE: PRT
<213> ORGANISM: Epstein-Barr virus

<400> SEQUENCE: 38
```

```
Glu Glu Asn Leu Leu Asp Phe Val Arg Phe Met Gly Val
1               5                   10
```

<210> SEQ ID NO 39
<211> LENGTH: 10
<212> TYPE: PRT
<213> ORGANISM: Epstein-Barr virus

<400> SEQUENCE: 39

```
Val Glu Ile Thr Pro Tyr Lys Pro Thr Trp
1               5                   10
```

<210> SEQ ID NO 40
<211> LENGTH: 12
<212> TYPE: PRT
<213> ORGANISM: Epstein-Barr virus

<400> SEQUENCE: 40

```
Glu Glu Cys Asp Ser Glu Leu Glu Ile Lys Arg Tyr
1               5                   10
```

<210> SEQ ID NO 41
<211> LENGTH: 9
<212> TYPE: PRT
<213> ORGANISM: Epstein-Barr virus

<400> SEQUENCE: 41

```
Val Ser Phe Ile Glu Phe Val Gly Trp
1               5
```

<210> SEQ ID NO 42
<211> LENGTH: 187
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

```
Met Phe Pro Thr Lys Asp Val Ala Leu Ala Asp Arg Ile Trp Gly Pro
1               5                   10                  15

Ile Ser His Gly His Val Leu Lys Ala Asp Asn Gln Tyr Gln Tyr Asp
                20                  25                  30

Pro Val Ala Ala Leu Phe Ala Asp Arg Gln Trp Gln Glu Phe Phe Trp
            35                  40                  45

Asp Ala Asn Asp Ile Tyr Ala Asp Arg Ile Trp Thr Pro Arg Val Thr
        50                  55                  60

Gly Gly Gly Ala Met Arg Asn Ile Trp Gln Ile Lys Val Arg Val Asp
65                  70                  75                  80

Met Val Arg Asn Gln Tyr Ile Pro Ser Ile Asn Val His His Tyr Arg
                85                  90                  95

Asn Gln Tyr Lys Leu Gly Gly Ala Leu Gln Ala Lys Ala Asp Arg Ile
                100                 105                 110

Trp Arg Pro His Glu Arg Asn Gly Phe Thr Val Leu Arg Asn Ile Trp
            115                 120                 125

Glu Leu Arg Arg Lys Met Met Tyr Met Ala Asp Asn Ile Trp Val Thr
        130                 135                 140

Glu His Asp Thr Leu Leu Tyr Lys Arg Gln Trp Asn Leu Val Pro Met
145                 150                 155                 160

Val Ala Thr Val Lys Arg Gln Trp Val Leu Glu Glu Thr Ser Val Met
                165                 170                 175
```

Leu Lys Asn Ile Trp His His His His His His
            180                 185

<210> SEQ ID NO 43
<211> LENGTH: 181
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Met Phe Pro Thr Lys Asp Val Ala Leu Ala Asp Arg Ile Trp Gly Pro
1               5                   10                  15

Ile Ser His Gly His Val Leu Lys Ala Asp Asn Gln Tyr Gln Tyr Asp
            20                  25                  30

Pro Val Ala Ala Leu Phe Ala Asp Arg Gln Trp Gln Glu Phe Phe Trp
        35                  40                  45

Asp Ala Asn Asp Ile Tyr Ala Asp Arg Ile Trp Thr Pro Arg Val Thr
    50                  55                  60

Gly Gly Gly Ala Met Arg Asn Ile Trp Gln Ile Lys Val Arg Val Asp
65                  70                  75                  80

Met Val Arg Asn Gln Tyr Ile Pro Ser Ile Asn Val His His Tyr Arg
                85                  90                  95

Asn Gln Tyr Lys Leu Gly Gly Ala Leu Gln Ala Lys Ala Asp Arg Ile
            100                 105                 110

Trp Arg Pro His Glu Arg Asn Gly Phe Thr Val Leu Arg Asn Ile Trp
        115                 120                 125

Glu Leu Arg Arg Lys Met Met Tyr Met Ala Asp Asn Ile Trp Val Thr
    130                 135                 140

Glu His Asp Thr Leu Leu Tyr Lys Arg Gln Trp Asn Leu Val Pro Met
145                 150                 155                 160

Val Ala Thr Val Lys Arg Gln Trp Val Leu Glu Glu Thr Ser Val Met
                165                 170                 175

Leu Lys Asn Ile Trp
            180

<210> SEQ ID NO 44
<211> LENGTH: 203
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Met Phe Pro Thr Lys Asp Val Ala Leu Ala Asp Arg Ile Trp Gly Pro
1               5                   10                  15

Ile Ser His Gly His Val Leu Lys Ala Asp Asn Gln Tyr Gln Tyr Asp
            20                  25                  30

Pro Val Ala Ala Leu Phe Ala Asp Arg Gln Trp Gln Glu Phe Phe Trp
        35                  40                  45

Asp Ala Asn Asp Ile Tyr Ala Asp Arg Ile Trp Thr Pro Arg Val Thr
    50                  55                  60

Gly Gly Gly Ala Met Arg Asn Ile Trp Gln Ile Lys Val Arg Val Asp
65                  70                  75                  80

Met Val Arg Asn Gln Tyr Ile Pro Ser Ile Asn Val His His Tyr Arg
                85                  90                  95

```
Asn Gln Tyr Thr Thr Val Tyr Pro Pro Ser Thr Ala Lys Ala Asp
            100                 105                 110

Asn Gln Tyr Arg Pro His Glu Arg Asn Gly Phe Thr Val Leu Arg Asn
            115                 120                 125

Ile Trp Glu Leu Arg Arg Lys Met Met Tyr Met Ala Asp Asn Ile Trp
    130                 135                 140

Val Thr Glu His Asp Thr Leu Leu Tyr Lys Arg Gln Trp Asn Leu Val
145                 150                 155                 160

Pro Met Val Ala Thr Val Lys Arg Gln Trp Val Leu Glu Glu Thr Ser
                165                 170                 175

Val Met Leu Lys Asn Ile Trp Ala Tyr Ala Gln Lys Ile Phe Lys Ile
            180                 185                 190

Leu Lys Arg Gln Trp His His His His His His
            195                 200
```

<210> SEQ ID NO 45
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

```
Met Phe Pro Thr Lys Asp Val Ala Leu Ala Asp Arg Ile Trp Gly Pro
1               5                   10                  15

Ile Ser His Gly His Val Leu Lys Ala Asp Asn Gln Tyr Gln Tyr Asp
            20                  25                  30

Pro Val Ala Ala Leu Phe Ala Asp Arg Gln Trp Gln Glu Phe Phe Trp
        35                  40                  45

Asp Ala Asn Asp Ile Tyr Ala Asp Arg Ile Trp Thr Pro Arg Val Thr
    50                  55                  60

Gly Gly Gly Ala Met Arg Asn Ile Trp Gln Ile Lys Val Arg Val Asp
65                  70                  75                  80

Met Val Arg Asn Gln Tyr Ile Pro Ser Ile Asn Val His His Tyr Arg
                85                  90                  95

Asn Gln Tyr Thr Thr Val Tyr Pro Pro Ser Thr Ala Lys Ala Asp
            100                 105                 110

Asn Gln Tyr Arg Pro His Glu Arg Asn Gly Phe Thr Val Leu Arg Asn
            115                 120                 125

Ile Trp Glu Leu Arg Arg Lys Met Met Tyr Met Ala Asp Asn Ile Trp
    130                 135                 140

Val Thr Glu His Asp Thr Leu Leu Tyr Lys Arg Gln Trp Asn Leu Val
145                 150                 155                 160

Pro Met Val Ala Thr Val Lys Arg Gln Trp Val Leu Glu Glu Thr Ser
                165                 170                 175

Val Met Leu Lys Asn Ile Trp Ala Tyr Ala Gln Lys Ile Phe Lys Ile
            180                 185                 190

Leu Lys Arg Gln Trp Thr Arg Ala Thr Lys Met Gln Val Ile Ala Asp
            195                 200                 205

Arg Ile Trp His His His His His His
    210                 215
```

<210> SEQ ID NO 46
<211> LENGTH: 282
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 46

```
Met Phe Pro Thr Lys Asp Val Ala Leu Ala Asp Arg Ile Trp Gly Pro
1               5                   10                  15

Ile Ser Gly His Val Leu Lys Ala Asp Asn Gln Tyr Gln Tyr Asp Pro
            20                  25                  30

Val Ala Ala Leu Phe Ala Asp Arg Gln Trp Gln Glu Phe Phe Trp Asp
        35                  40                  45

Ala Asn Asp Ile Tyr Ala Asp Arg Ile Trp Thr Pro Arg Val Thr Gly
    50                  55                  60

Gly Gly Ala Met Arg Asn Ile Trp Gln Ile Lys Val Arg Val Asp Met
65                  70                  75                  80

Val Arg Asn Gln Tyr Ile Pro Ser Ile Asn Val His His Tyr Arg Asn
                85                  90                  95

Gln Tyr Lys Leu Gly Gly Ala Leu Gln Ala Lys Ala Asp Arg Ile Trp
            100                 105                 110

Arg Pro His Glu Arg Asn Gly Phe Thr Val Arg Asn Ile Trp Glu Leu
        115                 120                 125

Arg Arg Lys Met Met Tyr Met Ala Asp Asn Ile Trp Val Thr Glu His
    130                 135                 140

Asp Thr Leu Leu Tyr Lys Arg Gln Trp Asn Leu Val Pro Met Val Ala
145                 150                 155                 160

Thr Val Lys Arg Gln Trp Val Leu Glu Glu Thr Ser Val Met Leu Lys
                165                 170                 175

Asn Ile Trp Ala Tyr Ala Gln Lys Ile Phe Lys Ile Leu Ala Asp Arg
            180                 185                 190

Ile Trp Thr Arg Ala Thr Lys Met Gln Val Ile Ala Asp Arg Gln Trp
        195                 200                 205

Ala Arg Val Tyr Glu Ile Lys Cys Arg Arg Asn Gln Tyr Cys Pro Ser
    210                 215                 220

Gln Glu Pro Met Ser Ile Tyr Val Tyr Lys Arg Gln Trp Cys Glu Asp
225                 230                 235                 240

Val Pro Ser Gly Lys Leu Arg Asn Ile Trp Tyr Ala Tyr Ile Tyr Thr
                245                 250                 255

Thr Tyr Leu Lys Arg Gln Trp Gln Ala Ile Arg Glu Thr Val Glu Leu
            260                 265                 270

Lys Arg Gln Trp His His His His His His
        275                 280
```

<210> SEQ ID NO 47
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

```
Met Phe Pro Thr Lys Asp Val Ala Leu Gly Pro Ile Ser His Gly His
1               5                   10                  15

Val Leu Lys Gln Tyr Asp Pro Val Ala Ala Leu Phe Gln Glu Phe Phe
            20                  25                  30

Trp Asp Ala Asn Asp Ile Tyr Thr Pro Arg Val Thr Gly Gly Gly Ala
```

```
            35                  40                  45
Met Gln Ile Lys Val Arg Val Asp Met Val Ile Pro Ser Ile Asn Val
         50                  55                  60

His His Tyr Lys Leu Gly Gly Ala Leu Gln Ala Lys Arg Pro His Glu
 65                  70                  75                  80

Arg Asn Gly Phe Thr Val Leu Glu Leu Arg Arg Lys Met Met Tyr Met
                 85                  90                  95

Val Thr Glu His Asp Thr Leu Leu Tyr Asn Leu Val Pro Met Val Ala
            100                 105                 110

Thr Val Val Leu Glu Glu Thr Ser Val Met Leu His His His His
        115                 120                 125

His

<210> SEQ ID NO 48
<211> LENGTH: 148
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Met Phe Pro Thr Lys Asp Val Ala Leu Ala Asp Gly Pro Ile Ser His
 1               5                  10                  15

Gly His Val Leu Lys Ala Asp Gln Tyr Asp Pro Val Ala Ala Leu Phe
             20                  25                  30

Ala Asp Gln Glu Phe Phe Trp Asp Ala Asn Asp Ile Tyr Ala Asp Thr
         35                  40                  45

Pro Arg Val Thr Gly Gly Gly Ala Met Arg Gln Ile Lys Val Arg Val
     50                  55                  60

Asp Met Val Arg Ile Pro Ser Ile Asn Val His His Tyr Arg Lys Leu
 65                  70                  75                  80

Gly Gly Ala Leu Gln Ala Lys Ala Asp Arg Pro His Glu Arg Asn Gly
                 85                  90                  95

Phe Thr Val Leu Arg Glu Leu Arg Arg Lys Met Met Tyr Met Ala Asp
            100                 105                 110

Val Thr Glu His Asp Thr Leu Leu Tyr Lys Asn Leu Val Pro Met Val
        115                 120                 125

Ala Thr Val Lys Val Leu Glu Glu Thr Ser Val Met Leu Lys His His
    130                 135                 140

His His His His
145

<210> SEQ ID NO 49
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Met His Pro Val Gly Glu Ala Asp Tyr Phe Glu Tyr Arg Ser Ser Cys
 1               5                  10                  15

Ser Ser Cys Pro Leu Ser Lys Ile Ala Asp Arg Pro Ile Phe Ile
             20                  25                  30

Arg Arg Leu Lys Phe Leu Arg Gly Arg Ala Tyr Gly Leu Arg Gly Leu
         35                  40                  45
```

```
Cys Thr Leu Val Ala Met Leu Ala Asp Glu Glu Cys Asp Ser Glu Leu
         50                  55                  60

Glu Ile Lys Arg Tyr Lys Cys Leu Gly Gly Leu Leu Thr Met Val Ala
 65                  70                  75                  80

Asp Arg Ala Lys Phe Lys Gln Leu Leu Arg Ala Thr Ile Gly Thr Ala
                     85                  90                  95

Met Tyr Lys Ala Asp Thr Tyr Gly Pro Val Phe Met Cys Leu Lys Leu
                100                 105                 110

Pro Glu Pro Leu Pro Gln Gly Gln Leu Thr Ala Tyr Lys Ile Glu Asp
                115                 120                 125

Pro Pro Phe Asn Ser Leu Ala Asp Val Ser Phe Ile Glu Phe Val Gly
            130                 135                 140

Trp Lys Glu Glu Asn Leu Leu Asp Phe Val Arg Phe Met Gly Val Lys
145                 150                 155                 160

Gln Asn Gly Ala Leu Ala Ile Asn Thr Phe Arg Pro Tyr Leu Phe Trp
                    165                 170                 175

Leu Ala Ala Ile Arg Ala Tyr Ser Ser Trp Met Tyr Ser Tyr Ala Asp
                180                 185                 190

Arg Val Arg Ala Tyr Thr Tyr Ser Lys Ala Asp Arg Arg Ile Tyr Asp
                195                 200                 205

Leu Ile Glu Leu Arg Val Glu Ile Thr Pro Tyr Lys Pro Thr Trp Ala
210                 215                 220

Asp His His His His His
225                 230

<210> SEQ ID NO 50
<211> LENGTH: 564
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(561)

<400> SEQUENCE: 50 atg ttc cca acc aaa gac gtc gca ctc gct gac cgc atc tgg ggc cct      48
Met Phe Pro Thr Lys Asp Val Ala Leu Ala Asp Arg Ile Trp Gly Pro
 1               5                  10                  15 att agc cat ggt cac gtc ctg aaa gcg gac aat caa tat cag tat gac      96
Ile Ser His Gly His Val Leu Lys Ala Asp Asn Gln Tyr Gln Tyr Asp
                 20                  25                  30 ccg gtt gcc gcg ttg ttt gcg gat cgt caa tgg cag gag ttc ttc tgg     144
Pro Val Ala Ala Leu Phe Ala Asp Arg Gln Trp Gln Glu Phe Phe Trp
             35                  40                  45 gac gct aac gac atc tac gca gat cgt atc tgg act ccg cgc gtt acg     192
Asp Ala Asn Asp Ile Tyr Ala Asp Arg Ile Trp Thr Pro Arg Val Thr
 50                  55                  60 ggc ggt ggc gcc atg cgc aac att tgg cag atc aaa gtc cgc gtg gat     240
Gly Gly Gly Ala Met Arg Asn Ile Trp Gln Ile Lys Val Arg Val Asp
 65                  70                  75                  80 atg gta cgc aat cag tat att ccg tcc att aat gtt cac cac tac cgt     288
Met Val Arg Asn Gln Tyr Ile Pro Ser Ile Asn Val His His Tyr Arg
                     85                  90                  95 aac cag tac aaa ctg ggt ggt gcc ctg cag gcg aag gcg gat cgt att     336
Asn Gln Tyr Lys Leu Gly Gly Ala Leu Gln Ala Lys Ala Asp Arg Ile
                100                 105                 110
```

```
tgg cgt ccg cac gag cgc aat ggt ttt acg gtg ctg cgt aat atc tgg       384
Trp Arg Pro His Glu Arg Asn Gly Phe Thr Val Leu Arg Asn Ile Trp
        115                 120                 125 gag ctg cgt cgt aag atg atg tac atg gcg gat aac att tgg gtg acc       432
Glu Leu Arg Arg Lys Met Met Tyr Met Ala Asp Asn Ile Trp Val Thr
130                 135                 140 gaa cat gat acc ctg ttg tac aaa cgt caa tgg aac ctg gtg ccg atg       480
Glu His Asp Thr Leu Leu Tyr Lys Arg Gln Trp Asn Leu Val Pro Met
145                 150                 155                 160 gtt gca acg gtg aag cgt caa tgg gtt ctg gaa gaa acc agc gtc atg       528
Val Ala Thr Val Lys Arg Gln Trp Val Leu Glu Glu Thr Ser Val Met
                165                 170                 175 ctg aag aac atc tgg cat cat cat cac cac cac taa                       564
Leu Lys Asn Ile Trp His His His His His His
        180                 185
```

<210> SEQ ID NO 51
<211> LENGTH: 546
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<221> NAME/KEY: CDS
<222> LOCATION: (1)..(543)

<400> SEQUENCE: 51

```
atg ttc cca acc aaa gac gtc gca ctc gct gac cgc atc tgg ggc cct        48
Met Phe Pro Thr Lys Asp Val Ala Leu Ala Asp Arg Ile Trp Gly Pro
1               5                   10                  15 att agc cat ggt cac gtc ctg aaa gcg gac aat caa tat cag tat gac        96
Ile Ser His Gly His Val Leu Lys Ala Asp Asn Gln Tyr Gln Tyr Asp
            20                  25                  30 ccg gtt gcc gcg ttg ttt gcg gat cgt caa tgg cag gag ttc ttc tgg       144
Pro Val Ala Ala Leu Phe Ala Asp Arg Gln Trp Gln Glu Phe Phe Trp
        35                  40                  45 gac gct aac gac atc tac gca gat cgt atc tgg act ccg cgc gtt acg       192
Asp Ala Asn Asp Ile Tyr Ala Asp Arg Ile Trp Thr Pro Arg Val Thr
    50                  55                  60 ggc ggt ggc gcc atg cgc aac att tgg cag atc aaa gtc cgc gtg gat       240
Gly Gly Gly Ala Met Arg Asn Ile Trp Gln Ile Lys Val Arg Val Asp
65                  70                  75                  80 atg gta cgc aat cag tat att ccg tcc att aat gtt cac cac tac cgt       288
Met Val Arg Asn Gln Tyr Ile Pro Ser Ile Asn Val His His Tyr Arg
                85                  90                  95 aac cag tac aaa ctg ggt ggt gcc ctg cag gcg aag gcg gat cgt att       336
Asn Gln Tyr Lys Leu Gly Gly Ala Leu Gln Ala Lys Ala Asp Arg Ile
            100                 105                 110 tgg cgt ccg cac gag cgc aat ggt ttt acg gtg ctg cgt aat atc tgg       384
Trp Arg Pro His Glu Arg Asn Gly Phe Thr Val Leu Arg Asn Ile Trp
        115                 120                 125 gag ctg cgt cgt aag atg atg tac atg gcg gat aac att tgg gtg acc       432
Glu Leu Arg Arg Lys Met Met Tyr Met Ala Asp Asn Ile Trp Val Thr
130                 135                 140 gaa cat gat acc ctg ttg tac aaa cgt caa tgg aac ctg gtg ccg atg       480
Glu His Asp Thr Leu Leu Tyr Lys Arg Gln Trp Asn Leu Val Pro Met
145                 150                 155                 160 gtt gca acg gtg aag cgt caa tgg gtt ctg gaa gaa acc agc gtc atg       528
Val Ala Thr Val Lys Arg Gln Trp Val Leu Glu Glu Thr Ser Val Met
                165                 170                 175 ctg aag aac atc tgg taa                                               546
Leu Lys Asn Ile Trp
```

```
<210> SEQ ID NO 52
<211> LENGTH: 612
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(609)

<400> SEQUENCE: 52 atg ttt cca acc aaa gac gtt gca ctc gct gac cgc atc tgg ggc cct       48
Met Phe Pro Thr Lys Asp Val Ala Leu Ala Asp Arg Ile Trp Gly Pro
1               5                   10                  15 att tct cac ggt cat gtt ctg aag gcc gat aac caa tat cag tac gac       96
Ile Ser His Gly His Val Leu Lys Ala Asp Asn Gln Tyr Gln Tyr Asp
            20                  25                  30 ccg gtc gcg gca ttg ttc gcg gac cgc cag tgg caa gag ttc ttt tgg      144
Pro Val Ala Ala Leu Phe Ala Asp Arg Gln Trp Gln Glu Phe Phe Trp
        35                  40                  45 gat gcc aac gat atc tat gcg gat cgt att tgg acg ccg cgt gtg acg      192
Asp Ala Asn Asp Ile Tyr Ala Asp Arg Ile Trp Thr Pro Arg Val Thr
    50                  55                  60 ggt ggt ggc gcg atg cgt aac atc tgg caa atc aaa gtg cgt gtc gac      240
Gly Gly Gly Ala Met Arg Asn Ile Trp Gln Ile Lys Val Arg Val Asp
65                  70                  75                  80 atg gtg cgt aat cag tat att ccg agc att aac gtg cat cac tac cgc      288
Met Val Arg Asn Gln Tyr Ile Pro Ser Ile Asn Val His His Tyr Arg
                85                  90                  95 aat caa tat acc acg gtc tac ccg ccg agc agc acc gca aaa gct gac      336
Asn Gln Tyr Thr Thr Val Tyr Pro Pro Ser Ser Thr Ala Lys Ala Asp
            100                 105                 110 aat cag tat cgt ccg cat gag cgc aat ggt ttt acc gtg ctg cgt aat      384
Asn Gln Tyr Arg Pro His Glu Arg Asn Gly Phe Thr Val Leu Arg Asn
        115                 120                 125 atc tgg gaa ctg cgt cgt aaa atg atg tac atg gcg gac aac atc tgg      432
Ile Trp Glu Leu Arg Arg Lys Met Met Tyr Met Ala Asp Asn Ile Trp
    130                 135                 140 gtc acg gag cac gat acc ctg ctg tac aag cgc cag tgg aat ctg gtc      480
Val Thr Glu His Asp Thr Leu Leu Tyr Lys Arg Gln Trp Asn Leu Val
145                 150                 155                 160 ccg atg gtt gcg acc gtt aaa cgc cag tgg gtt ctg gaa gaa act tcc      528
Pro Met Val Ala Thr Val Lys Arg Gln Trp Val Leu Glu Glu Thr Ser
                165                 170                 175 gtt atg ctg aaa aac att tgg gca tac gcc caa aag att ttc aag atc      576
Val Met Leu Lys Asn Ile Trp Ala Tyr Ala Gln Lys Ile Phe Lys Ile
            180                 185                 190 ctg aag cgt caa tgg cac cat cac cac cac cat taa                      612
Leu Lys Arg Gln Trp His His His His His His
        195                 200

<210> SEQ ID NO 53
<211> LENGTH: 654
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
```

<222> LOCATION: (1)..(651)

<400> SEQUENCE: 53

| | | | | | | | | | | | | | | | | |
|---|---|---|---|---|---|---|---|---|---|---|---|---|---|---|---|---|
| atg | ttt | cca | acc | aaa | gac | gtt | gca | ctc | gct | gac | cgc | atc | tgg | ggc | cct | 48 |
| Met | Phe | Pro | Thr | Lys | Asp | Val | Ala | Leu | Ala | Asp | Arg | Ile | Trp | Gly | Pro | |
| 1 | | | | 5 | | | | | 10 | | | | | 15 | | |

| att | tct | cac | ggt | cat | gtt | ctg | aag | gcc | gat | aac | caa | tat | cag | tac | gac | 96 |
|---|---|---|---|---|---|---|---|---|---|---|---|---|---|---|---|---|
| Ile | Ser | His | Gly | His | Val | Leu | Lys | Ala | Asp | Asn | Gln | Tyr | Gln | Tyr | Asp | |
| | | | 20 | | | | | 25 | | | | | 30 | | | |

| ccg | gtc | gcg | gca | ttg | ttc | gcg | gac | cgc | cag | tgg | caa | gag | ttc | ttt | tgg | 144 |
|---|---|---|---|---|---|---|---|---|---|---|---|---|---|---|---|---|
| Pro | Val | Ala | Ala | Leu | Phe | Ala | Asp | Arg | Gln | Trp | Gln | Glu | Phe | Phe | Trp | |
| | | 35 | | | | | 40 | | | | | 45 | | | | |

| gat | gcc | aac | gat | atc | tat | gcg | gat | cgt | att | tgg | acg | ccg | cgt | gtg | acg | 192 |
|---|---|---|---|---|---|---|---|---|---|---|---|---|---|---|---|---|
| Asp | Ala | Asn | Asp | Ile | Tyr | Ala | Asp | Arg | Ile | Trp | Thr | Pro | Arg | Val | Thr | |
| | 50 | | | | | 55 | | | | | 60 | | | | | |

| ggt | ggt | ggc | gcg | atg | cgt | aac | atc | tgg | caa | atc | aaa | gtg | cgt | gtc | gac | 240 |
|---|---|---|---|---|---|---|---|---|---|---|---|---|---|---|---|---|
| Gly | Gly | Gly | Ala | Met | Arg | Asn | Ile | Trp | Gln | Ile | Lys | Val | Arg | Val | Asp | |
| 65 | | | | 70 | | | | | 75 | | | | | 80 | | |

| atg | gtg | cgt | aat | cag | tat | att | ccg | agc | att | aac | gtg | cat | cac | tac | cgc | 288 |
|---|---|---|---|---|---|---|---|---|---|---|---|---|---|---|---|---|
| Met | Val | Arg | Asn | Gln | Tyr | Ile | Pro | Ser | Ile | Asn | Val | His | His | Tyr | Arg | |
| | | | | 85 | | | | | 90 | | | | | 95 | | |

| aat | caa | tat | acc | acg | gtc | tac | ccg | ccg | agc | agc | acc | gca | aaa | gct | gac | 336 |
|---|---|---|---|---|---|---|---|---|---|---|---|---|---|---|---|---|
| Asn | Gln | Tyr | Thr | Thr | Val | Tyr | Pro | Pro | Ser | Ser | Thr | Ala | Lys | Ala | Asp | |
| | | | 100 | | | | | 105 | | | | | 110 | | | |

| aat | cag | tat | cgt | ccg | cat | gag | cgc | aat | ggt | ttt | acc | gtg | ctg | cgt | aat | 384 |
|---|---|---|---|---|---|---|---|---|---|---|---|---|---|---|---|---|
| Asn | Gln | Tyr | Arg | Pro | His | Glu | Arg | Asn | Gly | Phe | Thr | Val | Leu | Arg | Asn | |
| | | 115 | | | | | 120 | | | | | 125 | | | | |

| atc | tgg | gaa | ctg | cgt | cgt | aaa | atg | atg | tac | atg | gcg | gac | aac | atc | tgg | 432 |
|---|---|---|---|---|---|---|---|---|---|---|---|---|---|---|---|---|
| Ile | Trp | Glu | Leu | Arg | Arg | Lys | Met | Met | Tyr | Met | Ala | Asp | Asn | Ile | Trp | |
| | 130 | | | | | 135 | | | | | 140 | | | | | |

| gtc | acg | gag | cac | gat | acc | ctg | ctg | tac | aag | cgc | cag | tgg | aat | ctg | gtc | 480 |
|---|---|---|---|---|---|---|---|---|---|---|---|---|---|---|---|---|
| Val | Thr | Glu | His | Asp | Thr | Leu | Leu | Tyr | Lys | Arg | Gln | Trp | Asn | Leu | Val | |
| 145 | | | | 150 | | | | | 155 | | | | | 160 | | |

| ccg | atg | gtt | gcg | acc | gtt | aaa | cgc | cag | tgg | gtt | ctg | gaa | gaa | act | tcc | 528 |
|---|---|---|---|---|---|---|---|---|---|---|---|---|---|---|---|---|
| Pro | Met | Val | Ala | Thr | Val | Lys | Arg | Gln | Trp | Val | Leu | Glu | Glu | Thr | Ser | |
| | | | | 165 | | | | | 170 | | | | | 175 | | |

| gtt | atg | ctg | aaa | aac | att | tgg | gca | tac | gcc | caa | aag | att | ttc | aag | atc | 576 |
|---|---|---|---|---|---|---|---|---|---|---|---|---|---|---|---|---|
| Val | Met | Leu | Lys | Asn | Ile | Trp | Ala | Tyr | Ala | Gln | Lys | Ile | Phe | Lys | Ile | |
| | | | 180 | | | | | 185 | | | | | 190 | | | |

| ctg | aag | cgt | caa | tgg | acc | cgt | gcg | acc | aag | atg | cag | gtg | atc | gcg | gat | 624 |
|---|---|---|---|---|---|---|---|---|---|---|---|---|---|---|---|---|
| Leu | Lys | Arg | Gln | Trp | Thr | Arg | Ala | Thr | Lys | Met | Gln | Val | Ile | Ala | Asp | |
| | | 195 | | | | | 200 | | | | | 205 | | | | |

| cgc | att | tgg | cac | cat | cac | cac | cac | cat | taa | | | | | | | 654 |
|---|---|---|---|---|---|---|---|---|---|---|---|---|---|---|---|---|
| Arg | Ile | Trp | His | His | His | His | His | His | | | | | | | | |
| | 210 | | | | | 215 | | | | | | | | | | |

<210> SEQ ID NO 54
<211> LENGTH: 849
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(846)

<400> SEQUENCE: 54

| atg | ttc | ccg | act | aaa | gac | gtt | gca | ctg | gcc | gac | cgc | atc | tgg | ggt | ccg | 48 |
|---|---|---|---|---|---|---|---|---|---|---|---|---|---|---|---|---|
| Met | Phe | Pro | Thr | Lys | Asp | Val | Ala | Leu | Ala | Asp | Arg | Ile | Trp | Gly | Pro | |
| 1 | | | | 5 | | | | | 10 | | | | | 15 | | |

| att | agc | ggt | cac | gtg | ctg | aaa | gca | gac | aac | caa | tac | cag | tat | gac | ccg | 96 |
|---|---|---|---|---|---|---|---|---|---|---|---|---|---|---|---|---|

```
                Ile Ser Gly His Val Leu Lys Ala Asp Asn Gln Tyr Gln Tyr Asp Pro
                            20                  25                  30 gtc gca gcg ctg ttt gcg gat cgc cag tgg caa gag ttc ttt tgg gac       144
Val Ala Ala Leu Phe Ala Asp Arg Gln Trp Gln Glu Phe Phe Trp Asp
                35                  40                  45 gca aat gac att tat gcc gat cgc atc tgg acg cct cgt gtg acc ggt       192
Ala Asn Asp Ile Tyr Ala Asp Arg Ile Trp Thr Pro Arg Val Thr Gly
            50                  55                  60 ggt ggc gca atg cgt aat atc tgg cag att aag gtg cgt gtg gat atg       240
Gly Gly Ala Met Arg Asn Ile Trp Gln Ile Lys Val Arg Val Asp Met
65                  70                  75                  80 gtg cgt aat cag tat att ccg agc atc aat gtt cac cat tat cgt aat       288
Val Arg Asn Gln Tyr Ile Pro Ser Ile Asn Val His His Tyr Arg Asn
                85                  90                  95 caa tac aag ctg ggt ggc gcc ctg cag gct aag gca gat cgt atc tgg       336
Gln Tyr Lys Leu Gly Gly Ala Leu Gln Ala Lys Ala Asp Arg Ile Trp
            100                 105                 110 cgt ccg cat gag cgt aac ggt ttt acg gtc cgt aac atc tgg gaa ttg       384
Arg Pro His Glu Arg Asn Gly Phe Thr Val Arg Asn Ile Trp Glu Leu
                115                 120                 125 cgt cgc aaa atg atg tat atg gcc gac aac att tgg gtt acc gag cat       432
Arg Arg Lys Met Met Tyr Met Ala Asp Asn Ile Trp Val Thr Glu His
            130                 135                 140 gac acc ctg ctg tac aaa cgc cag tgg aat ctg gtg ccg atg gtt gcg       480
Asp Thr Leu Leu Tyr Lys Arg Gln Trp Asn Leu Val Pro Met Val Ala
145                 150                 155                 160 acg gtt aag cgc caa tgg gtt ctg gaa gaa acc tct gtc atg ctg aag       528
Thr Val Lys Arg Gln Trp Val Leu Glu Glu Thr Ser Val Met Leu Lys
                165                 170                 175 aat atc tgg gcg tat gcc cag aag att ttc aag att ctg gcc gat cgt       576
Asn Ile Trp Ala Tyr Ala Gln Lys Ile Phe Lys Ile Leu Ala Asp Arg
            180                 185                 190 att tgg acg cgt gca acc aaa atg cag gtc att gcg gac cgt cag tgg       624
Ile Trp Thr Arg Ala Thr Lys Met Gln Val Ile Ala Asp Arg Gln Trp
                195                 200                 205 gcg cgt gtc tac gaa atc aag tgc cgc cgt aac cag tat tgt ccg agc       672
Ala Arg Val Tyr Glu Ile Lys Cys Arg Arg Asn Gln Tyr Cys Pro Ser
            210                 215                 220 cag gag ccg atg agc atc tac gtg tac aag cgt cag tgg tgt gag gac       720
Gln Glu Pro Met Ser Ile Tyr Val Tyr Lys Arg Gln Trp Cys Glu Asp
225                 230                 235                 240 gtt ccg agc ggc aag ctg cgc aat atc tgg tac gcc tac atc tac acc       768
Val Pro Ser Gly Lys Leu Arg Asn Ile Trp Tyr Ala Tyr Ile Tyr Thr
                245                 250                 255 acc tat ctg aaa cgt caa tgg caa gcg att cgt gaa acc gtt gag ctg       816
Thr Tyr Leu Lys Arg Gln Trp Gln Ala Ile Arg Glu Thr Val Glu Leu
            260                 265                 270 aaa aga caa tgg cac cac cat cac cac cat taa                           849
Lys Arg Gln Trp His His His His His His
                275                 280

<210> SEQ ID NO 55
<211> LENGTH: 390
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(387)
```

<400> SEQUENCE: 55

```
atg ttc cca act aaa gat gta gca ctc ggt cca att tcg cac ggt cac     48
Met Phe Pro Thr Lys Asp Val Ala Leu Gly Pro Ile Ser His Gly His
1               5                  10                  15 gtt ctg aag caa tac gat ccg gtt gcc gct ctg ttc cag gag ttc ttt     96
Val Leu Lys Gln Tyr Asp Pro Val Ala Ala Leu Phe Gln Glu Phe Phe
            20                  25                  30 tgg gac gca aac gac atc tac acg ccg cgt gtt acc ggc ggt ggc gcg    144
Trp Asp Ala Asn Asp Ile Tyr Thr Pro Arg Val Thr Gly Gly Gly Ala
        35                  40                  45 atg cag atc aag gtg cgc gtg gat atg gtg att ccg agc atc aat gtg    192
Met Gln Ile Lys Val Arg Val Asp Met Val Ile Pro Ser Ile Asn Val
    50                  55                  60 cac cac tat aaa ctg ggt ggt gcg ttg caa gcg aaa cgt ccg cat gag    240
His His Tyr Lys Leu Gly Gly Ala Leu Gln Ala Lys Arg Pro His Glu
65                  70                  75                  80 cgt aac ggc ttt acg gtt ctg gaa ctg cgt cgc aag atg atg tac atg    288
Arg Asn Gly Phe Thr Val Leu Glu Leu Arg Arg Lys Met Met Tyr Met
                85                  90                  95 gtg acc gag cat gac acc ctg ttg tat aat ctg gtc ccg atg gtt gcg    336
Val Thr Glu His Asp Thr Leu Leu Tyr Asn Leu Val Pro Met Val Ala
            100                 105                 110 acc gtc gtc ctg gaa gaa acg agc gtc atg ctg cac cac cat cat cat    384
Thr Val Val Leu Glu Glu Thr Ser Val Met Leu His His His His His
        115                 120                 125 cac taa                                                            390
His
```

<210> SEQ ID NO 56
<211> LENGTH: 447
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: CDS
<222> LOCATION: (1)..(444)

<400> SEQUENCE: 56

```
atg ttc cca act aaa gat gtc gca ctc gca gat ggt cca att tct cac     48
Met Phe Pro Thr Lys Asp Val Ala Leu Ala Asp Gly Pro Ile Ser His
1               5                  10                  15 ggt cac gta ttg aag gcg gat cag tac gac ccg gtt gcc gct ctg ttt     96
Gly His Val Leu Lys Ala Asp Gln Tyr Asp Pro Val Ala Ala Leu Phe
            20                  25                  30 gcc gat caa gag ttc ttc tgg gac gct aac gat atc tat gcc gac acc    144
Ala Asp Gln Glu Phe Phe Trp Asp Ala Asn Asp Ile Tyr Ala Asp Thr
        35                  40                  45 ccg cgt gtg acg ggt ggt ggc gca atg cgc caa atc aag gtc cgt gtt    192
Pro Arg Val Thr Gly Gly Gly Ala Met Arg Gln Ile Lys Val Arg Val
    50                  55                  60 gac atg gtt cgc att ccg agc atc aat gtt cat cat tat cgc aaa ctg    240
Asp Met Val Arg Ile Pro Ser Ile Asn Val His His Tyr Arg Lys Leu
65                  70                  75                  80 ggc ggt gcg ctg cag gcg aaa gcg gac cgt ccg cac gag cgt aat ggc    288
Gly Gly Ala Leu Gln Ala Lys Ala Asp Arg Pro His Glu Arg Asn Gly
                85                  90                  95 ttt acg gtg ttg cgc gag ctg cgt cgt aag atg atg tac atg gcg gac    336
Phe Thr Val Leu Arg Glu Leu Arg Arg Lys Met Met Tyr Met Ala Asp
            100                 105                 110
```

```
gtc acg gaa cac gat acc ctg ctg tac aaa aac ctg gtc ccg atg gtt       384
Val Thr Glu His Asp Thr Leu Leu Tyr Lys Asn Leu Val Pro Met Val
        115                 120                 125 gcg acc gtg aag gtg ctg gaa gaa acc agc gtg atg ctg aaa cat cac       432
Ala Thr Val Lys Val Leu Glu Glu Thr Ser Val Met Leu Lys His His
130                 135                 140 cat cac cac cat taa                                                   447
His His His His
145

<210> SEQ ID NO 57
<211> LENGTH: 696
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(693)

<400> SEQUENCE: 57 atg cat cca gtt ggt gaa gca gac tac ttt gaa tac cgt tcc tct tgc        48
Met His Pro Val Gly Glu Ala Asp Tyr Phe Glu Tyr Arg Ser Ser Cys
1               5                  10                  15 agc tcg tgt ccg ctg agc aag att gca gat cgt ccg atc ttc atc            96
Ser Ser Cys Pro Leu Ser Lys Ile Ala Asp Arg Pro Ile Phe Ile
            20                  25                  30 cgt cgt ttg aaa ttt ctg cgc ggt cgc gcg tac ggt ttg cgt ggt ctg       144
Arg Arg Leu Lys Phe Leu Arg Gly Arg Ala Tyr Gly Leu Arg Gly Leu
            35                  40                  45 tgc acc ctg gtg gcc atg ctg gcg gac gag gag tgt gat agc gag ctc       192
Cys Thr Leu Val Ala Met Leu Ala Asp Glu Glu Cys Asp Ser Glu Leu
50                  55                  60 gaa atc aaa cgc tat aag tgc ctg ggt ggc ctt ctg acg atg gtt gct       240
Glu Ile Lys Arg Tyr Lys Cys Leu Gly Gly Leu Leu Thr Met Val Ala
65                  70                  75                  80 gac cgt gcg aag ttt aag caa ctg ctg cgc gcc acc att ggt acg gca       288
Asp Arg Ala Lys Phe Lys Gln Leu Leu Arg Ala Thr Ile Gly Thr Ala
                85                  90                  95 atg tat aaa gct gac acc tat ggc ccg gtt ttc atg tgt ctg aag ctg       336
Met Tyr Lys Ala Asp Thr Tyr Gly Pro Val Phe Met Cys Leu Lys Leu
            100                 105                 110 ccg gag ccg ctg ccg cag ggt caa ctg acc gca tac aag att gag gac       384
Pro Glu Pro Leu Pro Gln Gly Gln Leu Thr Ala Tyr Lys Ile Glu Asp
        115                 120                 125 ccg ccg ttc aat agc ctg gcg gac gtg agc ttc att gaa ttt gtc ggc       432
Pro Pro Phe Asn Ser Leu Ala Asp Val Ser Phe Ile Glu Phe Val Gly
130                 135                 140 tgg aaa gaa gag aat ttg ctg gac ttc gtc cgc ttc atg ggc gtg aaa       480
Trp Lys Glu Glu Asn Leu Leu Asp Phe Val Arg Phe Met Gly Val Lys
145                 150                 155                 160 cag aac ggt gct ctg gca atc aac acg ttt cgt ccg tac ctg ttc tgg       528
Gln Asn Gly Ala Leu Ala Ile Asn Thr Phe Arg Pro Tyr Leu Phe Trp
                165                 170                 175 ctg gcg gcc att cgt gcg tat agc agc tgg atg tac agc tat gcc gat       576
Leu Ala Ala Ile Arg Ala Tyr Ser Ser Trp Met Tyr Ser Tyr Ala Asp
            180                 185                 190 cgt gtc cgc gcg tac acc tac tcc aaa gcg gat cgt cgt atc tac gat       624
Arg Val Arg Ala Tyr Thr Tyr Ser Lys Ala Asp Arg Arg Ile Tyr Asp
        195                 200                 205 ctg atc gag ctg cgt gtt gaa att acc ccg tat aaa cct act tgg gcg       672
Leu Ile Glu Leu Arg Val Glu Ile Thr Pro Tyr Lys Pro Thr Trp Ala
```

```
Leu Ile Glu Leu Arg Val Glu Ile Thr Pro Tyr Lys Pro Thr Trp Ala
    210                 215                 220 gat cac cat cat cac cac cac taa                                       696
Asp His His His His His His
225                 230

<210> SEQ ID NO 58
<211> LENGTH: 242
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Phe Pro Thr Lys Asp Val Ala Leu Ala Asp Arg Ile Trp Gly Pro Ile
1               5                   10                  15

Ser Gly His Val Leu Lys Ala Asp Asn Gln Tyr Gln Tyr Asp Pro Val
                20                  25                  30

Ala Ala Leu Phe Ala Asp Arg Gln Trp Gln Glu Phe Phe Trp Asp Ala
            35                  40                  45

Asn Asp Ile Tyr Ala Asp Arg Ile Trp Thr Pro Arg Val Thr Gly Gly
50                  55                  60

Gly Ala Met Arg Asn Ile Trp Gln Ile Lys Val Arg Val Asp Met Val
65                  70                  75                  80

Arg Asn Gln Tyr Ile Pro Ser Ile Asn Val His His Tyr Arg Asn Gln
                85                  90                  95

Tyr Lys Leu Gly Gly Ala Leu Gln Ala Lys Ala Asp Arg Ile Trp Arg
            100                 105                 110

Pro His Glu Arg Asn Gly Phe Thr Val Leu Arg Asn Ile Trp Glu Leu
        115                 120                 125

Arg Arg Lys Met Met Tyr Met Ala Asp Asn Ile Trp Val Thr Glu His
130                 135                 140

Asp Thr Leu Leu Tyr Lys Arg Gln Trp Asn Leu Val Pro Met Val Ala
145                 150                 155                 160

Thr Val Lys Arg Gln Trp Val Leu Glu Glu Thr Ser Val Met Leu Lys
                165                 170                 175

Asn Ile Trp Ala Tyr Ala Gln Lys Ile Phe Lys Ile Leu Ala Asp Arg
            180                 185                 190

Ile Trp Thr Arg Ala Thr Lys Met Gln Val Ile Ala Asp Arg Gln Trp
        195                 200                 205

Ala Arg Val Tyr Glu Ile Lys Cys Arg Arg Asn Lys Arg Gln Trp Gln
    210                 215                 220

Ala Ile Arg Glu Thr Val Glu Leu Lys Arg Gln Trp His His His
225                 230                 235                 240

His His

<210> SEQ ID NO 59
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
ccggtgttgc agcttcctac ttcaactcga gttgaagtag gaagctgcaa catttttt      57
```

-continued

<210> SEQ ID NO 60
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
ccggcccaac atttcttgga ccaaactcga gtttggtcca agaaatgttg ggtttttg      59

<210> SEQ ID NO 61
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 61

His His His His His His
1               5

<210> SEQ ID NO 62
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Phe Pro Thr Lys Asp Val Ala Leu Ala Asp Arg Ile Trp
1               5                   10

<210> SEQ ID NO 63
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Gly Pro Ile Ser Gly His Val Leu Lys Ala Asp Asn Gln Tyr
1               5                   10

<210> SEQ ID NO 64
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Gln Tyr Asp Pro Val Ala Ala Leu Phe Ala Asp Arg Gln Trp
1               5                   10

<210> SEQ ID NO 65
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

```
Gln Glu Phe Phe Trp Asp Ala Asn Asp Ile Tyr Ala Asp Arg Ile Trp
1               5                   10                  15

<210> SEQ ID NO 66
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Thr Pro Arg Val Thr Gly Gly Gly Ala Met Arg Asn Ile Trp
1               5                   10

<210> SEQ ID NO 67
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Gln Ile Lys Val Arg Val Asp Met Val Arg Asn Gln Tyr
1               5                   10

<210> SEQ ID NO 68
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Ile Pro Ser Ile Asn Val His His Tyr Arg Asn Gln Tyr
1               5                   10

<210> SEQ ID NO 69
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Lys Leu Gly Gly Ala Leu Gln Ala Lys Ala Asp Arg Ile Trp
1               5                   10

<210> SEQ ID NO 70
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Arg Pro His Glu Arg Asn Gly Phe Thr Val Arg Asn Ile Trp
1               5                   10

<210> SEQ ID NO 71
<211> LENGTH: 14
<212> TYPE: PRT
<213> ORGANISM: Artificial Sequence
<220> FEATURE:
```

-continued

<223> OTHER INFORMATION: Description of Artificial Sequence: Synthetic
      peptide

<400> SEQUENCE: 71

Glu Leu Arg Arg Lys Met Met Tyr Met Ala Asp Asn Ile Trp
1               5                   10

<210> SEQ ID NO 72
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Val Thr Glu His Asp Thr Leu Leu Tyr Lys Arg Gln Trp
1               5                   10

<210> SEQ ID NO 73
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Asn Leu Val Pro Met Val Ala Thr Val Lys Arg Gln Trp
1               5                   10

<210> SEQ ID NO 74
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Val Leu Glu Glu Thr Ser Val Met Leu Lys Asn Ile Trp
1               5                   10

<210> SEQ ID NO 75
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Phe Pro Thr Lys Asp Val Ala Leu Gly Pro Ile Ser Gly His Val Leu
1               5                   10                  15

Lys Gln Tyr Asp Pro Val Ala Ala Leu Phe Gln Glu Phe Phe Trp Asp
            20                  25                  30

Ala Asn Asp Ile Tyr Thr Pro Arg Val Thr Gly Gly Gly Ala Met Gln
        35                  40                  45

Ile Lys Val Arg Val Asp Met Val Ile Pro Ser Ile Asn Val His His
    50                  55                  60

Tyr Lys Leu Gly Gly Ala Leu Gln Ala Lys Arg Pro His Glu Arg Asn
65                  70                  75                  80

Gly Phe Thr Val Leu Glu Leu Arg Arg Lys Met Met Tyr Met Val Thr
                85                  90                  95

Glu His Asp Thr Leu Leu Tyr Asn Leu Val Pro Met Val Ala Thr Val
            100                 105                 110

Val Leu Glu Glu Thr Ser Val Met His His His His His
        115                 120                 125

<210> SEQ ID NO 76
<211> LENGTH: 146
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Phe Pro Thr Lys Asp Val Ala Leu Ala Asp Gly Pro Ile Ser Gly His
1               5                   10                  15

Val Leu Lys Ala Asp Gln Tyr Asp Pro Val Ala Ala Leu Phe Ala Asp
            20                  25                  30

Gln Glu Phe Phe Trp Asp Ala Asn Asp Ile Tyr Ala Asp Thr Pro Arg
        35                  40                  45

Val Thr Gly Gly Gly Ala Met Arg Gln Ile Lys Val Arg Val Asp Met
50                  55                  60

Val Arg Ile Pro Ser Ile Asn Val His His Tyr Arg Lys Leu Gly Gly
65                  70                  75                  80

Ala Leu Gln Ala Lys Ala Asp Arg Pro His Glu Arg Asn Gly Phe Thr
            85                  90                  95

Val Leu Arg Glu Leu Arg Arg Lys Met Met Tyr Met Ala Asp Val Thr
        100                 105                 110

Glu His Asp Thr Leu Leu Tyr Lys Asn Leu Val Pro Met Val Ala Thr
    115                 120                 125

Val Lys Val Leu Glu Glu Thr Ser Val Met Leu Lys His His His His
    130                 135                 140

His His
145

<210> SEQ ID NO 77
<211> LENGTH: 230
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

His Pro Val Gly Glu Ala Asp Tyr Phe Glu Tyr Arg Ser Ser Cys Ser
1               5                   10                  15

Ser Cys Pro Leu Ser Lys Ile Ala Asp Arg Pro Pro Ile Phe Ile Arg
            20                  25                  30

Arg Leu Lys Phe Leu Arg Gly Arg Ala Tyr Gly Leu Arg Gly Leu Cys
        35                  40                  45

Thr Leu Val Ala Met Leu Ala Asp Glu Glu Cys Asp Ser Glu Leu Glu
50                  55                  60

Ile Lys Arg Tyr Lys Cys Leu Gly Gly Leu Leu Thr Met Val Ala Asp
65                  70                  75                  80

Arg Ala Lys Phe Lys Gln Leu Leu Arg Ala Thr Ile Gly Thr Ala Met
            85                  90                  95

Tyr Lys Ala Asp Thr Tyr Gly Pro Val Phe Met Cys Leu Lys Leu Pro
        100                 105                 110

-continued

```
Glu Pro Leu Pro Gln Gly Gln Leu Thr Ala Tyr Lys Ile Glu Asp Pro
            115             120             125

Pro Phe Asn Ser Leu Ala Asp Val Ser Phe Ile Glu Phe Val Gly Trp
        130             135             140

Lys Glu Glu Asn Leu Leu Asp Phe Val Arg Phe Met Gly Val Lys Gln
145             150             155             160

Asn Gly Ala Leu Ala Ile Asn Thr Phe Arg Pro Tyr Leu Phe Trp Leu
                165             170             175

Ala Ala Ile Arg Ala Tyr Ser Ser Trp Met Tyr Ser Tyr Ala Asp Arg
            180             185             190

Val Arg Ala Tyr Thr Tyr Ser Lys Ala Asp Arg Arg Ile Tyr Asp Leu
        195             200             205

Ile Glu Leu Arg Val Glu Ile Thr Pro Tyr Lys Pro Thr Trp Ala Asp
        210             215             220

His His His His His His
225             230
```

HUMAN HERPESVIRUS IMMUNOTHERAPY

CROSS REFERENCE TO RELATED APPLICATIONS AND CLAIM TO PRIORITY

This Application is a national application of International Application No. PCT/AU2013/001216 (filed on Oct. 21, 2013), which claims priority to Australian Patent Application No. 2012904604 (filed on Oct. 19, 2012), which applications are herein incorporated by reference in their entireties and to which priority is claimed.

SEQUENCE LISTING

The instant application contains a Sequence Listing which has been submitted electronically in ASCII format and is hereby incorporated by reference in its entirety. Said ASCII copy, created on Aug. 25, 2016, is named QAH-00701_SL.txt and is 57,698 bytes in size.

TECHNICAL FIELD

THIS INVENTION relates to human herpesvirus immunotherapy. In particular, the invention relates to a recombinant protein which includes a plurality of cytotoxic T cell epitopes derived from multiple human cytomegalovirus (CMV) or Epstein-Barr virus (EBV) antigens, which, when used in immunotherapy are capable of eliciting a cytotoxic T-lymphocyte immune response, without being limited thereto.

BACKGROUND

Epstein-Barr virus occurs with an extremely high incidence with over 90% of adults showing some sign of exposure. EBV also persists subsists as a lifelong latent infection and may be asymptomatic. However, EBV can result in mononucleosis, also known as glandular fever causing significant morbidity in some individuals. EBV may be associated with several autoimmune diseases such as lupus, rheumatoid arthritis and multiple sclerosis. Importantly, EBV is known to be associated with a number of cancers such as nasopharyngeal carcinoma (NPC), Burkitt's lymphoma and Hodgkin lymphoma. NPC is a cancer that is common in Chinese and South-East Asian populations (rare in most other populations). Patients often present with mid (Stage III) or advanced stage (Stage IV) disease as symptoms are poorly recognised at earlier stages. The first line of treatment for patients when diagnosed with NPC is radiotherapy and chemotherapy with limited options for surgery. Radio/chemo is effective for many patients but approximately 20% will either respond inadequately or relapse and this group have a poor prognosis. Patients that present with stage III and IV tumours have a 5 year overall survival of only 50 to 60% (lower for stage IV patients alone). The most common forms of NPC are associated with EBV making these tumours amendable to immunotherapy by targeting and killing EBV infected tumour cells.

Primary CMV in healthy individuals is generally asymptomatic, establishing a latent state with occasional reactivation and shedding from mucosal surfaces. In some cases primary CMV infection is accompanied with clinical symptoms of a mononucleosis-like illness, similar to that caused by Epstein-Barr virus. There are two important clinical settings where CMV causes significant morbidity and mortality. These include congenital primary infection and primary or reactivation of virus in immunosuppressed adults. In the congenital setting, CMV is the leading cause of mental retardation and other abnormalities such as deafness in children and this impact has been emphasized by its categorization by the Institute of Medicine as a Level I vaccine candidate [i.e. most favourable impact—saves both money and quality-adjusted life years (QALYs) (Arvin, Fast et al. 2004). CMV-associated complications in immunocompromised individuals such as HIV-infected individuals is often seen in patients with $CD4^+$ T cell counts below 50/µl (Palella, Delaney et al. 1998; Salmon-Ceron, Mazeron et al. 2000). In addition, the impact of CMV in transplant patients, including both solid organ transplant and allogeneic hematopoietic stem cell transplant recipients, is well recognized.

Primary exposure to CMV results in the induction of a strong primary immune response, which is maintained as a long-term memory response, and serves to restrict viral replication following reactivation. There is now firm evidence that both humoral and cellular immune responses play a crucial role in controlling CMV infection. Studies carried out in murine CMV models provided the initial evidence on the importance of T cell immunity, where a loss of T cell function was co-incident with increased reactivation and dissemination of viral infection (Reddehase, Weiland et al. 1985; Mutter, Reddehase et al. 1988). Furthermore, the reconstitution of virus-specific T cell immunity was coincident with recovery from acute viral infection. Subsequent studies in humans under different clinical settings have further emphasized the role of virus-specific T cells. These studies showed that allogeneic stem cell transplant patients, who had insufficient anti-viral T cell immunity, demonstrated an increased risk of developing CMV-associated complications. Convincing evidence for the role of cellular immunity in the control of CMV-disease came from studies where adoptive transfer of donor derived CMV-specific $CD8^+$ T cells not only restored antigen-specific cellular immunity, but also prevented CMV-associated clinical complications in allogeneic stem cell transplant patients (Riddell, Watanabe et al. 1992; Walter, Greenberg et al. 1995).

Taking these studies into consideration, a variety of CMV vaccines have been evaluated in preclinical and clinical trials.

These CMV vaccine strategies have assessed glycoprotein B (gB), pp65 and IE-1 as potential targets and they have been delivered by numerous delivery platforms, including the attenuated CMV Towne strain (Jacobson, Sinclair et al. 2006), recombinant viral vectors encoding full length antigens and epitopes (Bernstein, Reap et al. 2009; Zhong and Khanna 2009), DNA (Wloch, Smith et al. 2008), dense body (Frankenberg, Pepperl-Klindworth et al. 2002), and subunit (Drulak, Malinoski et al. 2000) vaccines. However, none of these approaches have shown convincing clinical efficacy and have not entered into clinical practice.

Typically, it has been proposed that in order to elicit a protective, $CD8^+$ cytotoxic T cell response, viral antigens must be delivered in nucleic acid form (e.g using a viral vector delivery system) rather than as an exogenously-delivered proteins so that the expressed protein is properly processed and presented to T cells (Koup & Douek, 2012). The majority of these vaccine delivery platforms, in particular live-attenuated vaccines and viral vector based vaccines, have raised several regulatory concerns such as perceived long-term theoretical health risks (Liu; Soderberg-Naucler 2006; Anderson and Schneider 2007).

SUMMARY

The present invention addresses a need for the development of herpesvirus immunotherapy using a safe delivery technology. The invention is directed towards reducing the risk of CMV associated injury to the developing fetus, and immunologically compromised individuals such as recipients of solid organ and hematopoietic stem cell transplants and patients with advanced HIV disease. The invention is also directed toward treating the symptoms of an existing EBV infection, such as in immunologically compromised transplant patients or in the prevention or treatment of EBV-associated cancers such as nasopharyngeal carcinoma (NPC).

The invention has surprisingly arisen from the discovery that contrary to past assumptions, an exogenous a polyepitope protein administered to an individual may elicit a protective, $CD8^+$ cytolytic T cell response.

Accordingly, the invention is broadly directed to an isolated polyepitope protein comprising a plurality of human herpesvirus cytotoxic T cell (CTL) epitopes that is capable of eliciting a cytotoxic T cell response.

In a first aspect, an isolated protein comprises respective amino acid sequences of each of a plurality of CTL epitopes from two or more different herpesvirus antigens and which further comprises an intervening amino acid or amino acid sequence between at least two of said CTL epitopes comprising proteasome liberation amino acids or amino acid sequences and, optionally, Transporter Associated with Antigen Processing (TAP) recognition motifs, wherein the isolated protein is capable of eliciting a cytotoxic T-lymphocyte immune response upon administration to an animal as an exogenous protein.

Suitably, the isolated protein comprises epitopes are selected to provide broad coverage of the human population. These include HLA class I specificities HLA-A1, -A2, -A3, -A11, -A23, -A24, -A26, -A29, -A30, -B7, -B8, -B27, -B35, -B38, -B40, -B41, -B44, -B51, -B57 and -B58.

Suitably, said plurality of epitopes comprises less than twenty (20) epitopes in total.

In one embodiment, the herpesvirus is CMV. Preferably, the CTL epitopes are from CMV antigens selected from the group consisting of: pp50, pp65, pp150 and IE-1.

In a preferred embodiment, the isolated protein comprises a plurality of CTL epitopes selected from Table 1 (SEQ ID NOS: 1-21) In a particular embodiment, the isolated protein comprises a plurality of CTL epitopes selected from Table 2 (bolded sequences disclosed as SEQ ID NOS: 1-13 and full-length sequences disclosed as SEQ ID NOS 62-74, respectively, in order of appearance).

In a preferred embodiment, at least one of the CTL epitopes comprises the amino acid sequence VTEHDTLLY (SEQ ID NO:11).

In another embodiment, the herpesvirus is EBV.

Preferably, the CTL epitopes are from EBV antigens selected from the group consisting of: BMLF1, LMP2a, BRLF1, LMP2, EBNA3A, BZLF1, EBNA3C, EBNA1 and EBNA3B.

In a preferred embodiment, the isolated protein comprises a plurality of CTL epitopes selected from and Table 3 (SEQ ID NOS:22-41).

It will also be appreciated that the isolated protein may comprise CTL epitopes from the same or different herpesvirus (e.g CMV and/or EBV).

The isolated protein may further comprise intervening amino acids or amino acid sequences.

In a preferred embodiment, the intervening amino acids or amino acid sequences are proteasome liberation amino acids or amino acid sequences.

In an optional embodiment, the intervening amino acids or amino acid sequence are Transporter Associated with Antigen Processing (TAP) recognition motifs.

In a second aspect, the invention provides an isolated nucleic acid encoding the isolated protein of the first aspect.

In a third aspect, the invention provides a genetic construct comprising the isolated nucleic acid of the second aspect.

Preferably, the genetic construct is an expression construct wherein said isolated nucleic acid of the second aspect is operably linked to one or more regulatory sequences present in an expression vector.

In an embodiment, the expression construct comprises an expression vector suitable for production of the isolated protein in vitro as a recombinant protein for subsequent purification.

In a fourth aspect, the invention provides a host cell comprising the expression construct of the third aspect.

In another embodiment, the host cell has been transfected, transformed or otherwise introduced with the expression construct in vitro, for the purpose of subsequent purification of the isolated protein of the first aspect.

In a fifth aspect, the invention provides a method of producing the isolated protein of the first aspect, said method including the steps of expressing the isolated protein in the host cell of the fourth aspect and at least partly purifying the isolated proteins under conditions that maintain the isolated protein in a substantially non-aggregated form.

In a sixth aspect, the invention provides an isolated protein produced according to the method of the fifth aspect.

In a seventh aspect, the present invention provides a pharmaceutical composition comprising the isolated protein of the first or sixth aspects or the genetic construct of the third aspect, and a pharmaceutically-acceptable carrier, diluent or excipient.

Preferably, the pharmaceutical composition is an immunogenic composition suitable for use in the prophylactic or therapeutic treatment of a disease or condition associated with CMV and/or EBV infection in an animal.

More preferably, the immunotherapeutic composition is a vaccine for eliciting a protective immune response against CMV and/or EBV. In this regard, it will be appreciated that the pharmaceutical composition may comprise separate isolated proteins respectively comprising CMV and EBV CTL epitopes or may comprise a single isolated protein comprising both EBV and CMV epitopes.

In one particular embodiment, the pharmaceutical composition further comprises one or more immunostimulatory molecules or adjuvants.

Suitably, the immunostimulatory molecule or adjuvant comprises one or more toll-like receptor (TLR) agonists.

Preferably, the TLR agonists include a TLR4 agonist and/or a TLR9 agonist. Preferred adjuvants include Monophosphoryl lipid (MPL) and/or immunostimulatory DNA such as CpG ODN1826, CpG ODN2006, CpG ODN2216 and/or CpG ODN2336, although without limitation thereto.

In an eighth aspect, the invention provides a method of prophylactically or therapeutically treating a herpesvirus infection in an animal including the step of administering to the animal the isolated protein of the first or sixth aspects, or the pharmaceutical composition of the seventh aspect, to thereby prophylactically or therapeutically treat the herpesvirus infection in the animal.

In particular embodiments, the herpesvirus is CMV or EBV.

In a ninth aspect, the invention provides a method of inducing a cytotoxic T-lymphocyte (CTL) immune response in an animal including the step of administering to the animal the isolated protein of the first or sixth aspects or the pharmaceutical composition of the seventh aspect, to thereby induce or elicit a cytotoxic T-lymphocyte (CTL) immune response in said animal.

In a tenth aspect, the invention provides a method of expanding herpesvirus-specific CTLs for adoptive immunotherapy, including the steps of:
(i) contacting one or more cells isolated from an animal with the isolated protein of the first or sixth aspects; and
(ii) culturing said one or more cells to thereby expand herpesvirus-specific CTLs from said one or more cells.

In particular embodiments, the herpesvirus is CMV or EBV.

In an eleventh aspect, the invention provides a method of adoptive immunotherapy including the step of administering said herpesvirus-specific CTLs produced at step (ii) of the tenth aspect to an animal to thereby prophylactically or therapeutically treat a herpesvirus infection of said animal.

In particular embodiments, the herpesvirus is CMV or EBV.

In a twelfth aspect, the invention provides the isolated protein of the first or sixth aspects, or the genetic construct of the third aspect for use in prophylactically or therapeutically treating a herpesvirus infection in an animal.

In particular embodiments, the herpesvirus is CMV or EBV.

Preferably, according to the aforementioned aspects the animal is a mammal.

More preferably, the animal is a human.

BRIEF DESCRIPTION OF THE FIGURES

In order that the present invention may be more readily understood and placed into practical effect, preferred embodiments of the invention will be described, by way of example only, with reference to the accompanying figures.

FIG. 14: In vitro expansion of EBV-specific CD8+ T cells from healthy sero-positive donors using EBVpoly protein. PBMC from a panel of healthy donors (n=8) were stimulated with or without EBVpoly protein in vitro, cultured for 14 days in the presence of IL-2 and then cells were assessed for the expansion of EBV-specific T cells using ICS assays. Bar graphs represent the comparative percentage of expanded EBV-specific CD8+ T cells from each donor following stimulation with EBVpoly protein.

FIG. 15: Amino acid sequences of CMV and EBV polyepitope proteins and nucleotide sequences of encoding nucleic acids. A: CMV polytope is SEQ ID NO:42; nucleotide sequence encoding CMV polytope is SEQ ID NO:50; B: CMV polytope is SEQ ID NO:43; nucleotide sequence encoding CMV polytope is SEQ ID NO:51; C: CMV polytope is SEQ ID NO:44; nucleotide sequence encoding CMV polytope is SEQ ID NO:52; D: CMV polytope is SEQ ID NO:45; nucleotide sequence encoding CMV polytope is SEQ ID NO:53; E: CMV polytope is SEQ ID NO:46; nucleotide sequence encoding CMV polytope is SEQ ID NO:54; F: CMV polytope is SEQ ID NO:47; nucleotide sequence encoding CMV polytope is SEQ ID NO:55; G: CMV polytope is SEQ ID NO:48; nucleotide sequence encoding CMV polytope is SEQ ID NO:56; H: EBV polytope is SEQ ID NO:49; nucleotide sequence encoding EBV polytope is SEQ ID NO:57.

DETAILED DESCRIPTION

Figure 1:
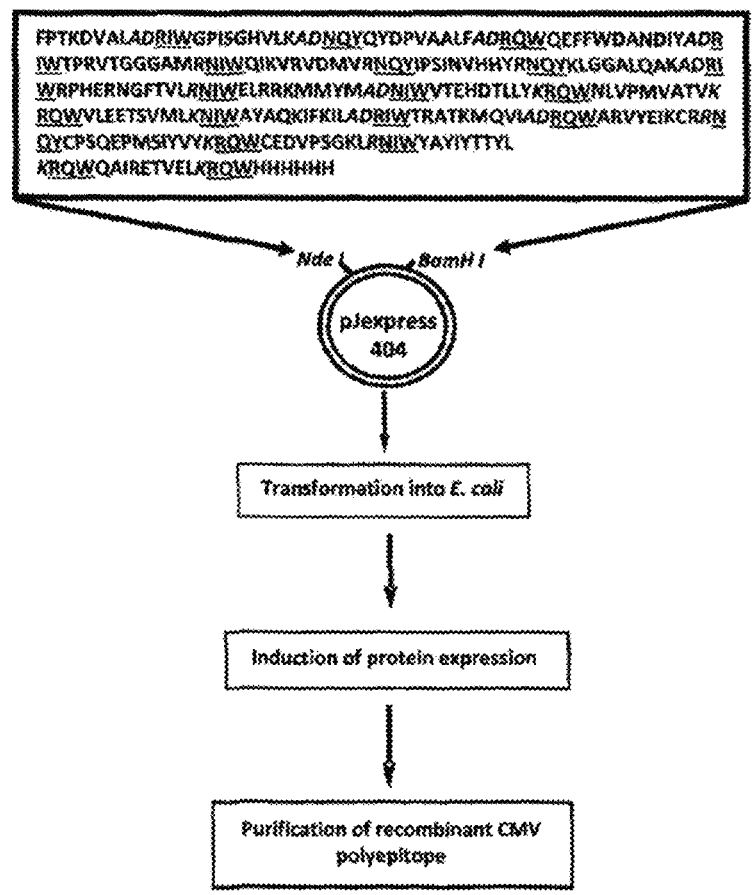
FIG. 1: Illustration of the design of the CMV polyepitope (SEQ ID NO: 58) and downstream processing. The design of the CMV polyepitope 20mer encoding sequence is shown as an example. The isolated protein comprises a plurality of CTL epitopes from Table 1 (SEQ ID NOS: 1-13 and 15-21). Individual epitope amino acid sequences are shown in bold; grey, Italicised letters following the epitope sequence represent the amino acid residues for processing of the CMV polyepitope protein by the proteasome and the underlined amino acid sequences represent the motifs for TAP (referred to as CMVpoly-PTL). The DNA sequence encoding the CMV polyepitope protein was synthetically made, cloned into an *E. coli* inducible plasmid, pJexpress 404, and transformed into *E. coli* to carry out protein expression and purification.

The present invention is at least partly predicated on the unexpected discovery that an isolated protein comprising a plurality of herpesvirus epitopes such as CMV and/or EBV epitopes administered to an individual as an exogenous protein may elicit a protective, CD8+ cytotoxic T cell response. It appears that once administered, the exogenous protein is processed by a novel, cellular TAP-independent, proteasome and autophagy dependent pathway which is assisted by the inclusion of proteasome liberation amino acids in the exogenous protein. This results in HLA Class I-dependent presentation of the processed CMVepitopes to CD8+ cytotoxic T cells. This unexpected discovery may also be at least partly related to an improved recombinant protein purification method that avoids or reduces aggregation of the recombinant protein. A difficulty typically encountered with such proteins is that T cell epitopes are hydrophobic and/or contain several hydrophobic amino acids, which means that the protein is susceptible to hydrophobic aggregation, which may compromise the ability to deliver the recombinant protein in a manner which enables the CTL epitopes of the protein to be processed in the manner described above. This is exacerbated by the use of intervening TAP recognition motifs that are typically hydrophobic. The improved recombinant polyepitope protein purification method described herein avoids or at least reduces aggregation of the polytope protein, thereby allowing efficient delivery and processing of the polyepitope protein. The inventors have also discovered that production, purification and immunization with the isolated polyepitope protein is optimized by using less than twenty (20) CTL epitopes in the isolated protein. Further to the above, the invention utilizes particular immunogenic components such as toll-like receptor (TLR) agonists that enhance the immunogenicity of the isolated protein.

Throughout this specification, unless otherwise indicated, "comprise", "comprises" and "comprising" are used inclusively rather than exclusively, so that a stated integer or group of integers may include one or more other non-stated integers or groups of integers.

It will also be appreciated that the indefinite articles "a" and "an" are not to be read as singular indefinite articles or as otherwise excluding more than one or more than a single subject to which the indefinite article refers. For example, "a" protein includes one protein, one or more proteins or a plurality of proteins.

In a first aspect, an isolated protein comprises respective amino acid sequences of each of a plurality of CTL epitopes from two or more different herpesvirus antigens and which further comprises an intervening amino acid or amino acid sequence between at least two of said CTL epitopes comprising proteasome liberation amino acids or amino acid sequences and, optionally, Transporter Associated with Antigen Processing (TAP) recognition motifs, wherein the isolated protein is capable of eliciting a cytotoxic T-lymphocyte immune response upon administration to an animal as an exogenous protein.

By "isolated" is meant material that has been removed from its natural state or otherwise been subjected to human manipulation. Isolated material may be substantially or essentially free from components that normally accompany it in its natural state, or may be manipulated so as to be in an artificial state together with components that normally accompany it in its natural state.

By "protein" is meant an amino acid polymer comprising natural and/or non-natural amino acids, D- or L-amino acids as are well known in the art.

A "peptide" is a protein having no more than fifty (50) amino acids.

A "polypeptide" is a protein having more than fifty (50) amino acids.

As used herein, the isolated protein may be referred to as an isolated polyepitope or polytope protein. For example, an isolated "CMV polyepitope", "EBV polyepitope" or an isolated "CMV polyepitope protein" or "EBV polyepitope protein".

In the context of the present invention, an "exogenous" protein or polyepitope protein is a protein produced externally to the animal to which it is subsequently administered. Effectively, the exogenous protein is administered or administrable to the animal, rather than being produced or expressed by the animal in situ (e.g. by cells or tissues of the animal) following delivery of a nucleic acid or genetic construct encoding the protein to the animal. A preferred exogenous protein is a recombinant protein produced in an isolated host cell ex vivo, such as a bacterial host cell.

As used herein, a "CTL epitope" is a peptide, or an amino acid sequence of the peptide, that is capable of stimulating or activating a cytotoxic T lymphocyte to recognize a target cell presenting the epitope in the context of the appropriate MHC Class I molecule. Recognition of the target cell may include or result in cytokine production (e.g., IFN-γ, IL-2, MIP-1β and/or TNF), changes in cell surface marker expression (e.g. CD107a) and/or lysis and/or killing of the target cell.

Typically, although not exclusively, a CTL epitope comprises 7, 8, 9, 10, 11, 12, 13, 14 or 15 contiguous amino acids of, derived from, obtained from or based on a corresponding herpesvirus antigen.

The polyepitope protein preferably comprises a plurality of CMV and/or EBV CTL epitopes derived from a plurality of different CMV protein antigens. Preferably, the epitopes are of CMV antigens selected from the group consisting of: pp50, pp65, pp150 and IE-1 and/or EBV antigens selected from the group consisting of: BMLF1, LMP2a, BRLF1, LMP2, EBNA3A, BZLF1, EBNA3C, EBNA1 and EBNA3B.

Suitably, the CMV and/or EBV polyepitope protein comprises CTL epitopes selected to provide broad coverage of a population. In humans, these include HLA class I specificities HLA-A1, -A2, -A3, -A11, -A23, -A24, -A26, -A29, -A30, -B7, -B8, -B27, -B35, -B38, -B40, -B41, -B44, -B51, -B57, -B58 and -cw6.

In certain embodiments, the CTL epitopes are restricted to the HLA class I specificities shown in Table 1 or Table 2.

In a particular embodiment, the CMV polyepitope protein comprises a plurality of HLA class I restricted CTL epitopes selected from Table 1 (SEQ ID NOS: 1-21) or Table 3 (SEQ ID NOs: 22-41).

In a particular embodiment, the EBV polyepitope protein comprises a plurality of HLA class I restricted CTL epitopes selected from Table 3 (SEQ ID NOs: 22-41).

It will also be appreciated that the invention contemplates inclusion of CTL epitopes derived from the same or different herpesvirus (e.g CMV and/or EBV). Accordingly, one embodiment of the isolated protein comprises CTL epitopes from both CMV and EBV antigens.

Suitably, said plurality of epitopes comprises less than twenty (20) epitopes in total.

In a particular embodiment, said plurality of epitopes comprises ten (10) to fifteen (15) epitopes in total.

One particular embodiment provides an isolated protein comprising thirteen (13) CMV CTL epitopes, such as shown in Table 2. In a preferred embodiment, at least one of the epitopes comprises the CMV amino acid sequence VTEHDTLLY (SEQ ID NO:11).

The full length, contiguous polyepitope protein comprises the amino acid sequence set forth in SEQ ID NOs:42-48 and shown in FIG. 15A-G.

It will also be appreciated that other CMV CTL epitopes may be used, such as described in International Publication WO 03/000720.

One particular embodiment provides an isolated protein comprising thirteen (13) EBV CTL epitopes, such as shown in Table 3. The full length, contiguous EBV polyepitope protein comprises the amino acid sequence set forth in SEQ ID NO:49 as shown in FIG. 15H.

It will also be further appreciated that other EBV CTL epitopes may be used such as described in International Publications WO 95/024925; WO 97/45444; WO 99/02550 and WO 04/041849.

The isolated polyepitope protein may further comprise one or a plurality of HLA Class II restricted CTL epitopes.

It will be appreciated by a skilled person that epitope selected may be tailored to fit any population, race or other group of individuals.

Other criteria for inclusion within the herpesvirus polyepitope include those (i) having minimal or no sequence variants; (ii) selected from HLAs having minimal subtypes; (iii) having a high frequency of CTL responses in healthy seropositives; and (iv) based on epitope hydrophobic properties, wherein the novel sequential order of individual epitopes are arranged such that hydrophobicity is uniform distributed along the length of the polyepitope to assist inter cellular mobility.

Furthermore, it will be appreciated that the particular number and order of the constituent CTL epitopes may readily be altered while retaining broad HLA Class I-restricted immunogenicity.

In addition to the CTL epitopes, the isolated protein may further comprise intervening amino acids or amino acid sequences. Intervening amino acids or amino acid sequences may be present between at least two of the CTL epitope amino acid sequences, or between each adjacent CTL epitope amino acid sequence.

Suitably, the intervening amino acids or amino acid sequences are positioned or located relative to the CTL epitope amino acid sequences to enable proteasomal processing and for transporting the proteasome-generated, individual CTL epitope peptides into the endoplasmic reticulum (ER) for subsequent presentation with HLA-I molecules.

In one embodiment, the intervening amino acids or amino acid sequences are proteasome liberation amino acids or amino acid sequences.

Non-limiting examples of proteasome liberation amino acids or amino acid sequences are or comprise AD, K or R.

In an optional embodiment, the intervening amino acids or amino acid sequence are TAP recognition motifs. Typically, TAP recognition motifs may conform to the following formula: $(R/N:I/Q:W/Y)_n$ where n is any integer $\geq 1$.

Non-limiting examples of TAP recognition motifs include RIW, RQW, NIW and NQY.

In a preferred form, CMV and/or EBV CTL epitopes are linked or joined by the proteasome liberation amino acid sequence and, optionally, the TAP recognition motif at the carboxyl terminus of each epitope.

Non-limiting examples of TAP recognition motifs, proteasome liberation amino acids and their positioning relative to the CTL epitope amino acid sequences are shown in Table 1 and Table 2 and are also present in the polyepitope amino acid sequences shown in FIG. 1 (SEQ ID NO:58) and FIGS. 15A-H (SEQ ID NOS:42-49).

Surprisingly, once administered the exogenous protein comprising the intervening amino acids or amino acid sequences is processed by a novel, cellular TAP-independent, proteasome and autophagy dependent pathway. This results in HLA Class I-dependent presentation of the processed CMVepitopes to $CD8^+$ cytotoxic T cells.

Therefore, the TAP amino acid sequences may be omitted or absent, in which case it is proposed or expected that the TAP-independent pathway could sufficiently process the isolated protein to enable presentation with HLA-I molecules.

In another embodiment, the isolated polyepitope protein may further comprise one or a plurality of $CD4^+$ helper T cell epitopes.

It will also be appreciated that the isolated protein described herein may be subjected to further modifications, variations and/or derivitizations without departing from the inventive concept.

Variations in amino acid sequence may be the result of naturally occurring sequence variation in a herpesvirus polyepitope protein.

It is well understood in the art that some amino acids may be changed to others with broadly similar properties without changing the nature of the activity of the isolated protein (conservative substitutions).

Typically, conservative substitutions are made so that amino acid properties such as charge, hydrophilicity, hydrophobicity and/or side chain size or "bulkiness" are retained or at least minimally altered.

Introduction of amino acid substitutions may be readily achieved during peptide synthesis or by mutagenesis of an encoding nucleic acid.

Non-limiting examples of nucleic acid mutagenesis methods are provided in Chapter 9 of CURRENT PROTOCOLS IN MOLECULAR BIOLOGY, Ausubel et al., supra, Stemmer, 1994, Proc. Natl. Acad. Sci. USA 91 10747, Shafikhani et al., 1997, Biotechniques 23 304, Jenkins et al., 1995, EMBO J. 14 4276-4287 and Zaccolo et al., 1996, J. Mol. Biol. 255 58 and kits such as QuickChange™ Site-Directed Mutagenesis Kit (Stratagene) and the Diversify™ random mutagenesis kit (Clontech).

Generally, the invention contemplates protein variants having at least 75%, preferably at least 80%, more preferably at least 85% or even more preferably at least 90, 91, 92, 93, 94, 95, 96, 97, 98 or 99% amino acid sequence identity with the constituent CTL epitope sequences, individually or in combination. In other embodiments, this may include conservative variations or substitutions of one (1), two (2) or three (3) amino acid residues of a CTL epitope.

The term "sequence identity" is used herein in its broadest sense to include the number of exact amino acid matches having regard to an appropriate alignment using a standard algorithm, having regard to the extent that sequences are identical over a window of comparison. Sequence identity may be determined using computer algorithms such as GAP, BESTFIT, FASTA and the BLAST family of programs as for example disclosed by Altschul et al., 1997, Nucl. Acids Res. 25 3389. A detailed discussion of sequence analysis can be found in Unit 19.3 of CURRENT PROTOCOLS IN MOLECULAR BIOLOGY Eds. Ausubel et al. (John Wiley & Sons Inc NY, 1995-1999).

As used herein, "derivative" proteins of the invention have been altered, for example by conjugation, fusion with additional protein sequences, by complexing with other chemical moieties or by post-translational modification techniques as would be understood in the art.

"Additions" of amino acids may include fusion with amino acid sequences of other proteins such as "fusion partners" or "epitope tags" which assist recombinant protein purification and/or identification.

Well known examples of fusion partners include, but are not limited to, glutathione-S-transferase (GST), Fc portion of human IgG, maltose binding protein (MBP) and hexahistidine ($HIS_6$ (SEQ ID NO: 61)), which are particularly useful for isolation of the fusion polypeptide by affinity chromatography. For the purposes of fusion protein purification by affinity chromatography, relevant matrices for affinity chromatography are glutathione-, amylose-, and nickel- or cobalt-conjugated resins respectively. Many such matrices are available in "kit" form, such as the QIAexpress™ system (Qiagen) useful with ($HIS_6$ (SEQ ID NO: 61)) fusion partners and the Pharmacia GST purification system.

Another fusion partner well known in the art is green fluorescent protein (GFP). This fusion partner serves as a fluorescent "tag" which allows the fusion protein of the invention to be identified by fluorescence microscopy or by flow cytometry. The GFP tag is useful when assessing subcellular localization of the fusion polypeptide of the invention, or for isolating cells which express the fusion polypeptide of the invention. Flow cytometric methods such as fluorescence activated cell sorting (FACS) are particularly useful in this latter application.

Preferably, the fusion partners also have protease cleavage sites, such as for Factor $X_a$ or Thrombin, which allow the relevant protease to partially digest the fusion protein of the invention and thereby liberate the recombinant protein of the invention therefrom. The liberated protein can then be isolated from the fusion partner by subsequent chromatographic separation.

Fusion partners according to the invention also include within their scope "epitope tags", which are usually short sequences for which a specific antibody is available. Well-known examples of epitope tags for which specific monoclonal antibodies are readily available include c-myc, influenza virus haemagglutinin and FLAG tags.

Other derivatives contemplated by the invention include, but are not limited to, modification to side chains, biotinylation, modification with fluorochromes, incorporation of unnatural amino acids and/or their derivatives during peptide, polypeptide or protein synthesis, the use of crosslinkers and other methods which impose conformational constraints on the isolated protein of the invention. Examples of side chain modifications contemplated by the present invention include: modifications of amino groups such as by acylation; modification of carboxyl groups by carbodiimide activation via O-acylisourea formation followed by subsequent derivitization; sulfydryl group modification by methods such as performic acid oxidation to cysteic acid; formation of mercurial derivatives; formation of a mixed disulfides; alkylation of tryptophan residues; nitration of tyrosine residues; and modification of the imidazole ring of a histidine residue by alkylation; although without limitation thereto.

Examples of non-natural amino acids include but are not limited to, use of 4-amino butyric acid, 6-aminohexanoic acid, 4-amino-3-hydroxy-5-phenylpentanoic acid, 4-amino-3-hydroxy-6-methylheptanoic acid, t-butylglycine, norleucine, norvaline, phenylglycine, ornithine, sarcosine, 2-thienyl alanine and/or D-isomers of amino acids.

In another aspect, the invention provides an isolated nucleic acid encoding the aforementioned isolated protein of the invention.

The isolated nucleic acid of the invention may be useful for recombinant protein expression in vivo in an animal, or in a host cell for the purposes of subsequent recombinant protein purification.

It will be appreciated by persons skilled in the art that advantage may be taken of degeneracy in the genetic code to alter an encoding nucleotide sequence of an amino acid sequence.

In a particular example, a nucleotide sequence may be engineered according to codon preference or usage in an organism or cell type to thereby optimize encoded protein translation and expression in that organism or cell type.

The term "nucleic acid" as used herein designates single- or double-stranded mRNA, RNA, cRNA and DNA, said DNA inclusive of cDNA and genomic DNA.

Nucleic acids may comprise genetically-encoded bases such as adenine, guanine, cytosine, thymine and uracil, or modified bases such as inosine, methylinosine and methyladenosine, thiouridine and methylcytosine, although without limitation thereto.

The term "recombinant" as used herein means artificially produced through human manipulation of genetic material, such as involving techniques generally falling within the scope of "recombinant DNA technology" as is well understood in the art.

A "polynucleotide" is a nucleic acid having eighty (80) or more contiguous nucleotides, while an "oligonucleotide" has less than eighty (80) contiguous nucleotides.

A "probe" may be a single or double-stranded oligonucleotide or polynucleotide, suitably labelled for the purpose of detecting complementary sequences in Northern or Southern blotting, for example.

A "primer" is usually a single-stranded oligonucleotide, preferably having 15-50 contiguous nucleotides, which is capable of annealing to a complementary nucleic acid "template" and being extended in a template-dependent fashion by the action of a DNA polymerase such as Taq polymerase, RNA-dependent DNA polymerase or Sequenase™.

An "amplification product" refers to a nucleic acid product generated by nucleic acid amplification techniques.

An embodiment of an isolated nucleic acid comprises a nucleotide sequence set forth in any one of SEQ ID NOS: 50-57 and as shown in FIG. 15.

Also contemplated according to the present invention are isolated nucleic acids that encode variants and/or derivatives of the isolated protein as hereinbefore described.

In some embodiments, nucleic acid variants encode isolated protein variants as hereinbefore described.

In other embodiments, nucleic acid variants encode isolated proteins disclosed herein, or variants thereof, said nucleic acid variants adopting nucleotide sequence changes due to redundancy in the genetic code. In one particular form, such variants are "codon optimized" for expression in a particular organism or cell type.

Isolated nucleic acid variants may hybridize with an isolated nucleic acid encoding an isolated polyepitope protein under high stringency wash conditions.

High stringency conditions include and encompass:—
(i) from at least about 31% v/v to at least about 50% v/v formamide and from at least about 0.01 M to at least about 0.15 M salt for hybridisation at 42° C., and at least about 0.01 M to at least about 0.15 M salt for washing at 42° C.;
(ii) 1% BSA, 1 mM EDTA, 0.5 M NaHPO$_4$ (pH 7.2), 7% SDS for hybridization at 65° C., and (a) 0.1×SSC, 0.1% SDS; or (b) 0.5% BSA, 1 mM EDTA, 40 mM NaHPO$_4$ (pH 7.2), 1% SDS for washing at a temperature in excess of 65° C. for about one hour; and
(iii) 0.2×SSC, 0.1% SDS for washing at or above 68° C. for about 20 minutes.

In another embodiment, isolated nucleic acid variants may have at least 60%, 70%, 75%, 80%, 85%, 90%, or 95% sequence identity with a reference nucleic acid. Non-limiting examples of reference nucleic acids comprise a nucleotide sequence set forth in any one of SEQ ID NO:50-57.

Another aspect of the invention provides a genetic construct comprising an isolated nucleic acid of the invention, or a variant thereof.

The genetic construct may facilitate propagation, cloning and/or expression of the isolated nucleic acid.

In a preferred form, the genetic construct is an expression construct comprising an isolated nucleic acid of the invention operably linked to one or more regulatory sequences present in an expression vector.

An "expression vector" may be either a self-replicating extra-chromosomal vector such as a plasmid, or a vector that integrates into a host genome. Suitably, the expression vector provides said one or more regulatory nucleotide sequences. By "operably linked" is meant that said regulatory nucleotide sequence(s) is/are positioned relative to the recombinant nucleic acid of the invention to initiate, regulate or otherwise control transcription.

Regulatory nucleotide sequences will generally be appropriate for the host cell used for expression. Numerous types of appropriate expression vectors and suitable regulatory sequences are known in the art for a variety of host cells.

Typically, said one or more regulatory nucleotide sequences may include, but are not limited to, promoter sequences, leader or signal sequences, ribosomal binding sites, transcriptional start and termination sequences, translational start and termination sequences, and silencer, enhancer or activator sequences.

With regard to promoters, constitutive promoters (such as CMV, SV40, vaccinia, HTLV1 and human elongation factor promoters) and inducible/repressible promoters (such as tet-repressible promoters and IPTG-, metallothionin- or ecdysone-inducible promoters) are well known in the art and are contemplated by the invention. It will also be appreciated that promoters may be hybrid promoters that combine elements of more than one promoter, such as but not limited to the SRα promoter which is a hybrid between elements of HTLV1 and SV40 promoters.

Preferably, said expression construct also includes one or more selectable markers suitable for the purposes of selection of transformed bacteria (such as bla, kanR and tetR) or transformed mammalian cells (such as hygromycin, G418 and puromycin).

Expression constructs may be transfected, transformed or otherwise introduced into host cells by any of a number of well known techniques including, but not limited to, transformation by heat shock, electroporation, DEAE-Dextran transfection, microinjection, liposome-mediated transfection, calcium phosphate precipitation, protoplast fusion, microparticle bombardment, viral transformation and the like.

The conditions appropriate for protein expression will vary with the choice of expression vector and the host cell. This is easily ascertained by one skilled in the art through routine experimentation.

Suitable host cells for expression may be prokaryotic or eukaryotic, such as bacterial cells inclusive of *Escherichia coli* (DH5α for example), yeast cells such as *Pichia pastoris*, Sf9 cells utilized with a baculovirus expression system, mammalian cell lines such as human embryonic kidney (HEK) 293 cells, CHO cells, COS cells, CV1 cells, Jurkat and NIH3T3 cells although without limitation thereto.

Another aspect of the invention provides a method of producing the isolated protein disclosed herein in recombinant form, said method including the steps of expressing the isolated protein in a host cell as hereinbefore described and at least partly purifying the isolated protein under conditions that maintain the isolated protein in a substantially non-aggregated form.

By "non-aggregated" in this context is meant that a substantial portion of the isolated protein is in a soluble form in aqueous solution, typically in the absence of denaturing agents such as urea, SDS or guanidinium chloride.

Because of the hydrophobic nature of CTL epitopes and TAP sequences, expression of the isolated protein in bacteria tends to result in aggregated protein in the form of inclusion bodies (IBs). While IBs may be solubilised and the recombinant protein purified using an affinity matrix (such as a Ni-NTA matrix), isolated proteins comprising twenty (20) CMV CTL epitopes were resistant to this treatment. Accordingly, a preferred form of the invention provides an isolated protein comprising less than twenty (20) CMV and/or EBV CTL epitopes. Given that each CMV CTL epitope in Tables 1 and 2 comprises 8-13 amino acids, less than twenty (20) CMV CTL epitopes is equivalent to less than 160-240 constituent, epitope amino acids.

Furthermore, maintaining the purified recombinant protein in a soluble form is difficult and has been a contributing factor to the inability to successfully administer polyepitope proteins as an exogenous protein that elicits a CD8+ CTL response. As described in more detail in the Examples, a compatible buffer system to maintain indicated that the isolated polyepitope proteins require MES or a glycine buffer at an acidic pH to remain soluble.

Accordingly, one embodiment of the invention provides a method of producing the isolated protein disclosed herein in recombinant form, said isolated protein having fewer than twenty (20) CMVCTL epitopes or 160-240 constituent epitope amino acids, said method including the steps of expressing the isolated protein in a bacterial host cell as hereinbefore described and at least partly purifying the isolated protein under conditions that maintain the isolated protein in a substantially non-aggregated form, wherein the conditions include maintaining the isolated recombinant protein in an MES buffer or a glycine buffer under acidic conditions.

Acidic conditions may be any pH below 7, preferably in the range pH 2-6 or more preferably in the range of about pH 2.5 to about pH 5.6.

General guidance on producing recombinant proteins may be found in standard protocols as for example described in Sambrook et al., MOLECULAR CLONING. A Laboratory Manual (Cold Spring Harbor Press, 1989), in particular Sections 16 and 17; CURRENT PROTOCOLS IN MOLECULAR BIOLOGY Eds. Ausubel et al., (John Wiley & Sons, Inc. NY USA 1995-2001), in particular Chapters 10 and 16; and CURRENT PROTOCOLS IN PROTEIN SCIENCE Eds. Coligan et al., (John Wiley & Sons, Inc. NY USA 1995-2001, in particular Chapters 1, 5 and 6.

In embodiments relating to expression constructs for administration to humans, the expression construct of the invention is suitable for use as a DNA vaccine.

In particular forms, the expression construct of the invention may be a construct that utilizes an expression and delivery vector of viral origin, such as pox viruses and adenoviruses or a DNA plasmid vector.

When used as a vaccine delivery system, expression constructs of viral origin may be administered to an animal in the form of VLPs or as a "naked" nucleic acid construct.

In one particular embodiment, the expression construct according to this embodiment comprises a vaccinia virus promoter, such as the p7.5 promoter present in a plasmid vector. For example, production of a TK-recombinant vaccinia virus using marker rescue recombination as provided in Khanna et al., 1992. J Exp Med. 176 169.

In a more preferred embodiment, the invention provides an adenovirus-based expression construct for use in a vaccine delivery system. Adenovirus-based constructs are capable of infecting a broad spectrum of mammalian and human cells, including both quiescent and proliferating cell types.

Such adenovirus-based expression constructs may comprise a constitutive or inducible/repressible promoter such as by way of a tetracycline inducible/repressible system.

One form of the adenovirus-based expression construct is derived from a replication-incompetent A5 adenovirus lacking at least an E1 gene.

A particular form is the Ad5/F35 adenovirus-based expression construct and vaccine delivery system is provided in detail hereinafter. Reference is also made to Yotdna et al., 2001, Gene Therapy 8 930, in relation to the Ad5/F35 embodiment of adenovirus expression vectors.

It will be appreciated that the isolated protein of the invention, isolated nucleic acids and expression constructs encoding same may be useful in therapeutic and/or prophylactic treatment of a herpesevirus-associated disease or condition such as a Cytomegalovirus-associated or Epstein-Barr-associated disease and/or condition in animals, preferably humans.

In humans, CMV infection can cause a mononucleosis-like syndrome with prolonged fever, and/or a mild hepatitis. In certain high-risk groups, disease can be more severe, such as during infection of the unborn baby during pregnancy, in people who work with children, and in immunocompromised persons, such as the aged, organ transplant recipients and persons infected with human immunodeficiency virus (HIV). CMV may also be associated with some cancers such as glioma. The invention therefore provides pharmaceutical compositions and/or methods of prophylactic or therapeutic treatment of CMV infection, preferably in humans.

EBV infection can cause serious mononucleosis and is also associated with a variety of cancers and possibly autoimmune disorders. The invention therefore provides pharmaceutical compositions and/or methods of prophylactic or therapeutic treatment of CMV infection, preferably in humans.

Such pharmaceutical compositions and methods are suitable for delivery of the isolated protein in recombinant form, or encoded by an expression construct such as in a viral delivery vector. In this regard, it will be appreciated that the pharmaceutical composition may comprise separate isolated proteins respectively comprising CMV and EBV CTL epitopes or may comprise a single isolated protein comprising both EBV and CMV epitopes.

Suitably, pharmaceutical compositions further comprise a pharmaceutically-acceptable carrier, diluent or excipient.

By "pharmaceutically-acceptable carrier, diluent or excipient" is meant a solid or liquid filler, diluent or encapsulating substance that may be safely used in systemic administration. Depending upon the particular route of administration, a variety of carriers, well known in the art may be used. These carriers may be selected from a group including sugars, starches, cellulose and its derivatives, malt, gelatine, talc, calcium sulfate, vegetable oils, synthetic oils, polyols, alginic acid, phosphate buffered solutions, emulsifiers, isotonic saline and salts such as mineral acid salts including hydrochlorides, bromides and sulfates, organic acids such as acetates, propionates and malonates and pyrogen-free water.

A useful reference describing pharmaceutically acceptable carriers, diluents and excipients is Remington's Pharmaceutical Sciences (Mack Publishing Co. N.J. USA, 1991) which is incorporated herein by reference.

Any safe route of administration may be employed for providing a patient with the composition of the invention. For example, oral, rectal, parenteral, sublingual, buccal, intravenous, intra-articular, intra-muscular, intra-dermal, subcutaneous, inhalational, intraocular, intraperitoneal, intracerebroventricular and transdermal administration may be employed.

Dosage forms include tablets, dispersions, suspensions, injections, solutions, syrups, troches, capsules, suppositories, aerosols, transdermal patches and the like. These dosage forms may also include injecting or implanting controlled releasing devices designed specifically for this purpose or other forms of implants modified to act additionally in this fashion. Controlled release of the therapeutic agent may be effected by coating the same, for example, with hydrophobic polymers including acrylic resins, waxes, higher aliphatic alcohols, polylactic and polyglycolic acids and certain cellulose derivatives such as hydroxypropylmethyl cellulose. In addition, the controlled release may be effected by using other polymer matrices, liposomes and/or microspheres.

Preferred pharmaceutical compositions are "immunogenic compositions" that elicit a CT: response to thereby provide prophylactic and/or therapeutic treatment of herpesvirus (e.g CMV and/or EBV) responsive to such immunotherapy, without necessarily eliciting a protective immune response.

In a preferred form, the immunogenic composition may be a vaccine for eliciting a protective $CD8^+$ CTL-based immune response in a human subject that protects against CMV infection, or treats an existing herpesvirus (e.g CMV and/or EBV) infection.

In one particular embodiment, the pharmaceutical composition, inclusive of immunogenic compositions and vaccines, comprises the isolated protein disclosed herein and said pharmaceutically-acceptable carrier, diluent or excipient.

As will be described in more detail in the Examples, the isolated protein comprising a plurality of CMV and/or EBV CTL epitopes are highly efficient in generating CMV-specific $CD8^+$ T cell responses in virus healthy carriers. Furthermore, expanded $CD8^+$ T cells demonstrated strong expression of IFN-γ, TNF, MIP-1β and CD107a following stimulation with the protein. It is proposed that these functional characteristics of the CD8+ T cells are important for predicting the efficacy of CTL-mediated immune responses and virus clearance.

Alternative embodiments provide a pharmaceutical composition, inclusive of immunogenic compositions and vaccines, comprising a nucleic acid expression construct, inclusive of DNA vaccines, encoding the isolated protein disclosed herein and said pharmaceutically-acceptable carrier, diluent or excipient. According to this alternative embodiment, the pharmaceutical composition, inclusive of immunogenic compositions and vaccines, may comprise an expression construct that utilizes a viral vector such as an adenoviral vector or pox virus-derived vector as hereinbefore described.

Any suitable procedure is contemplated for producing such vaccines. Exemplary procedures include, eg., those described in New Generation Vaccines (1997, Levine et al., Marcel Dekker, Inc. New York, Basel, Hong Kong) which is incorporated herein by reference.

Pharmaceutical compositions, immunogenic compositions, vaccines and/or methods of prophylactic or therapeutic treatment may include one or more immunostimulatory molecules or adjuvants for administration to the animal.

Suitable immunostimulatory molecules and adjuvants include, but are not limited to: TLR agonists, lipopolysaccharide and derivatives thereof such as MPL, Freund's complete or incomplete adjuvant, hexadecylamine, octadecylamine, octadecyl amino acid esters, lysolecithin, dimethyldioctadecylammonium bromide, N,N-dicoctadecyl-N', N'bis(2-hydroxyethyl-propanediamine), methoxyhexadecylglycerol, and pluronic polyols; polyamines such as pyran, dextransulfate, poly IC carbopol; peptides such as muramyl dipeptide and derivatives, dimethylglycine, tuftsin; oil emulsions; and mineral gels such as aluminum phosphate, aluminum hydroxide or alum; lymphokines, Imiquimod, Guardiquimod, QuilA and immune stimulating complexes (ISCOMS).

Pharmaceutical compositions, immunogenic compositions, vaccines and/or methods of prophylactic or therapeutic treatment may include one or more other TLR agonists for administration to the animal. Preferably, the one or more TLR agonists include a TLR4 agonist and/or a TLR9 agonist.

Preferred TLR4 agonists are lipolopysacchardides (LPS) or derivatives or components of LPS. These include Monophosphoryl lipid A (MPL®) derived from *Salmonella minnesota* and synthetic TLR4 agonists such as aminoalkyl glucosaminide phosphates (AGPs). A preferred TLR4 agonist is MPL.

TLR9 recognizes specific unmethylated CpG oligonucleotides (ODN) sequences that distinguish microbial DNA from mammalian DNA. CpG ODNs oligonucleotides contain unmethylated CpG dinucleotides in particular sequence contexts (CpG motifs). These CpG motifs are present at a 20-fold greater frequency in bacterial DNA compared to mammalian DNA. Three types of stimulatory ODNs have been described: type A, B and C. Non-limiting examples of TLR9 agonists include CpG ODN1826, CpG ODN2006, CpG ODN2216 and CpG ODN2336, although without limitation thereto.

Generally, pharmaceutical compositions, immunogenic compositions, vaccines and/or methods of prophylactic or therapeutic treatment may employ any safe route of administration may be employed for providing a patient with the composition of the invention. For example, oral, rectal, parenteral, sublingual, buccal, intravenous, intra-articular, intra-muscular, intra-dermal, subcutaneous, inhalational, intraocular, intraperitoneal, intracerebroventricular, transdermal and the like may be employed. Intra-muscular and subcutaneous injection is appropriate, for example, for administration of immunogenic compositions, proteinacious vaccines and DNA vaccines.

With regard to methods of treatment of a herspesvirus infection such as a CMV or EBV infection and/or a disease or condition associated with, or resultant from a CMV or EBV infection, the invention contemplates adoptive immunotherapy.

Preferably, although not exclusively, the invention contemplates adoptive immunotherapy using autologous CTLs produced in vitro.

Current methods for expanding herpesvirus (e.g CMV or EBV) CTLs are very difficult and are often based on either using a CMV lysate or individual peptide epitopes.

The isolated protein of the invention is expected to be more advantageous than either of these prior art approaches by facilitating expansion of broadly focussed T cell responses.

Accordingly, a method of expanding herpesvirus-specific CTLs for adoptive immunotherapy, includes the steps of:
(a) contacting one or more cells isolated from an animal with the isolated protein disclosed herein; and
(b) culturing said one or more cells to thereby expand herpesvirus-specific CTLs from said one or more cells.

Furthermore, a method of adoptive immunotherapy includes the step of administering said herpesvirus-specific CTLs produced at step (b) to an animal to thereby prophylactically or therapeutically treat a herpesvirus infection of said animal.

Preferably, the animal is a mammal, such as a human.

In one embodiment, the invention provides a method of autologous adoptive immunotherapy in a human including the steps of:
(A) contacting one or more cells isolated from a human with an isolated protein disclosed herein;
(B) culturing said one or more cells to thereby expand herpesvirus-specific CTLs from said one or more cells; and
(C) administering said herpesvirus-specific CTLs to said human to thereby prophylactically or therapeutically treat a herpesvirus infection of said animal.

In particular embodiments the herpesvirus is CMV or EBV.

In order that the invention may be readily understood and put into practical effect, particular embodiments will now be described by way of the following non-limiting examples.

EXAMPLES

Example 1

Purification and Immunogenicity of CMV Polyepitope Protein

Materials and Methods

Construction of CMV Polyepitope Vectors

A series of CMV polyepitope inserts were designed to encode multiple HLA class I restricted T-cell epitopes from five different antigens (pp65, IE-1, pp50, pp150 and gB). These polyepitope sequences encoded 13, 14, 15 or 20 different HLA class I-restricted CD8+ epitopes (see Table 1).

The polyepitope sequences were designed in such a way that each epitope sequence was preceded by a proteasome liberation amino acid sequence (AD or K or R) and a TAP recognition motif (RIW, ROW, NIW or NQY). In addition, a hexa-histidine tag (SEQ ID NO: 61) was inserted at the c-terminus of each polyepitope protein to allow purification using a nickel-nitrilotriacetic acid (Ni-NTA) column. The amino acid sequence of each construct was translated into DNA sequence based on *E. coli* codon utilisation and inserts were synthetically constructed (DNA2.0, California, USA) and cloned into an expression plasmid (pJexpress 404) under an isopropyl-β-D-thiogalactopyraniside (IPTG) inducible promoter. These synthetically designed polyepitope constructs were transformed into chemically competent *E. coli* DH5a (Invitrogen, Carlsbad, Calif., USA) and plasmids were purified using a QIAGEN maxi prep kit (QIAGEN, Hilden, Germany).

Protein Expression

Chemically competent *E. coli* BL21 (DE3) pLysS (Invitrogen, California, USA) was transformed with the CMV polyepitope expression vector. Transformed cells were plated on Luria Bertani (LB) agar supplemented with 100 μg/mL of ampicillin (LB-Amp) and plates were incubated overnight at 37° C. An isolated colony was picked and inoculated into 10 ml of LB-Amp broth and grown in a shaker at 37° C. and 200 rpm overnight. A small amount of overnight culture was inoculated into 50 mL of LB-Amp broth and grown for 12 hours, then 1% of culture was transferred into 2 L of LB-Amp broth that was then was grown until the O.D. reached 0.6 at 600 nm. CMV polyepitope protein induction was carried out by adding 1 mM/mL of IPTG. These cells were allowed to grow for an additional 4 hours and protein expression levels were determined by analysing un-induced and induced samples on 12-15% sodium dodecyl sulphate polyacrylamide gel electrophoresis (SDS-PAGE).

CMV Polyepitope Protein Purification

At the end of the induction phase, *E. coli* cultures were harvested by centrifugation at 10,000 rpm for 15 minutes, the cell pellet was resuspended in 80 mL of lysis buffer (25 mM Tris pH 7.4, 0.5% TritonX100, 150 mM NaCl, 0.5 mg/mL lysozyme) supplemented with a protease inhibitor cocktail (Roche, Mannheim, Germany) and incubated on the ice for 30 minutes. Cell lysis was carried out by sonication on ice for 4×5 minutes cycles with a 10 minute break between each cycle. The lysate was centrifuged at 13,000 rpm for 30 minutes and supernatant and pellet fractions were analysed using SDS-PAGE. Since the majority of the protein was found in the pellet fractions in the form of inclusion bodies (IBs), IBs were washed once with lysis buffer (without lysozyme) under stirring for two hours at RT and solubilised in 150 mL of solubilisation buffer (100 mM $NaH_2PO_4$, 10 mM Tris, 8 M urea pH 8.0) overnight at 4° C. The soluble protein was clarified by centrifugation at 13,000 rpm for 30 minutes and supernatant was used for purification of polyepitope proteins.

To purify the CMV polyepitope proteins we used 5 mL of Ni-NTA (QIAGEN, Hilden, Germany) metal-affinity chromatography matrix. The matrix was washed with 5 column volumes of distilled water followed by equilibration with 3 column volumes of solubilisation buffer. The soluble protein was loaded on the column and the flow rate was adjusted to 1 mL/minute. The unbound protein and impurities were washed-out with 10 column volumes of wash buffer 1 (100 mM $NaH_2PO_4$, 10 mM Tris, 8 M urea pH 6.3) and 20 column volumes of wash buffer 2 (100 mM $NaH_2PO_4$, 10 mM Tris, 8 M urea pH 5.9). The bound protein was eluted with elution buffer (100 mM $NaH_2PO_4$, 10 mM Tris, 8 M urea pH 4.3) and the eluted fractions were analysed using SDS-PAGE. The positive fractions were pooled together and CMV polyepitope protein estimation was carried out using a Bradford assay kit (Bio-Rad, Hercules, Calif., USA) following the manufacturer's instructions. Purified protein was subjected to a solubility test (to identify the right buffer composition for storing the protein in the soluble form) in which 80 μL of purified protein was diluted into 800 μL of various compositions of buffers with different pH ranges. These include (a) 25 mM MES buffer pH 5.6; (b) 25 mM MES buffer pH 3.2; (c) 25 mM MES pH 4.5; (d) 25 mM MES (2-(N-morpholino) ethanesulfonic acid) pH 4.5 and 400 mM L-arginine; (e) 10 mM Tris and 100 mM $NaH_2Po_4$ pH 4.3; (6) 10 mM Tris, 100 mM $NaH_2Po_4$ and 400 mM L-arginine pH 4.3; (f) PBS, 50 mM L-arginine and 50 mM L-glutamic acid pH7.4; (g) diluted in water; (h) 100 mM glycine buffer pH 2. These samples were incubated at 4° C. overnight; spun at 13,000 rpm for 25 minutes and supernatant fractions were analysed using SDS-PAGE. CMV polyepitope protein was dialysed against 25 mM MES buffer at pH 5.6. The CMV polyepitope protein was concentrated using Ultracel-10K spin columns (Millipore, County Cork, Ireland) followed by sterile filtration using 0.24 membrane filter, total protein was estimated using BIO-RAD Bradford protein assay kit and various concentrations of CMV polyepitope protein was analysed using SDS-PAGE to determine the final purity of polyepitope protein. The purified protein was stored in 1 ml aliquots at −70° C.

In Vitro Stimulation and Expansion of CMV Specific T-Cells from Healthy Donors Using Polyepitope Proteins Peripheral blood mononuclear cells (PBMC) from healthy virus carriers were incubated with 25 μg of purified polyepitope protein at 37° C., 6.5% $CO_2$ for 2 hours. After incubation, these PBMC were mixed with un-pulsed PBMC and resuspended in RPMI 1640 medium supplemented with 10% FCS (referred to as growth medium). These cells were cultured in a 24 well plate for 10 days at 37° C., 6.5% $CO_2$. On days 3 and 6, cultures were supplemented with 1 mL of growth medium containing 100 U of recombinant IL-2. The T cell specificity of these in vitro expanded cells was assessed using a standard ICS assay. In addition, T cells in these cultures were also assessed for polyfunctional capacity using multi-parameter flow cytometry.

Analysis of Processing and Presentation of $CD8^+$ T Cell Epitopes from CMV Polyepitope Protein by Human Cells Epstein-Barr virus (EBV) transformed LCLs and HEK 293 cells were used as antigen presenting cells in these assays. These cells were pulsed with 25-100 μg of CMV polyepitope protein for two hours at 37° C., 6.5% $CO_2$ and then washed twice with RPMI 1640 medium, resuspended in growth medium and incubated overnight at 37° C., 6.5% $CO_2$. After overnight incubation, antigen presenting cells were exposed to CMV-specific T cells at a responder to stimulator ratio of 4:1 for four hours at 37° C., 6.5% $CO_2$ and T cells assessed for cytokine expression using ICS assays.

Enzyme Inhibition Assays

To assess the role of various proteases involved in the processing of CMV polyepitope protein, LCLs were pre-treated with different inhibitors and then used as antigen presenting cells. These inhibitors were specifically targeted to inhibit lysosomes/endosome acidification (80 μM chloroquine and 10 mM Bafilomycin A1), the recycling pathway (200 μM primaquine), cysteine proteases (100 μM leupeptin and 100 μM E64), acid proteases (pepstatin A), autophagy mediators (10 mM 3-methyladenine (3-MA)), the proteasome complex (10 μM lactacystine, 1 μM epoxomicin and MG132), golgi transport (1 μg/mL brefeldin A and 0.7 μg/mL monensin) or aminopeptidase enzymes (30 μM leucinethiol with 0.5 mM dithiothreitol (DTT)). Following pre-treatment with these inhibitors, cells were incubated with 25 µg of CMV polyepitope protein for two hours at 37° C., 6.5% $CO_2$, washed twice with RPMI 1640 medium, resuspended in growth medium and incubated overnight at 37° C., 6.5% $CO_2$. After overnight incubation, cells were exposed to CMV-specific T cells at a responder to stimulator ratio of 4:1 for four hours at 37° C., 6.5% $CO_2$ and T cells assessed for cytokine expression using ICS assays.

Silencing of Atg12 or Sec61 with Short Hairpin RNA (shRNA)

Lentivirus based vectors encoding ATG12 shRNA (clone ID NM_004707.2-485s1c1, (CCGGTGTTGCAGCTTC-CTACTTCAACTCGAGTTGAAGTAGGAAGCTG-CAACAT TTTT; SEQ ID NO:59) or Sec61 shRNA (clone ID NM_006808.2-410s1c1, CCGGCCCAACATTTCTTG-GACCAAACTCGAGTTTGGTCCAAGAAATGT-TGGGTT TTTTG; SEQ ID NO:60) were obtained from Sigma-Aldrich in an E. coli host. Plasmid encoding shRNA was purified using the large scale plasmid purification kit (Qiagen, Hilden, Germany). Lentivirus was produced in HEK293T cells by cotransfecting the shRNA vector or control vector (pLKO.1puro) with a packaging vector, pHR8.2ΔR, and an envelope vector, pCMV-VSV-G (vesicular stomatitis virus glycoprotein G). Following 48 and 72 hours of transfection, Lentivirus containing supernatant was harvested, 0.45 µm filtered, and stored at −80° C. Transduction was performed by resuspending $3\times10^5$ CEM.T1, CEM.T2 cells or LCLs in 1 mL of lentivirus containing supernatant and centrifuging for 30 minutes at 800 g and 32° C. Puromycin (1 µg/mL) was added 48 hours after transduction. To generate complete knock down cells were reinfected with the identical lentivirus vector on day 10 and cells were used for downstream assays after 5-7 days of transduction.

Western Blotting

Western blot analysis was performed as previously described (Ausubel 1995). Briefly, lentivirus shRNA infected cells were washed in PBS and lysed with RIPA buffer (Thermo Scientific, Rockford, Ill., USA) on ice according to the manufacturer's instructions. Protein was quantified using a DC protein assay kit (Bio-Rad laboratories, Hercules, Calif., USA). Lysate was mixed with SDS-PAGE loading buffer and resolved on 12-15% SDS-PAGE gels, then transferred to a nitrocellulose membrane (using a Mini Trans-Blot apparatus (Bio-Rad, CA, USA) in pre-chilled transfer buffer (1× Tris-glycine buffer containing 20% methanol) at 100V for 1 hour. Following transfer the nitrocellulose membrane was washed three times in wash buffer (PBS containing 0.05% V/V Tween-20), then incubated in blocking buffer (PBS containing 5% skim milk) for 1 hour at room temperature on a shaker. The membrane was incubated in rabbit anti-Sec61 (Thermo Scientific, Australia) or rabbit anti-ATG12 (Cell Signaling Technology, Danvers, Mass.) primary antibody solution (diluted in blocking buffer) overnight at 4° C. on a shaker. The membrane was washed 6 times with wash buffer for 10 minutes each wash, then incubated with sheep anti-rabbit conjugated to horse-radish peroxidase (Chemicon, Australia) secondary antibody (diluted in blocking buffer) for 1 hour at room temperature. The nitrocellulose membrane was washed in wash buffer, incubated with ECL reagent (Merck, Darmstadt, Germany) and protein visualised on an X-ray film.

Statistical Analysis

Statistical analyses were carried out using Graph Pad software or Microsoft Office Excel 2007. For $CD8^+$ T cell responses, the means±SD were calculated and p values were determined using the Student's t-test. Error bars represent S.E.M. Where indicated with *,  and * represents statistically significant with $p<0.05$, $p<0.01$ and $p<0.001$ respectively when compared to the controls.

Results

Purification and Characterisation of CMV Polyepitope Protein

Figure 2:
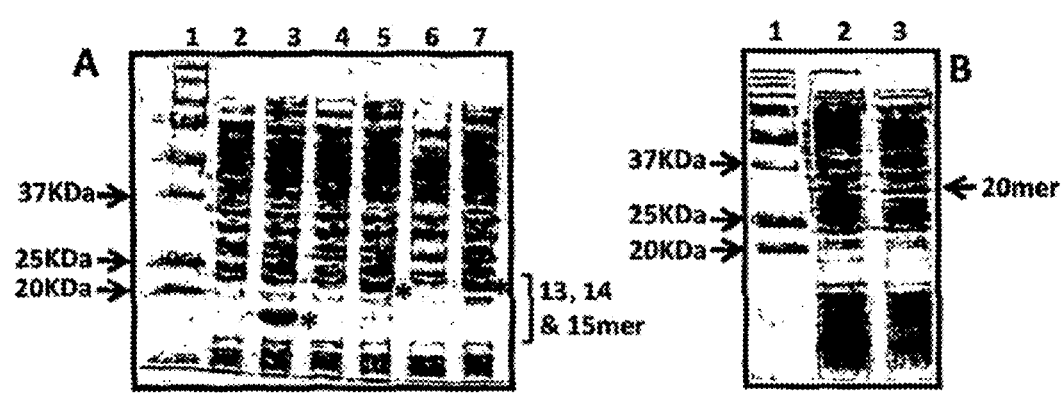
FIG. 2: Expression and purification of CMVpoly-PTL proteins. The pJexpress 404 plasmids expressing the CMVpoly-PTL proteins which include 13, 14, 15 or 20 CMV CD8+ T cell epitopes were transformed into *E. coli* BL21 (DE3) pLysS. Protein expression was induced with IPTG and pre and post induction samples were analysed using SDS PAGE. Panel A and B shows expression of CMVpoly-PTL proteins in *E. Coli*: Lane 1, molecular weight marker (kDa); Lanes 2, 4 and 6 uninduced *E. coli* cell lysate; Lanes 3, 5 & 7 induced *E. coli* cell lysate. * indicates the CMVpoly-PTL proteins.
Figure 3:
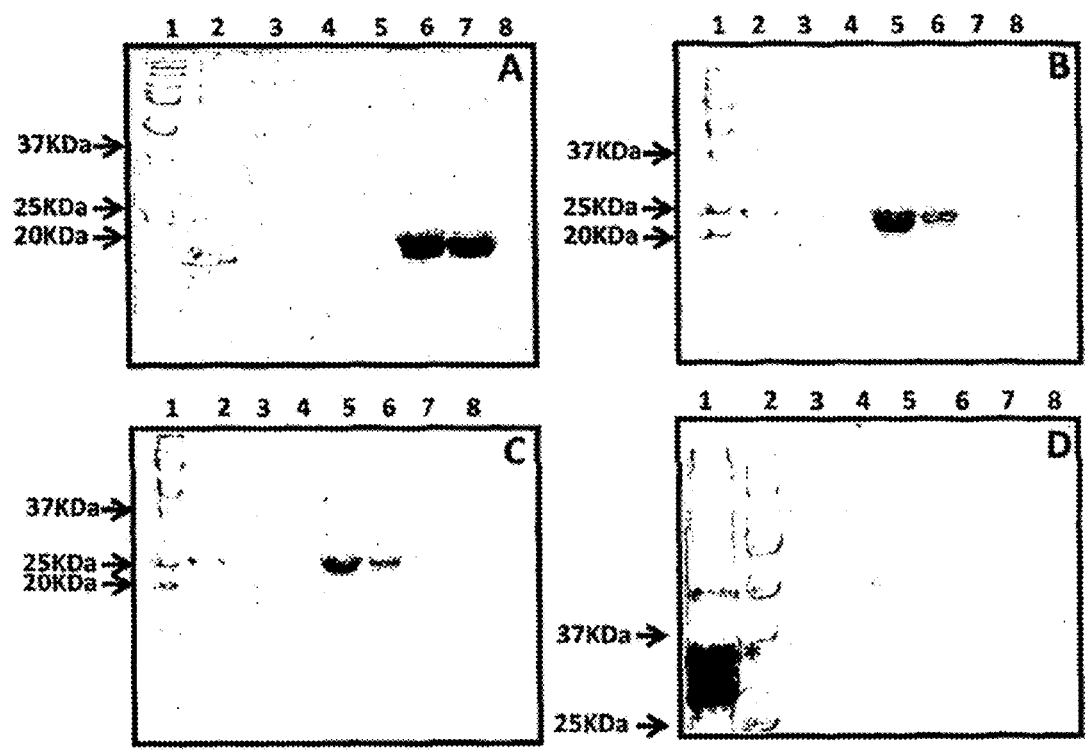
FIG. 3: SDS PAGE analysis of purified CMVpoly-PTL proteins Following CMVpoly-PTL purification on Ni NTA column, samples from various stages of purification were analysed by SDSPAGE. Panels A, B, C & D represent the purification of the CMVpoly-PTL proteins (13mer, 14mer, 15mer and 20mer). For all the SDS PAGE gels Lane 1: molecular weight marker. Lane 2: solubilised protein prior to loading. Lane 3: flow through. Lane 4: wash. Lanes 5, 6, 7 & 8: elution fractions. * indicates CMVpoly-PTL proteins.
Figure 4:
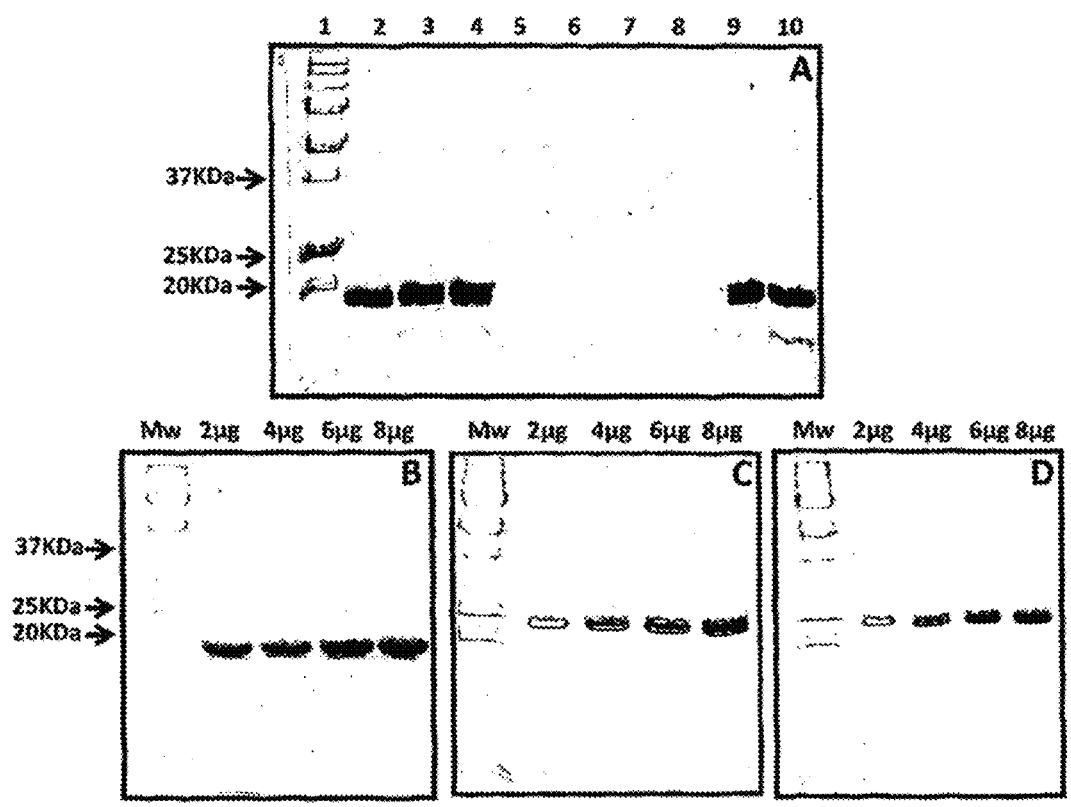
FIG. 4: CMVpoly-PTL protein solubility test and characterisation to determine a compatible buffer system for CMVpoly-PTL storage as a soluble protein, purified protein was diluted with various buffer compositions at different pH ranges, incubated at 4° C. O/N, centrifuged and supernatant fractions were analysed on SDS PAGE. Panel A: Lane 1: molecular weight marker. Lane 2: diluted with 25 mM 2-(N-morpholino) ethanesulfonic acid (MES) buffer pH 5.6. Lane 3: diluted with 25 mM MES buffer pH 3.2. Lane 4: diluted with 25 mM MES pH 4.5. Lane 5: diluted with 25 mM MES pH 4.5 and 400 mM L arginine. Lane 6: diluted with 10 mM Tris and 100 mM $NaH_2Po_4$ pH 4.3. Lane 7: diluted with 10 mM Tris, 100 mM $NaH_2Po_4$ and 400 mM L arginine pH 4.3. Lane 8: diluted with PBS, 50 mM L-arginine and 50 mM L-glutamic acid pH7.4. Lane 9: diluted with water. Lane 10: diluted with 100 mM glycine buffer pH 2. Panel B, C & D shows CMVpoly-PTL proteins purity analysis. Following dialysis of the CMVpoly-PTL polyepitope proteins (13mer, 14mer and 15mer) against MES buffer pH 5.6, different concentrations of each protein was analysed on SDS PAGE to observe the final purity and degradation products.

CMV polyepitope inserts encoding 13, 14, 15 or 20 minimal $CD8^+$ T cell epitopes were designed as outlined in FIG. 1. A comprehensive list of CMV epitopes included in each of these polyepitope sequences are presented in Table 1. These CMV polyepitope constructs were transformed into E. coli, protein expression conditions were optimised and analysed on SDS-PAGE. Results obtained from these experiments showed that CMV polyepitope protein (13, 14, 15 and 20mer) can be successfully expressed using a bacterial expression system under an IPTG inducible promoter at 37° C. (FIGS. 2A & B). Because of the hydrophobic nature of the linear $CD8^+$ T cell epitopes, the CMV polyepitope protein was aggregated in the form of inclusion bodies (IBs, data not shown). These IBs were solubilised and CMV polyepitope proteins from constructs encoding 13, 14 or 15 epitopes were purified using Ni-NTA matrix. This one step purification process allowed us to purify these CMV polyepitope proteins to homogeneity (FIG. 3A-C). However, purification of CMV polyepitope 20mer was not successful, despite using two different denaturing agents, 8M urea and 6M guanadine hydrochloride, to solubilise the IBs. Following solubilisation CMV polyepitope the 20mer protein remained in the pellet fraction; and no protein was detected in the elution fractions (FIG. 3D). The data obtained from the solubility test to identify a compatible buffer system to maintain indicated that CMV polyepitope proteins require MES or glycine buffers at an acidic pH to remain soluble (FIG. 4A). Following CMV polyepitope purification, various concentrations of protein were analysed on SDS-PAGE to check integrity. Data presented in FIG. 4B-D, shows minimal impurities and the molecular weights of the recombinant polyepitope proteins were approximately 19, 21 and 25 kDa which matched with the theoretically calculated molecular weight of the 13, 14 and 15mer polyepitope respectively. This one step purification step allowed us to obtain 80 mg of the 13mer, 4 mg of the 14mer and 15 mg of the 15mer protein from 2 L of culture.

Figure 5:
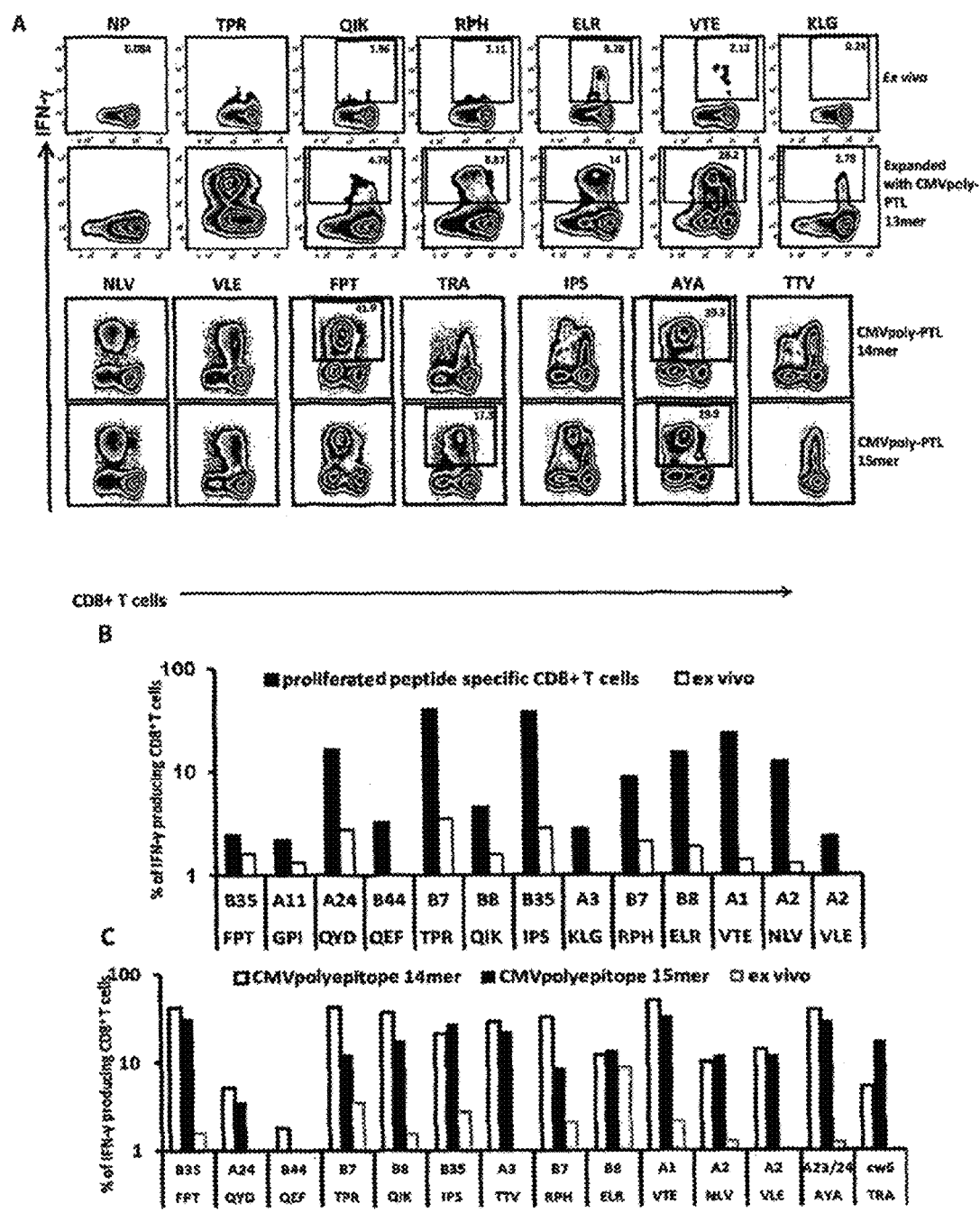
FIG. 5: Expansion of CMV-specific T cells following stimulation of PBMCs from CMV seropositive donors with the CMVpoly-PTL proteins: PBMC from various healthy CMV-seropositive donors were stimulated ex vivo with recombinant CMVpoly-PTL protein (13, 14 and 15mer) and cultured for 10 days in the presence of recombinant IL 2. The percentage of expanded peptide-specific CD8+ T cells producing IFN-γ was determined using an ICS assay and results were analysed using FIowJo. Panel A shows the representative FACS plots of in vitro expanded CMV-specific CD8+ T cells following stimulation of PBMC with or without the CMVpoly-PTL proteins. Panel B & C shows overall analysis of expanded CMV specific CD8+ T cells from different individuals following stimulation with CMVpoly-PTL proteins (13, 14 and 15mer).

Ex Vivo Expansion of CMV Epitope Specific $CD8^+$ T Cells from PBMC Following Stimulation with Polyepitope Protein To evaluate the immunogenicity of the CMV polyepitope proteins, we performed several in vitro experiments using various HLA typed CMV-seropositive donor PBMC to expand CMV specific $CD8^+$ T cells. PBMC from healthy donors were stimulated ex vivo with purified CMV polyepitope proteins and then assessed for antigen specificity by ICS assay and compared with ex vivo responses. The data obtained from these experiments showed that 13, 14 and 15mer CMV polyepitope proteins induced a rapid expansion of CMV specific $CD8^+$ T cell specific for the epitopes included in the polyepitope (FIG. 5A). In most cases dominant $CD8^+$ T cell responses were against multiple epitopes included in the CMV polyepitope. For example, data presented in FIG. 5A shows that a considerable increase in the percentage of CMV specific $CD8^+$ T cells against the multiple epitopes from individual donor PBMCs. In addition, we also showed that all epitopes within the CMV polyepitope were capable of expanding CMV specific $CD8^+$ T cells from PBMC and these responses ranged from 2 to 40% of the total CD8+ T cells (FIGS. 5B & 5C). Of particular interest was the QIK epitope as our in vitro expansion studies showed that T cells specific for this epitope can be expanded following stimulation with the polyepitope protein (FIG. 5B). In contrast, minimal expansion of QEF-specific T cells was observed suggesting that this epitope may not be efficiently processed by human cells. These results clearly demonstrate that CD8+ T cell epitopes included in the polyepitope proteins can be efficiently processed and presented by human cells and sensitization of human PBMC with polyepitope protein induces the rapid expansion of CMV-specific T cells.

Figure 6:
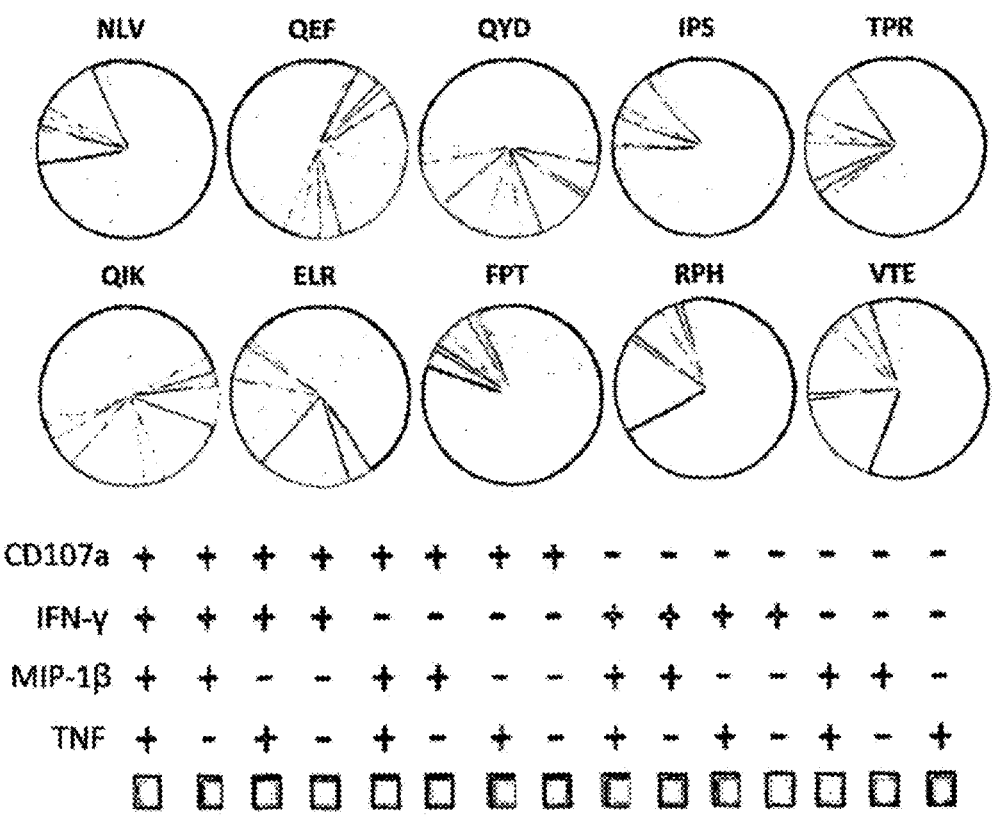
FIG. 6: The magnitude and quality of expanded CMV specific CD8+ T cells following stimulation with CMV polyepitope protein: Following PBMC stimulation with the CMVpoly-PTL protein (13mer), cells were analysed to assess for effector functions by multi parameter flow cytometry. The frequency of CD8+ T cells demonstrating cytolytic function (CD107a degranulation marker) and intracellular cytokine production (IFN γ, TNF and MIP 1β) were analysed on FIowJo and multifunctional cytokine producers were plotted using the SPICE program. Data in the pie chart is shown for an individual epitope and each slice of the pie chart represents each possible combination of functions.

CD8+ T Cells Expanded Following Stimulation with Polyepitope Proteins Display Polyfunctional Profile A large body of documented evidence suggest that polyfunctional CD4+ and CD8+ T cell responses are crucial in providing protection against a range of viral and microbial pathogens (Betts, Gray et al. 2006; Darrah, Patel et al. 2007; Millington, Innes et al. 2007). In addition, in the context of CMV, polyfunctional CD8+ T cells protect against high levels of viral replication after liver transplant (Nebbia, Mattes et al. 2008). These observations clearly highlight that polyfunctional CD8+ T cell responses are a prerequisite for the development of a potent CMV vaccine. In our subsequent experiments, we analysed effector functions of CMV specific CD8+ T cells expanded by polyepitope proteins. These analyses were designed to assess the ability of these effector cells to perform cytolytic function (CD107a mobilization) and express multiple cytokines (IFN-γ, TNF and MIP-1β). Representative data from one of these analyses is presented in FIG. 6. The majority of the CMV-specific CD8+ T cells expanded with the polyepitope displayed strong cytolytic function (as indicated by CD107a mobilization) and expressed multiple cytokines (IFNγ+, TNF+ and MIP1β+).

Figure 7:
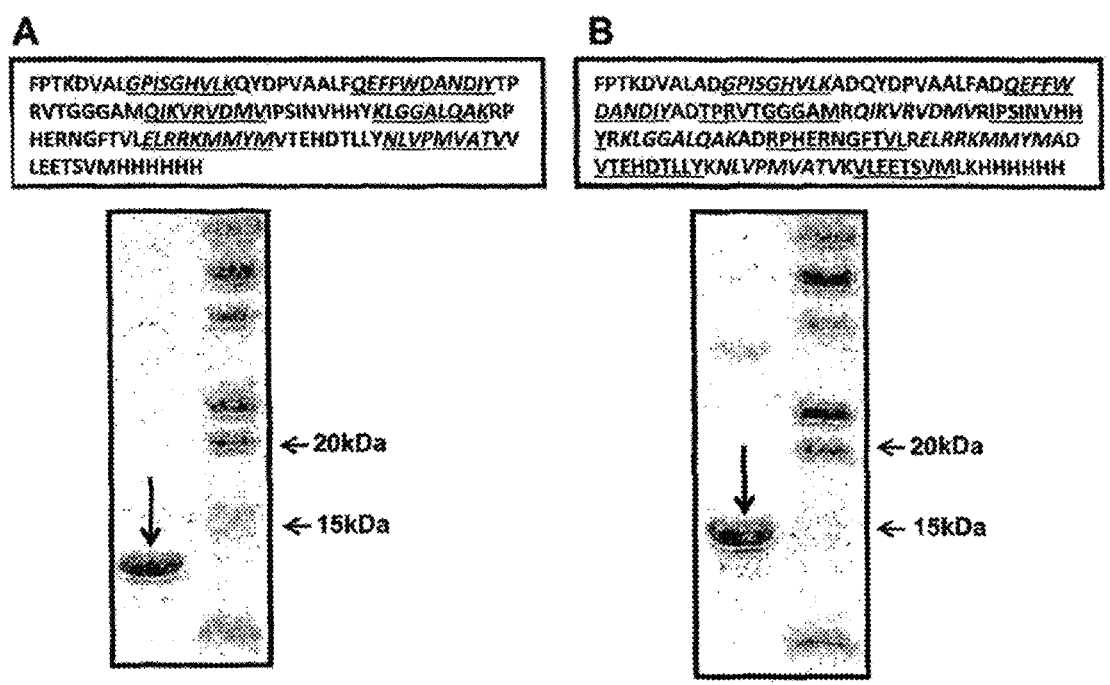
FIG. 7: Schematic design of the CMV polyepitope protein construct with and without linkers and protein purification: Panel A shows the design of CMV polyepitope protein without linkers (SEQ ID NO:75) (referred to as CMVpoly). Panel B shows the design of polyepitope protein with proteasome linkers (SEQ ID NO: 76) (referred to as CMVpoly-PL). Each of the alternate CD8+ T cell epitope sequences are italicised and underlined. For CMVpoly-PL each epitope sequence is separated by amino acid residue(s) which are targets for proteasomal degradation (shown in red). The DNA sequence encoding the CMV polyepitope proteins was cloned into an IPTG inducible plasmid, pJexpress 404, and transformed into *E. coli* for protein expression. Polyepitope protein was purified using Ni-NTA affinity chromatography.

Rational Design of the CMV Polyepitope Constructs with and without Linkers, Protein Expression, and Purification To delineate the precise role of spacer sequences in the processing and presentation of polyepitope proteins we have designed to encode 13 minimal CD8+ T cell epitopes without (CMVpoly) and with proteasome linkers (CMVpoly-PL) (FIGS. 7A & 7B). The CMV polyepitope constructs were transformed into E. coli, protein expression conditions were optimised, and polyepitope proteins were purified using Ni-NTA chromatography. Results obtained from these experiments showed that both the CMVpoly and CMVpoly-PL could be successfully expressed and purified to homogeneity using a bacterial expression system.

Figure 8:
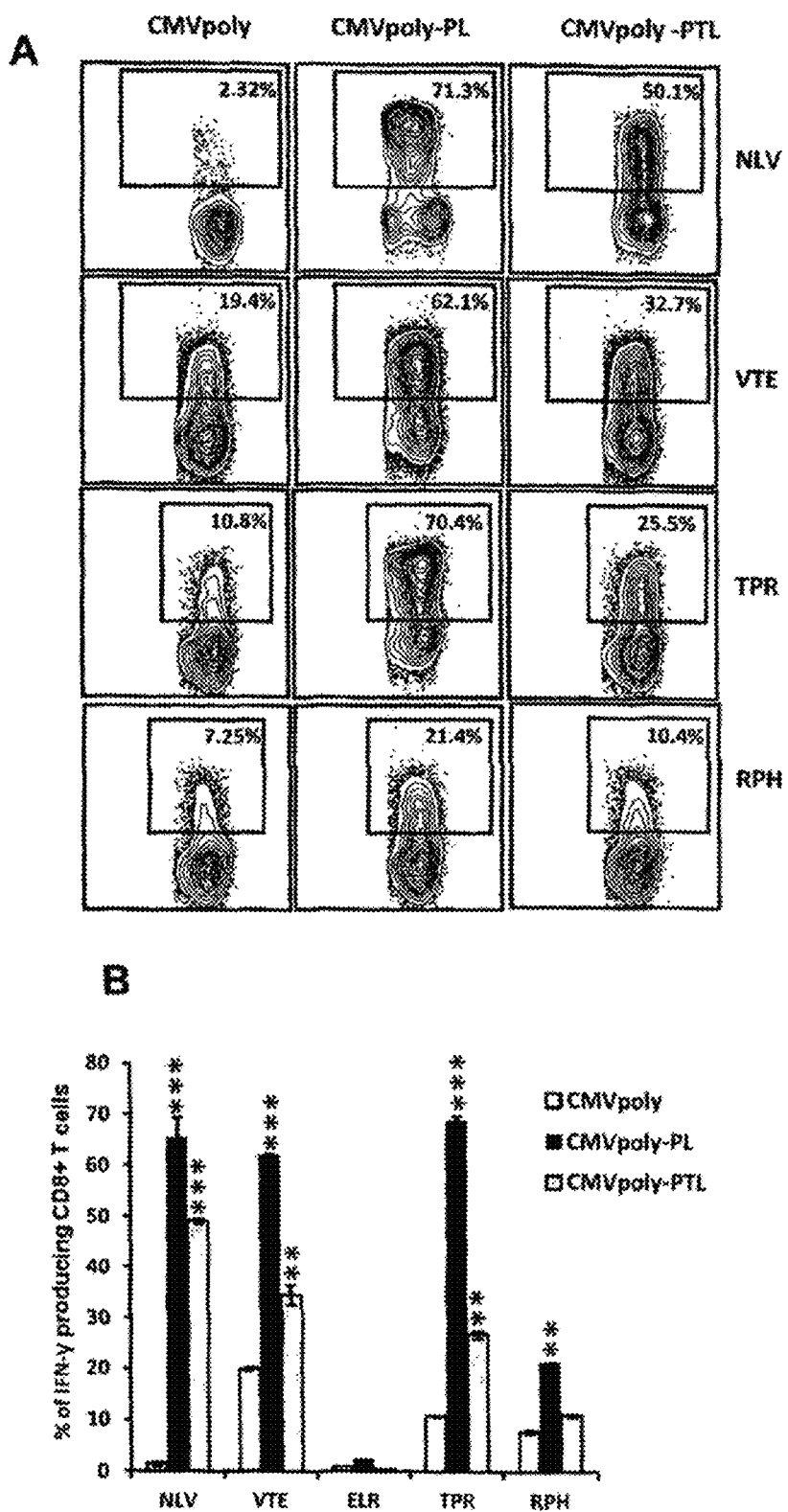
FIG. 8: In vitro assessment of processing and presentation of CMVpolyepitope proteins with and without linkers: Panel A shows in vitro cross-presentation of CMVpoly, CMVpoly-PL and CMVpoly-PTL proteins by human cells. EBV transformed LCLs were pulsed with CMVpoly, CMVpoly-PL or CMVpoly-PTL proteins (25 μg each) for two hours, washed, incubated overnight and then exposed to CMV-specific CD8+ T cells specific for HLA A2-restricted NLV (pp65), HLA A1-restricted VTE (pp50), HLA B8-restricted ELR (IE1), HLA B7-restricted RPH (pp65) and HLA B7-restricted TPR (pp65) epitopes. The FACS plots shows IFN-γ expression by the CMV-specific CD8+ T cells following co-culture with CMVpoly, CMVpolyPL or CMVpoly-PTL proteins pulsed LCLs. Panel B shows the mean±SEM of IFN-γ producing CMV epitope specific CD8+ T cells following co-culture with LCL pulsed with CMVpoly (empty bars), CMVpoly-PL (black bars) or CMVpoly-PTL (grey bars). Error represent the ±SEM.  or * indicates statistically significant ($p<0.001$ or $p<0.0001$), calculated by 2-tailed Student's t test.
Figure 9:
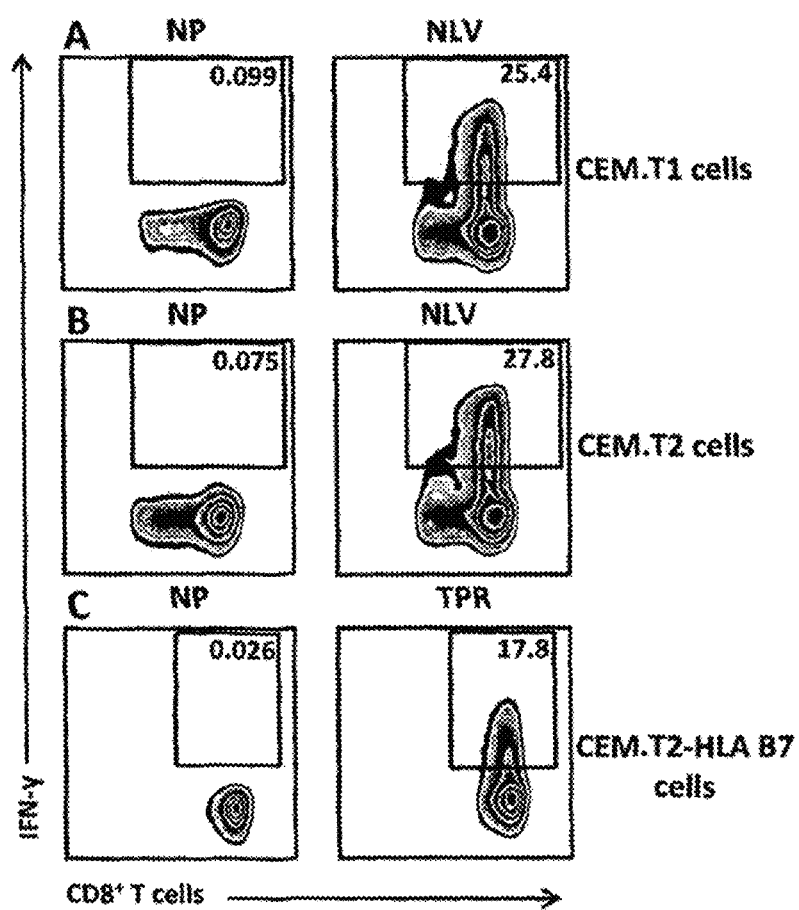
FIG. 9: Analysis of the cross-presentation of the CMV polyepitope protein by human cells: To identify the role of peptide transporters (TAP-1 and TAP-2) in the cross-presentation of CMV polyepitope protein, TAP1& 2+ cells (CEM.T1) and TAP1& 2-cells (CEM.T2 or CEM.T2 HLA B7) were pulsed with CMV-PTL protein for two hours, washed, incubated overnight and exposed to HLA A2-restricted NLV (pp65) or HLA B7-restricted TPR (pp65) epitope-specific CD8+ T cells. Panel A shows expression of IFN γ by NLV-specific T cells following exposure of CEM.T1 cells pre-sensitized with CMV polyepitope protein. Panel B & C shows the percentage of IFN-γ expressing NLV and TPR-specific CD8+ T cells following exposure to CMV polyepitope protein sensitized CEM.T2 and CEM.T2 HLA B7 cells respectively. The data shown in panels A, B & C is one representative experiment from two independent experiments.
Figure 10:
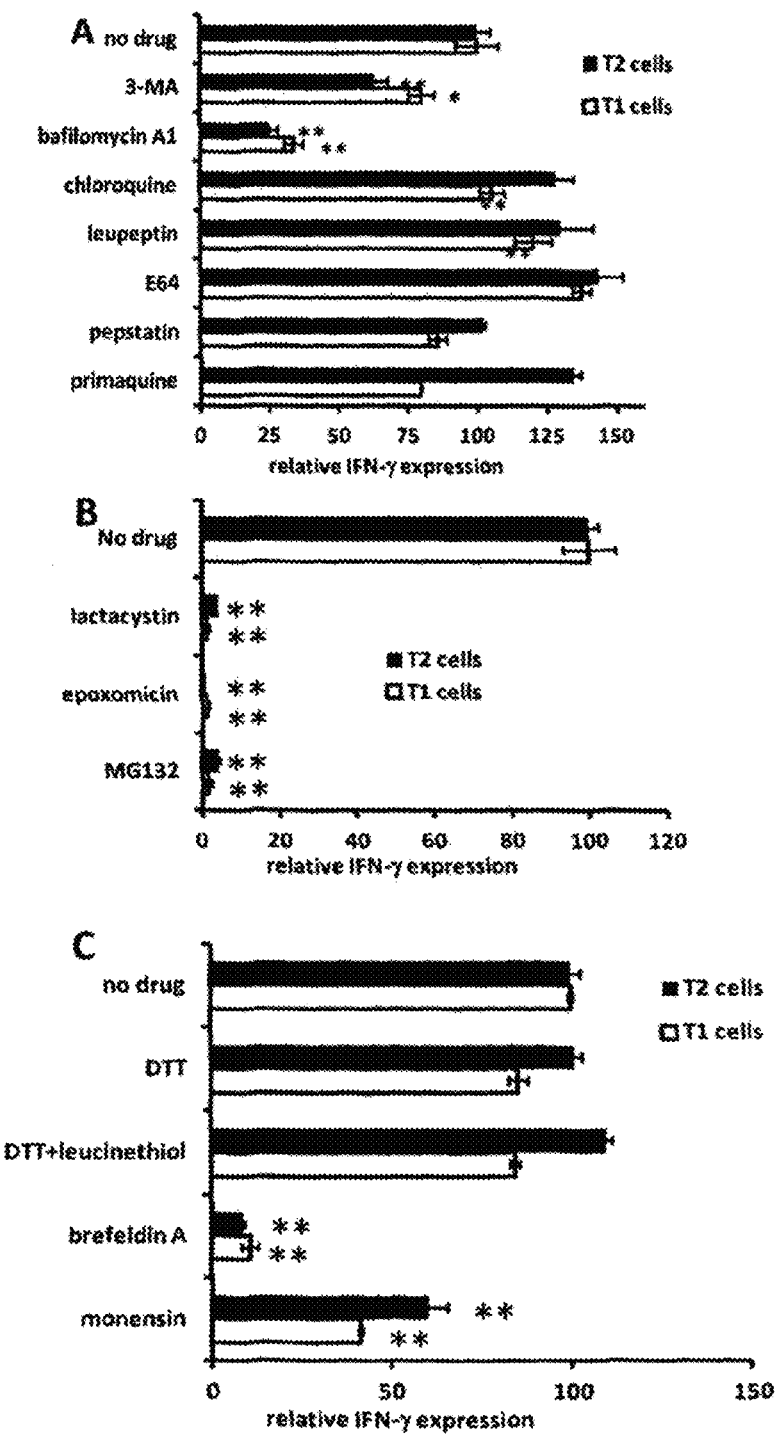
FIG. 10: The effect of different chemical inhibitors on the processing and presentation of the polyepitope protein: CEM.T1 and CEM.T2 cells were either untreated or pre treated with inhibitors for autophagy (3-MA), lysosomes/endosome (chloroquine or bafilomycin A1), the recycling pathway (primaquine), cysteine proteases (leupeptin or E64) or acid proteases (pepstatin A) (Panel A), proteasomal inhibitors, lactacystin, epoxomicin and MG132 (Panel B) and ER-resident aminopeptidase inhibitor (leucinethiol+ DTT) or its control (DDT alone) or golgi inhibitors (brefeldin A or monensin) (Panel C) prior to incubation with the CMV-PTL protein. Cells were washed and cultured in the presence of respective inhibitors for twelve hours and then exposed to HLA A2-restricted NLV (pp65)-specific CD8+ T cells and then assessed for IFN-γ expression by ICS assay. Data presented in each represents the relative IFN-γ expression by antigen-specific T cells following exposure to CMV-PTL sensitized CEM.T1 (empty bars; referred to as T1) and CEM.T2 (black bars; referred to as T2) cells. The data represents the mean of two independent experiments performed in triplicates. Error bars represent the ±SEM. * or ** indicates statistically significant ($p<0.05$ or $p<0.01$), calculated by 2 tailed Student's test.

In Vitro Evaluation of Immunogenicity of CMV Polyepitope Proteins with and without Linkers To investigate the processing and presentation of the CMVpoly, CMVpoly-PL and CMVpoly-PTL proteins, we incubated human lymphoblastoid cell lines (LCLs) overnight with CMVpoly, CMVpoly-PL and CMVpoly-PTL, and then assessed the activation of a panel of CMV-specific T cells using intracellular IFN-γ analysis. Representative FACS plots presented in FIG. 8A shows that HLA A2-restricted NLV (pp65), HLA A1-restricted VTE (pp50), HLA B7-restricted RPH and TPR (pp65) epitopes from CMVpoly-PL or PTL were more efficiently processed and presented to CMV-specific T cells compared to LCLs pulsed with CMVpoly. More importantly, the activation of CMV-specific T cells were significantly higher following stimulation with LCL pulsed with CMVpoly-PL or CMVpoly-PTL compared to CMVpoly (FIG. 8B). Collectively, these data indicate that to enhance the processing and presentation of the exogenously delivered polyepitope proteins to the antigen-specific CD8+ T cells requires proteasome and/or TAP linkers between the epitopes CD8+ T Cell Epitopes from the Polyepitope Protein are Cross-Presented Through a TAP-Independent Pathway but Involves Proteasome and the Autophagy Dependent Pathway To delineate the precise pathway for the processing and presentation of CD8+ T cell epitopes from the exogenously loaded polyepitope protein in the next set of experiments we pulsed polyepitope protein in TAP+ (CEM.T1) and TAP− (CEM.T2 and CEM.T2-HLA B7) LCLs and then exposed these cells to CMV-specific T cells. Data presented in FIG. 9 shows that both TAP+ and TAP− B cells can efficiently present CD8+ T cell epitopes from the polyepitope protein. To delineate the mechanisms of polyepitope presentation we used CEM.T1 and CEM.T2 cells as antigen presenting cells to stimulate HLA A2 restricted NLV-specific CD8+ T cells. These antigen presenting cells were first pre-treated with inhibitors for lysosome/endosomal acidification (chloroquine and bafilomycin A1), the recycling pathway (primaquine), cysteine proteases (leupeptin and E64), and acid proteases (pepstatin A) and then pulsed with polyepitope protein. Data presented in FIG. 10A shows that rather than blocking the presentation of polyepitope proteins, lysosome, recycling pathway and cysteine protease inhibitors significantly increased the T cell recognition of CEM.T1 and/or CEM.T2 cells pulsed with the polyepitope protein. These observations suggest that the pre-treatment with leupeptin, E64 or pepstatin A may protect the CD8+ T cell epitopes within the polyepitope protein from degradation by cysteine and acid proteases. Unexpectedly, chloroquine and bafilomycin A1 showed opposing effects on the cross-presentation of the polyepitope protein. While chloroquine enhanced the antigen presentation in CEM.T2 cells, pre-treatment with bafilomycin A1 significantly reduced the T cell recognition of polyepitope pulsed antigen presenting cells (FIG. 10A). Previous studies have shown that bafilomycin A1 is also a potent and specific inhibitor of vacuolar H+ ATPase and prevents maturation of autophagic vacuoles by inhibiting fusion between autophagosomes and lysosomes. To explore whether the polyepitope protein processing may involve the autophagy pathway, we pre-treated antigen presenting cells with the PI3K inhibitor, 3-methyladenine (3-MA) and then exposed to CMV-specific T cells. Data presented in FIG. 10A shows that 3-MA treatment also effected the presentation of CD8+ T cell epitopes from the polyepitope protein. These observations suggest that it is likely that cross-presentation of the polyepitope protein is via an autophagy dependent pathway.

In the next set of experiments we investigated the potential role of the proteasome complex in cross-presentation of the polyepitope protein. CEM.T1 and CEM.T2 cells were pre-treated with the proteasome inhibitors lactacystin, epoxomicin and MG132 and then pulsed with polyepitope protein. These cells were then assessed for the presentation of CD8+ T cell epitopes. Data presented in FIG. 10B shows that all three proteasome inhibitors completely blocked the presentation of CD8+ T cell epitopes from the polyepitope proteins. It is important to note that presentation of CD8+ T cell epitopes does not depend on the expression of immunoproteasomes since CEM.T2 cells, which don't express these components of the proteolytic complex, can efficiently process CD8+ epitopes from the polyepitope protein. We next focused our attention on the potential role of the secretory pathway and ER-resident aminopeptidases in the presentation of CD8+ T cell epitopes from the polyepitope protein. Data presented in FIG. 10C shows that pre-treatment with brefeldin-A and monensin significantly blocked presentation to CD8+ T cells, while leucinethiol treatment had minimal effect on the T cell recognition of CEM.T1 and CEM.T2 cells. These results suggest that the polyepitope protein is processed via a proteasome dependent but ER independent pathway that may involve the retrotranslocation pathway, which degrades misfolded ER proteins.

Figure 11:
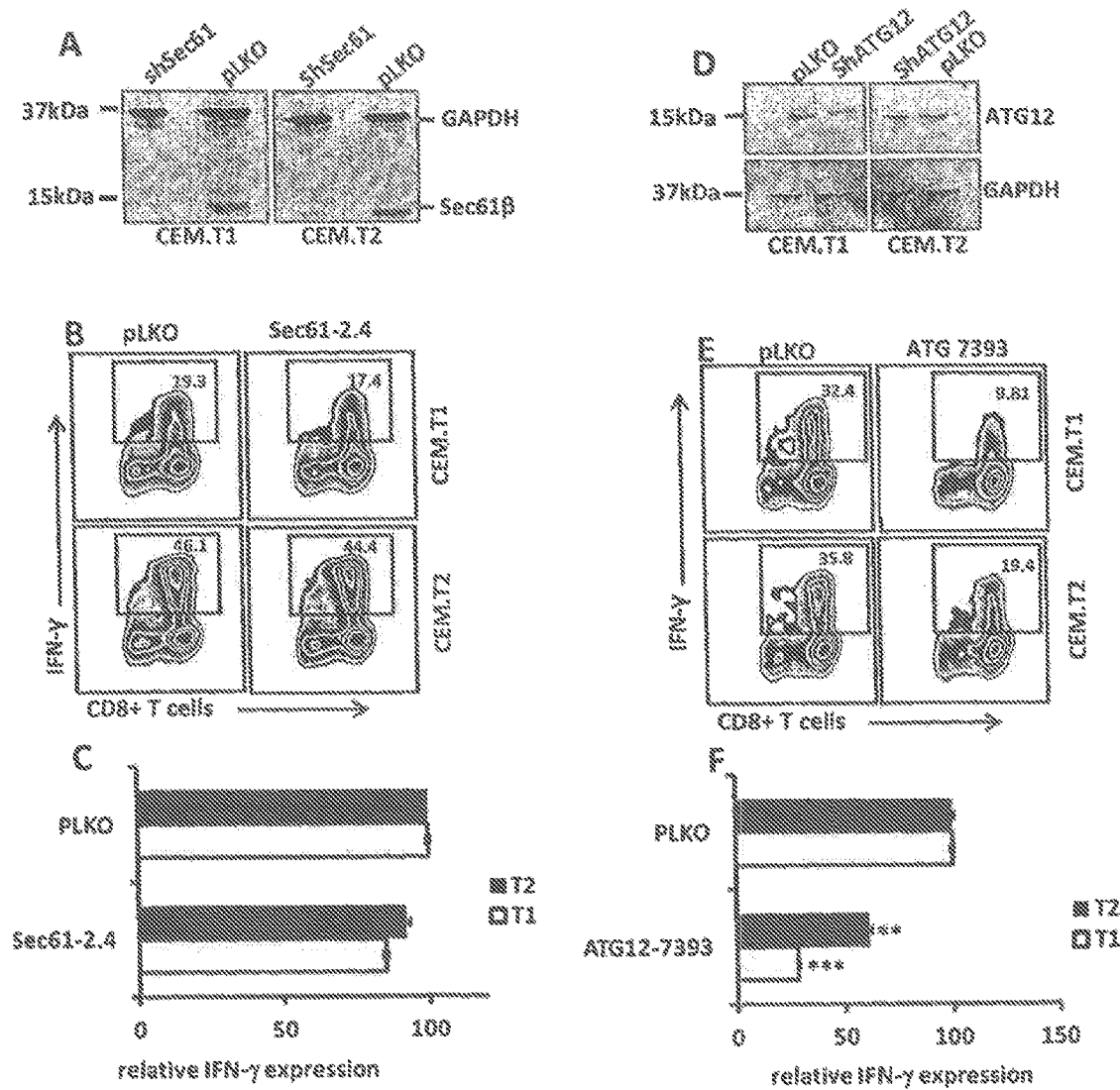
FIG. 11: Effect of Sec61 and ATG12 shRNA on the cross-presentation of the polyepitope protein: CEM T1 and CEM T2 cells were transduced with recombinant lentivirus encoding shRNA for Sec61β subunit or ATG12 or a control vector (pLKO), cultured for two days in R 10 medium, selected in puromycin for seven days and then used as antigen presenting cells. Panel A & D shows western blot analysis of Sec61 and ATG12 protein expression in CEM.T1 and CEM.T2 cells following transduction of shRNA. GAPDH was used as a control for protein loading. Panels B-F shows the expression of IFN-γ by CMV-specific CD8+ T cells following exposure to CMVpoly-PTL sensitized CEM.T1 and CEM.T2 cells transduced with Sec61 and ATG12 shRNA lentivirus or control vector.

To further elucidate the influence of retrotranslocation and autophagy mediated pathways in the cross-presentation of the polyepitope, CEM.T1 and CEM.T2 cells were infected with lentivirus expressing shRNAs for silencing of the Sec61β subunit and ATG12 (autophagy regulator 12) genes. The data presented in FIGS. 11A-C shows that although shRNA expression dramatically reduced the expression of Sec61β subunit, this loss of expression had minimal effect on the presentation of T cell epitopes from the polyepitope protein. In contrast, down-regulation of ATG12 expression in both CEM.T1 and CEM.T2 cells significantly reduced the recognition of CMV polyepitope protein sensitized cells. Taken together these observations demonstrate that cross-presentation of the polyepitope protein occurs through a novel pathway which involves both proteasomal and autophagy pathways.

Example 2

Immunogenicity of CMV Polyepitope Protein in Combination with Adjuvants

Materials and Methods

CMV Polyepitope Vaccine Formulation with MPL and CpG ODN1826

The CMV polyepitope vaccine was formulated by mixing 20 μg of CMVpoly, CMVpoly-PL or CMVpoly-PTL with 25 μg of MPL (TLR4 agonist) and 50 μg of CpG ODN1826 (TLR9 agonist) per dose in a 100 μL volume. TLR agonists were purchased from InvivoGen (San Diego, Calif., USA).

Mouse Immunisations

HHD I mice containing human HLA-A*0201 with a disrupted murine MHC class I were bred and maintained under specific pathogen-free conditions at the QIMR. All protocols were followed in compliance with the QIMR animal ethics committee. In each group at least 5 (M1-5), six-to-eight week old mice, were immunised subcutaneously (s.c.) at the base of the tail with the CMV polyepitope vaccine formulated with the above specified adjuvant combinations. Mice were boosted with an identical vaccine formulation on day 21 and mice were sacrificed on day 35 to determine the polyepitope specific CD8+ T cell responses using intracellular cytokine staining (ICS) assay.

Splenocyte Preparation

Mice were sacrificed by $CO_2$ asphyxiation and spleens were collected in 3 mL of mouse T cell culture medium (DMEM supplemented with 10% FBS, 100 IU/mL penicillin, 200 μg/mL streptomycin sulphate, β-mercaptoethanol, non-essential amino acids and sodium pyruvate). Single cell suspensions were prepared by gently mashing the spleen with a plunger of a syringe. Cells were centrifuged at 1200 rpm for 5 minutes, resuspended in 3 mL of ammonium chloride and Tris buffer (0.017M Tris base in 0.89% ammonium chloride, pH7.4) then incubated for five minutes at room temperature to deplete red blood cells. Cells were centrifuged, washed twice with PBS containing 2% FBS and resuspended in 5 mL of mouse T cell culture medium. To remove excess tissue and cellular debris, the final cell suspension was filtered through a 70 μm cell strainer (Becton Dickinson, San Diego, USA). Cell viability was then determined using the Trypan Blue exclusion method.

In Vitro Stimulation and Expansion of CMV Specific T-Cells from Immunised Mice

Approximately $5 \times 10^6$ splenocytes from vaccinated mice were stimulated with 1 μg of HLA A2 restricted NLV and VLE peptides in 100 μl of mouse T cell culture medium at 37° C., 6.5% $CO_2$ for 2 hours. After incubation, 1 mL of mouse T cell culture medium was added, cells were transferred to 24 well plate and cultured for 10 days at 37° C., 6.5% $CO_2$. On days 3 and 6, cultures were supplemented with 1 mL of T cell culture medium containing 100 U of recombinant IL-2. The T cell specificity of these in vitro expanded cells was assessed using a standard IFN-γ ICS assay. In addition, T cells in these cultures were also assessed for polyfunctional capacity using multi-parameter flow cytometery.

Intracellular Cytokine Staining to Assess IFN-γ Response in Mouse T Cells

Following in vitro stimulation with NLV and VLE approximately $2 \times 10^5$ mouse splenocytes in 50 μL of mouse T cell culture medium were added to the required wells. To stimulate these cells 0.2 μg of NLV and VLE peptides were added and then 150 μL of DMEM containing 0.3 μL of Brefeldin A (BD Pharmingen, San Diego, Calif.) was added to each well and incubated for four hours at 37° C., 10% $CO_2$. Cells were washed twice with PBS containing 2% FCS (wash buffer), surface stained with APC-conjugated anti-CD3, FITC-conjugated anti-CD4 and PerCP-Cy5.5 conjugated anti-CD8 monoclonal antibodies resuspended in wash buffer and incubated at 4° C. for 30 minutes. Cells were washed twice with wash buffer, fixed with 100 μL/well of Cytofix/Cytoperm and washed twice with Perm/Wash buffer. Cells were then intracellularly stained with PE conjugated anti-IFN-γ monoclonal antibody at 4° C. for 30 minutes, cells were washed twice Perm/Wash buffer and acquired on a BD FACSCanto II.

Multi-Parametric Flow Cytometry to Assess the Immune Responses in Vaccinated Mice Following vaccination splenocytes were stimulated ex vivo as mentioned above. Cells were surface stained with FITC conjugated anti-CD4 and PerCP-Cy5.5 conjugated anti-CD8 for 30 mins at 4° C. After washing, fixing and permeabilising, cells were stained intracellularly with PE-conjugated anti-IFN-γ, PE-Cy7 conjugated anti-TNF and APC conjugated anti-IL2 antibodies. Cells were acquired on a BD FACSCanto II and data was analysed using FlowJo software and Boolean gate analysis.

Results

In initial studies, a subunit vaccine formulation based on CMV-encoded glycoprotein B (gB) and polyepitope proteins was tested in combination with human compatible TLR agonists. The polyepitope protein included multiple minimal HLA class I-restricted CD8+ T cell epitopes from different antigens of CMV. This subunit vaccine generated durable anti-viral antibody, Th1 CD4+ and CD8+ T cell responses. The humoral immune response induced by the vaccine displayed strong neutralisation capacity and the antigen-specific T cells expressed multiple cytokines with long-term memory maintenance. Furthermore, this subunit CMV vaccine, through the activation of TLR4 and TLR9, activated different dendritic cell (DC) subsets expressing IL12p70, IFN-α, IL-6 and TNF-α, which play a crucial role in the activation of antigen-specific T cells.

Figure 12:
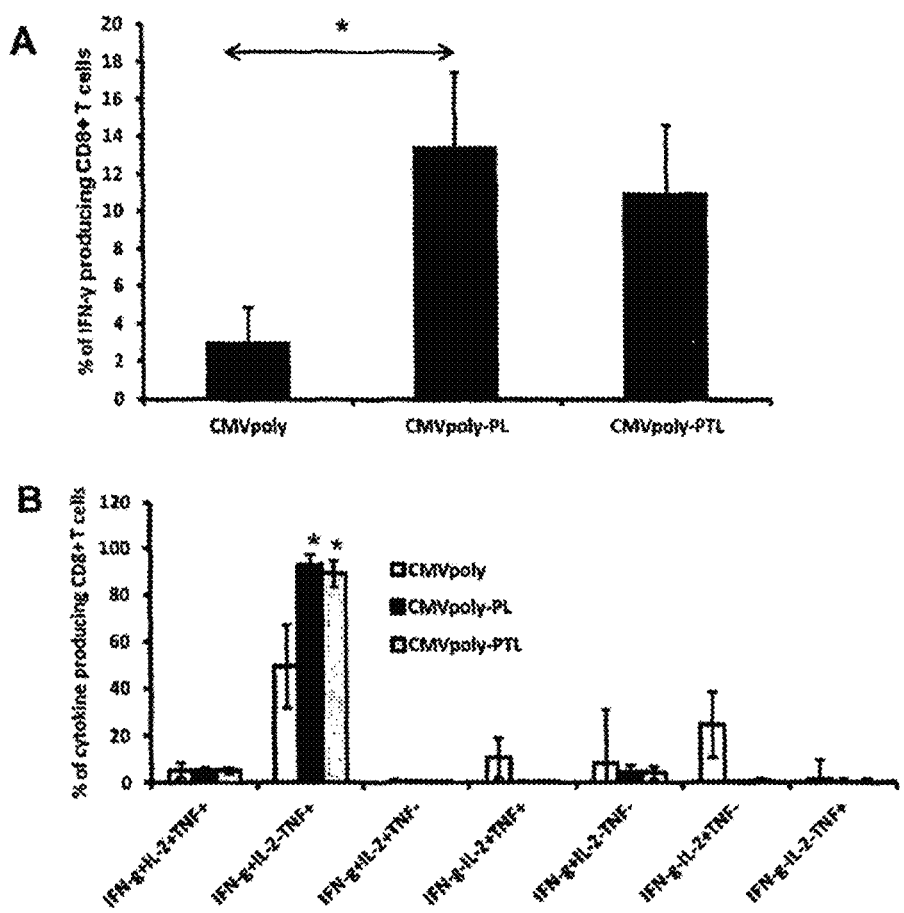
FIG. 12: In vivo assessment of immunogenicity of CMVpoly, CMVpoly-PL and CMVpoly-PTL proteins: To assess the immunogenicity of CMVpoly, CMVpoly-PL or CMVpoly-PTL proteins, 20 μg of protein was formulated with 25 μg of MPL (monophosphoryl lipid A) and 50 μg of CpG ODN1826 in 100 μL volume per dose. On day 0, 6-8 weeks old HLA A2 transgenic mice were immunised subcutaneously and a booster dose was give with an identical formulation on day 21. Mice were sacrificed on day 35, splenocytes were stimulated in vitro with HLA A2-restricted NLV (pp65) and HLA A2-restricted VLE (IE-1) peptide epitopes for 10 days in the presence of IL-2 and then assessed for cytokine expression using ICS assays. Panel A shows the frequencies of CMV-specific CD8+ T cells following immunisation with CMVpoly, CMVpoly-PL or CMVpoly-PTL-based vaccine formulation. Panel B shows the absolute percentage of CMV-specific CD8+ T cells expressing different combination of cytokines (IFN-γ, TNF and/or IL-2) following vaccination with CMVpoly, CMVpoly-PL or CMVpoly-PTL proteins. Error bars represent the mean±SEM. * indicates statistically significant ($p<0.05$).

In Vivo Evaluation of Immunogenicity of CMV Polyepitope Proteins with and without Linkers To determine the immunogenicity of CMVpoly, CMVpoly-PL and CMVpoly-PTL, we next evaluated the immunogenicity of the polyepitope proteins in combination with the TLR4 and TLR9 agonists. HHD-I transgenic mice expressing human HLA A2 MHC Class I allele were immunized with CMVpoly, CMVpoly-PL or CMVpoly-PTL. Following vaccination splenocytes were in vitro stimulated with HLA A2 restricted NLV and VLE peptides. To analyse the establishment CMV polyepitope-specific responses in in vitro stimulated splenocytes, they were assessed for the presence of CMVpoly-specific (HLA A2-restricted epitopes NLV and VLE) CD8$^+$ T cells using an intracellular IFN-γ assay. Interestingly, in line with in vitro data, mice immunised with CMVpoly-PL or CMVpoly-PTL vaccine formulation induced significantly higher frequencies of CMVpoly-epitope-specific CD8$^+$ T cells compared to mice immunised with CMVpoly vaccine formulation (FIG. 12A). In addition there is substantial evidence that the protective efficacy of T cell-based vaccines correlates with the frequencies of multifunctional effectors. Therefore in the subsequent experiments we assessed the functional quality of the CMV-specific CD8$^+$ T cell response. The pattern of IL-2, TNF and IFN-γ production was determined using multiparametric flow cytometry following in vitro expansion of splenocytes from immunised mice. Data presented in the FIG. 12B clearly demonstrate that CD8$^+$ T cells displayed higher polyfunctionality; most importantly higher frequencies of CD8$^+$ T cells were IFN-γ and TNF producers in mice immunized with CMVpoly-PL or CMVpoly-PTL compared to CMVpoly vaccine. Taken together these observations clearly demonstrated that a CMV vaccine formulation based on CMVpoly-PL or CMVpoly-PTL adjuvanted with both TLR4 and TLR9 agonist was most effective in inducing CMV-specific CD8$^+$ T cells with a multifunctional capability.

Discussion

Emerging evidence suggests that CMV-specific CD8$^+$ T cells responses in healthy CMV-seropositive individuals, are directed towards multiple CMV antigens, predominantly pp65 and IE1, but also other structural, early/late antigens and immunomodulators (pp28, pp50, pp150, IE2 gH, gB, US2, US3, US6 and UL18) (Elkington, Walker et al. 2003; Elkington, Shoukry et al. 2004; Manley, Luy et al. 2004; Khan, Bruton et al. 2005; Sylwester, Mitchell et al. 2005). These CD8$^+$ T cell responses play a critical role in immunity to CMV, controlling viral replication and preventing the clinical manifestations of progressive infection in both animal models as well as in humans (Quinnan, Kirmani et al. 1982; Rook, Quinnan et al. 1984; Reddehase, Weiland et al. 1985). These observations indicate that a vaccine against CMV that can induce T cells responses against multiple antigens will likely strengthen protection against CMV-associated disease. Therefore to target multiple antigens, especially to induce CD8$^+$ T cell responses, in this study we have proposed a novel recombinant based polyepitope vaccine technology. Polyepitope based vaccines provide a powerful approach to induce immune responses against a variety of conserved epitopes from a number of antigens without the use of full length antigens which may comprise unknown or pathogenic properties.

A series of CMV polyepitope proteins (13mer, 14mer, 15mer and 20mer) were designed by covalently linking multiple HLA class I restricted T-cell epitopes to potentiate CMV-specific CD8$^+$ T cell responses against a number of antigens in different ethnic populations. Selected epitopes in the CMV polyepitope constructs were derived from highly conserved multiple antigens of CMV, including pp65, pp50, pp150, DNAse, and IE-1 (Brytting, Wahlberg et al. 1992; Retiere, Imbert et al. 1998; Solache, Morgan et al. 1999). To enhance the immunogenicity of the CMV polyepitope, the selected CD8$^+$ T cell epitopes were linked together with a linker sequence consisting of a proteasome liberation amino acid sequence (AD or K or R) and a TAP (transporter associated with antigen processing) recognition motif (RIW, RQW, NIW or NQY) at the carboxyl terminus of each epitope. In this regard, published data shows that the use of the amino acid residues to provide proteasomal processing of the polyepitope proteins (Ishioka, Fikes et al. 1999; Kuttler, Nussbaum et al. 2000; Livingston, Newman et al. 2001) and the motifs for TAP recognition are necessary for transporting the proteasome generated peptides into the endoplasmic reticulum (ER) (Uebel, Wiesmuller et al. 1999; Bazhan, Karpenko et al. 2010). The 13mer, 14mer and 15mer CMV polyepitope proteins were successfully expressed as recombinant proteins in *E. coli* and purified using Ni-NTA chromatography. However, our attempts to make the CMV polyepitope 20mer were unsuccessful due to its highly hydrophobic nature. The optimised protein expression conditions and purification protocol were consistent. Approximately 2 L of shaker flask culture yielded a substantial quantity of polyepitope proteins.

Next we tested the CMV polyepitope proteins immunogenicity in in vitro experiments by stimulating the healthy donor PBMC to augment the frequencies of CMV epitope specific CD8$^+$ T cells. The data from these studies clearly demonstrated that these CMV polyepitope proteins are highly efficient in generating CMV-specific CD8$^+$ T cells responses in virus healthy carriers. Interestingly, our results showed the feasibility of simultaneously amplifying multiple CMV peptide-specific CD8$^+$ T cell responses and these expended CD8$^+$ T cells demonstrated strong expression of IFN-γ, TNF, MIP-1β and CD107a by CMV-specific CD8$^+$ T cells following stimulation with polyepitope protein. These functional characteristics of the T cells are highly important for predicting the efficacy of T cell mediated immune responses and virus clearance [reviewed in (Seder, Darrah et al. 2008)]. In addition to expanding virus-specific CD8$^+$ T cells from healthy donors, we also tested the immunogenicity of the polyepitope protein using human B cells (LCLs) and epithelial cells (HEK293). In this context, the majority of the HLA restricted epitopes encoded by the CMV poly-epitope were processed and presented efficiently to antigen-specific T cells, confirming the propensity of the polyepitope protein to deliver epitopes for presentation via the MHC class I pathway.

Although many studies have shown how exogenous proteins are internalised, processed and presented by MHC class I molecules on antigen presenting cells, exogenously loaded polyepitope protein processing and presentation by antigen presenting cells has never been reported. In general, cross-presentation of exogenous antigens by dendritic cells has been shown to operate using three different pathways. The first proposed model uses an indirect pathway of transferring exogenous antigens from phago-endosomes to the cytosol for proteasome dependent processing. Processed peptides are then loaded in the endoplasmic reticulum by the classical MHC class I machinery (Huang, Bruce et al. 1996). The second model is a direct, proteasome independent pathway whereby antigens are processed and loaded on MHC class I entirely in endosomal compartments (Shen, Sigal et al. 2004).

The third proposed model utilises the delivery of endoplasmic reticulum components to endocytic organelles or the transport of incoming antigen to the endoplasmic reticulum (Guermonprez, Saveanu et al. 2003; Houde, Bertholet et al. 2003). Indeed, in the development of effective vaccines, Immunotherapies against cancers as well as in immune tolerance to self antigens to prevent autoimmunity, cross-presentation of exogenous antigens to naïve CD8+ T cells is the prerequisite for the induction of cytotoxic T cell responses (Rock and Shen 2005). We therefore elucidated the pathway by which CMV polyepitope was processed and cross-presented by CEM.T1 and CEM.T2 cells in the presence of various chemical inhibitors involved in different stages of antigen presentation.

Our results clearly demonstrate that the polyepitope is degraded into peptides in a TAP-independent, proteasome and autophagy-dependent pathway. Both CEM.T1 and CEM.T2 cells treated with proteasome inhibitors and autophagy inhibitors prevented effective presentation of CD8+ T cells epitopes, while presentation was enhanced with lysosome, recycling pathway, cysteine proteases, acid proteases and ER-resident amino peptidases inhibitors. In addition, we also observed reduced presentation of CD8+ T cells epitope by CEM.T1 and CEM.T2 following treatment with brefeldin A and monensin. This effect could be an indirect effect on presentation of CD8+ T cell epitopes because these inhibitors are known to block the transport of newly synthesised MHC I molecules on to the cell surface.

Because processing and presentation of CD8+ T cell epitopes was blocked by proteasome but not ER inhibitors, we hypothesised that CD8+ T cell epitope presentation was mediated via a retrotranslocation pathway whereby exogenously antigens are internalised into phagosomes, then delivered into cytosol through a Sec61 channel and degraded by proteasome into oligopeptides before being transferred to MHC class I molecules in the ER (Ackerman, Giodini et al. 2006; Rock 2006). However, knock down of the Sec61β subunit protein in CEM.T1 and CEM.T2 had no effect on presentation of CD8+ T cells epitopes, indicating that the retrotranslocation pathway may not involve in the processing and presentation of the polyepitope encoded CD8+ T cell epitopes.

Although we found no evidence for the retrotranslocation pathway in the processing of the polyepitope proteins, we did found evidence for a role for the autophagy pathway following knockdown of ATG12. ATG12 is an ubiquitin-like modifier and its covalent conjugation with another autophagy regulator, ATG5, and plays an essential role in autophagy formation and elongation (Mizushima, Noda et al. 1998; Mizushima, Sugita et al. 1998). Therefore, we conclude that CD8+ T cell epitopes from the polyepitope protein are processed and presented by CEM.T1 and CEM.T2 cells through a novel TAP-independent, proteasome and autophagy dependent pathways.

This pathway is difficult to reconcile with the previously proposed cross-presentation models, however, documented evidence suggest that the collaboration between the proteasome and autophagy pathways is essential for protein quality control in the cell (Ding, Ni et al. 2007). In addition, although a proteasome and autophagy dependent pathway has never been reported in the context of cross-presentation it has been show to be involved in the degradation of endogenously over expressed proteins (Webb, Ravikumar et al. 2003).

Thus, based on these observations we speculate that the polyepitope protein is processed and presented through a novel proteasome and autophagy dependent pathway. In summary, polyepitope proteins can be expressed as a recombinant proteins using prokaryotic expression system in a stable form. These polyepitope proteins are highly immunogenic and may have the preferential access to proteasome and autophagosome dependent pathway while cross-presentation by antigen presenting cells.

Example 3

Immunogenicity of EBV Polyepitope Protein in Combination with Adjuvants

Materials and Methods

Construction of EBV Polyepitope Construct

An EBV polyepitope was designed to encode multiple HLA class I restricted T-cell epitopes from 9 different antigens (BMLF1, BRLF1, BZLF1, LMP2, LMP2a, EBNA1, EBNA3A, EBNA3B and EBNA3C). The epitope HLA restriction, amino acid sequences and amino acid locations of these epitopes are shown in Table 3 and illustrated schematically in FIG. 13A.

The polyepitope sequence was designed in such a way that each epitope sequence was preceded by a proteasome liberation amino acid sequence (AD or K or R) and a hexa-histidine tag (SEQ ID NO: 61) was inserted at the c-terminus of each polyepitope protein to allow purification using a nickel-nitrilotriacetic acid (Ni-NTA) column. The amino acid sequence of each construct was translated into DNA sequence based on *E. coli* codon utilisation and inserts were synthetically constructed (DNA2.0, California, USA) and cloned into an expression plasmid (pJexpress 404) under an isopropyl-β-D-thiogalactopyraniside (IPTG) inducible promoter. Synthetically designed EBV polyepitope was transformed into chemically competent *E. coli* DH5a (Invitrogen, Carlsbad, Calif., USA) and plasmids were purified using a QIAGEN maxi prep kit (QIAGEN, Hilden, Germany).

Protein Expression

Chemically competent *E. coli* BL21 (DE3) pLysS (Invitrogen, California, USA) was transformed with the EBV polyepitope expression vector. Transformed cells were plated on Luria Bertani (LB) agar supplemented with 100 µg/mL of ampicillin (LB-Amp) and plates were incubated overnight at 37° C. An isolated colony was picked and inoculated into 10 ml of LB-Amp broth and grown in a shaker at 37° C. and 200 rpm overnight. A small amount of overnight culture was inoculated into 50 mL of LB-Amp broth and grown for 12 hours, then 1% of culture was transferred into 2 L of LB-Amp broth that was then was grown until the O.D. reached 0.6 at 600 nm. EBV polyepitope protein induction was carried out by adding 1 mM/mL of IPTG. These cells were allowed to grow for an additional 4 hours and protein expression levels were determined by analysing un-induced and induced samples on 15% SDS-PAGE.

EBV Polyepitope Protein Purification

At the end of the induction phase, *E. coli* culture was harvested by centrifugation at 10,000 rpm for 15 minutes, the cell pellet was resuspended in 80 mL of lysis buffer (25 mM Tris pH 7.4, 0.5% TritonX100, 150 mM NaCl, 0.5 mg/mL lysozyme) supplemented with a protease inhibitor cocktail (Roche, Mannheim, Germany) and incubated on the ice for 30 minutes. Cell lysis was carried out by sonication on ice for 4×5 minutes cycles with a 10 minute break between each cycle. The lysate was centrifuged at 13,000 rpm for 30 minutes and supernatant and pellet fractions were analysed using SDS-PAGE. Since the majority of the protein was found in the pellet fractions in the form of inclusion bodies (IBs), IBs were washed once with lysis buffer (without lysozyme) under stirring for two hours at RT and solubilised in 150 mL of solubilisation buffer (100 mM $NaH_2PO_4$, 10 mM Tris, 8 M urea, 0.5% TritonX100 pH 8.0) overnight at 4° C. The soluble protein was clarified by centrifugation at 13,000 rpm for 30 minutes and supernatant was used for purification of polyepitope proteins.

Figure 13:
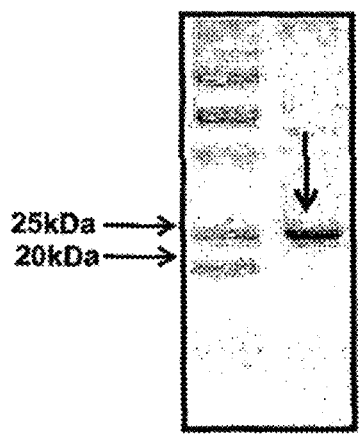
FIG. 13: Schematic design of the Epstein-Barr virus (EBV) polyepitope construct with proteasome linkers and protein purification. Panel A shows the design of EBV polyepitope protein (SEQ ID NO: 77) with proteasome linkers (referred to as EBVpoly). The polyepitope protein comprises a plurality of HLA class I restricted CTL epitopes from Table 3 (SEQ ID NOs: 24, 26-28, 31, 32, and 37-40). Each of the alternate CD8+ T cell epitope sequences are italicised and underlined. For EBVpoly each epitope sequence is separated by amino acid residue(s), which are targets for proteasomal degradation (shown in red). Panel B shows the purification of EBVpoly protein. The DNA sequence encoding the EBVpoly protein was cloned into an IPTG inducible plasmid, pJexpress 404, and transformed into *E. coli* for protein expression. EBVpoly protein was purified using Ni-NTA affinity chromatography and then analysed using SDS-PAGE. Predicted size for the EBVpoly was 25 Kd.

To purify the EBV polyepitope protein we used 5 mL of Ni-NTA (QIAGEN, Hilden, Germany) metal-affinity chromatography matrix. The matrix was washed with 5 column volumes of distilled water followed by equilibration with 3 column volumes of solubilisation buffer. The soluble protein was loaded on the column and the flow rate was adjusted to 1 mL/minute. The unbound protein and impurities were washed-out with 10 column volumes of wash buffer 1 (100 mM $NaH_2PO_4$, 10 mM Tris, 8 M urea pH 6.3) and 20 column volumes of wash buffer 2 (100 mM $NaH_2PO_4$, 10 mM Tris, 8 M urea pH 5.9). The bound protein was eluted with elution buffer (100 mM NaH2PO4, 10 mM Tris, 8 M urea pH 4.3) and the eluted fractions were analysed using SDS-PAGE as shown in FIG. 13B. The positive fractions were pooled together and purified EBV polyepitope protein was dialysed against 25 mM MES buffer at pH 3.5. Following dialysis, the EBV polyepitope protein was concentrated using Ultracel-10K spin columns (Millipore, County Cork, Ireland) followed by sterile filtration using 0.22 µl membrane filter. Final EBV polyepitope protein estimation was carried out using a Bradford assay kit (Bio-Rad, Hercules, Calif., USA).

In Vitro Stimulation and Expansion of EBV Specific T-Cells from Healthy Donors Using Polyepitope Proteins Peripheral blood mononuclear cells (PBMC) from healthy virus carriers were incubated with 25 µg of purified EBV polyepitope protein at 37° C., 6.5% $CO_2$ for 2 hours. After incubation, these PBMC were mixed with un-pulsed PBMC and resuspended in RPMI 1640 medium supplemented with 10% FCS (referred to as growth medium). These cells were cultured in a 24 well plate for 14 days at 37° C., 6.5% $CO_2$. On days 3, 6 and 9 cultures were supplemented with 1 mL of growth medium containing 100 U of recombinant IL-2. The T cell specificity of these in vitro expanded cells was assessed using a standard ICS assay.

Results

Design and Purification of EBV Polyepitope Protein with Proteasome Linkers

Having developed a well established protocol to design, express and purify recombinant polyepitope proteins for immunotherapy against CMV, in the subsequent studies we extended such approaches to design another recombinant polyepitope protein for immunotherapy to combat EBV associated malignancies. In particular, for the treatment of EBV-associated relapsed Hodgkin disease and nasopharyngeal carcinoma EBV-specific CD8+ T cells are considered to be more effective. However, generation of EBV-specific CD8+ T cells is restricted by a number of limitations, such as complex manufacturing process and most often such process requires infectious clinical grade virus material, for instance, recombinant adenovirus vectors for delivering the antigens to antigen-presenting cells. Therefore to overcome such problems, we have designed a novel EBV polyepitope, which can be expressed using a bacterial expression system. An EBV polyepitope encoding 20 minimal CD8+ T cell epitopes from 9 different antigens (BMLF1, LMP2a, BRLF1, LMP2, EBNA3A, BZLF1, EBNA3C, EBNA1 and EBNA3B) was designed as outlined in FIG. 13A and each epitope in the polyepitope sequence was separated by a proteasome linker. A comprehensive list of EBV epitopes included in each of these polyepitope sequences are presented in Table 3. The EBV polyepitope construct was transformed into E. coli. Protein expression conditions was optimised and expressed protein was purified using Ni-NTA matrix. In line with CMV polyepitope proteins results, data obtained from these experiments showed that EBV polyepitope can be successfully expressed using a bacterial expression system and protein can be purified to homogeneity (FIG. 13B).

In Vitro Evaluation of Immunogenicity of CMVpolyepitope Proteins with and without Linkers To determine the potential efficacy of EBV polyepitope to expand the EBV-specific CD8+ T cells, PBMC from a number of different donors were stimulated with purified recombinant EBV polyepitope protein. Following stimulation expanded EBV-specific CD8+ T cells were assessed using intracellular cytokine assay. Data presented in FIG. 14 shows that a considerable proportion of donors showed expansion of EBV-specific CD8+ T cells following stimulation with EBV polyepitope compared to unstimulated PBMC. Interestingly, the cells from each donor recognised multiple epitopes restricted through a number of HLA class I alleles and the majority of the donors had higher frequencies of expanded CD8+ T cells towards at least 3 different epitopes.

REFERENCES

Ackerman, A. L., A. Giodini, et al. (2006). "A role for the endoplasmic reticulum protein retrotranslocation machinery during crosspresentation by dendritic cells" *Immunity* 25(4): 607-617.

Anderson, R. J. and J. Schneider (2007). "Plasmid DNA and viral vector-based vaccines for the treatment of cancer." *Vaccine* 25 Suppl 2: B24-34.

Arvin, A. M., P. Fast, et al. (2004). "Vaccine development to prevent cytomegalovirus disease: report from the National Vaccine Advisory Committee." *Clin Infect Dis* 39(2): 233-239.

Ausubel, F. M., Brent, R., kingston, R. E., Moore, D. D., Seidman, J. G., Smith, J. G., Smith, J. A., and Struhl, k. (1995). *Current Protocols in Molecular Biology.* New York: Wiley-Interscience Bazhan, S. I., L. I. Karpenko, et al. (2010). "Rational design based synthetic polyepitope DNA vaccine for eliciting HIV-specific CD8+ T cell responses." *Mol Immunol* 47(7-8): 1507-1515.

Bernstein, D. I., E. A. Reap, et al. (2009). "Randomized, double-blind, Phase 1 trial of an alphavirus replicon vaccine for cytomegalovirus in CMV seronegative adult volunteers." *Vaccine* 28(2): 484-493.

Betts, M. R., C. M. Gray, et al. (2006). "Antigen-specific T-cell-mediated immunity after HIV-1 infection: implications for vaccine control of HIV development." *Expert Rev Vaccines* 5(4): 505-516.

Brytting, M., J. Wahlberg, et al. (1992). "Variations in the cytomegalovirus major immediate-early gene found by direct genomic sequencing." *J Clin Microbiol* 30(4): 955-960.

Darrah, P. A., D. T. Patel, et al. (2007). "Multifunctional TH1 cells define a correlate of vaccine-mediated protection against *Leishmania major*." *Nat Med* 13(7): 843-850.

Dasari, V., C. Smith, et al. (2011). "Recombinant glycoprotein B vaccine formulation with Toll-like receptor 9 agonist and immune-stimulating complex induces specific immunity against multiple strains of cytomegalovirus." *J Gen Virol* 92(Pt 5): 1021-1031.

Ding, W. X., H. M. Ni, et al. (2007). "Linking of autophagy to ubiquitin-proteasome system is important for the regulation of endoplasmic reticulum stress and cell viability." *Am J Pathol* 171(2): 513-524.

Drulak, M. W., F. J. Malinoski, et al. (2000). "Vaccination of seropositive subjects with CHIRON CMV gB subunit vaccine combined with MF59 adjuvant for production of CMV immune globulin." *Viral Immunol* 13(1): 49-56.

Elkington, R., N. H. Shoukry, et al. (2004). "Cross-reactive recognition of human and primate cytomegalovirus sequences by human CD4 cytotoxic T lymphocytes specific for glycoprotein B and H." *Eur J Immunol* 34(11): 3216-3226.

Elkington, R., S. Walker, et al. (2003). "Ex vivo profiling of CD8+-T-cell responses to human cytomegalovirus reveals broad and multispecific reactivities in healthy virus carriers." *J Virol* 77(9): 5226-5240.

Frankenberg, N., S. Pepperl-Klindworth, et al. (2002). "Identification of a conserved HLA-A2-restricted decapeptide from the IE1 protein (pUL123) of human cytomegalovirus." *Virology* 295(2): 208-216.

Guermonprez, P., L. Saveanu, et al. (2003). "ER-phagosome fusion defines an MHC class I cross-presentation compartment in dendritic cells." *Nature* 425(6956): 397-402.

Houde, M., S. Bertholet, et al. (2003). "Phagosomes are competent organelles for antigen cross-presentation." *Nature* 425(6956): 402-406.

Huang, A. Y., A. T. Bruce, et al. (1996). "In vivo cross-priming of MHC class I-restricted antigens requires the TAP transporter." *Immunity* 4(4): 349-355.

Ishioka, G. Y., J. Fikes, et al. (1999). "Utilization of MHC class I transgenic mice for development of minigene DNA vaccines encoding multiple HLA-restricted CTL epitopes." *J Immunol* 162(7): 3915-3925.

Jacobson, M. A., E. Sinclair, et al. (2006). "Antigen-specific T cell responses induced by Towne cytomegalovirus (CMV) vaccine in CMV-seronegative vaccine recipients." *J Clin Virol* 35(3): 332-337.

Khan, N., R. Bruton, et al. (2005). "Identification of cytomegalovirus-specific cytotoxic T lymphocytes in vitro is greatly enhanced by the use of recombinant virus lacking the US2 to US11 region or modified vaccinia virus Ankara expressing individual viral genes." *J Virol* 79(5): 2869-2879.

Kuttler, C., A. K. Nussbaum, et al. (2000). "An algorithm for the prediction of proteasomal cleavages." *J Mol Biol* 298(3): 417-429.

Liu, M. A. "Immunologic basis of vaccine vectors." *Immunity* 33(4): 504-515.

Livingston, B. D., M. Newman, et al. (2001). "Optimization of epitope processing enhances immunogenicity of multiepitope DNA vaccines." *Vaccine* 19(32): 4652-4660.

Manley, T. J., L. Luy, et al. (2004) "Immune evasion proteins of human cytomegalovirus do not prevent a diverse CD8+ cytotoxic T-cell response in natural infection." *Blood* 104(4): 1075-1082.

Millington, K. A., J. A. Innes, et al. (2007). "Dynamic relationship between IFN-gamma and IL-2 profile of *Mycobacterium tuberculosis*-specific T cells and antigen load." *J Immunol* 178(8): 5217-5226.

Mizushima, N., T. Noda, et al. (1998). "A protein conjugation system essential for autophagy." *Nature* 395(6700): 395-398.

Mizushima, N., H. Sugita, et al. (1998). "A new protein conjugation system in human. The counterpart of the yeast Apg12p conjugation system essential for autophagy." *J Biol Chem* 273(51): 33889-33892.

Mutter, W., M. J. Reddehase, et al. (1988). "Failure in generating hemopoietic stem cells is the primary cause of death from cytomegalovirus disease in the immunocompromised host." *J Exp Med* 167(5): 1645-1658.

Nebbia, G., F. M. Mattes, et al. (2008). "Polyfunctional cytomegalovirus-specific CD4+ and pp65 CD8+ T cells protect against high-level replication after liver transplantation." *Am J Transplant* 8(12): 2590-2599.

Palella, F. J., Jr., K. M. Delaney, et al. (1998). "Declining morbidity and mortality among patients with advanced human immunodeficiency virus infection. HIV Outpatient Study Investigators." *N Engl J Med* 338(13): 853-860.

Quinnan, G. V., Jr., N. Kirmani, et al. (1982). "Cytotoxic t cells in cytomegalovirus infection: HLA-restricted T-lymphocyte and non-T-lymphocyte cytotoxic responses correlate with recovery from cytomegalovirus infection in bone-marrow-transplant recipients." *N Engl J Med* 307 (1): 7-13.

Reddehase, M. J., F. Weiland, et al. (1985). "Interstitial murine cytomegalovirus pneumonia after irradiation: characterization of cells that limit viral replication during established infection of the lungs." *J Virol* 55(2): 264-273.

Retiere, C., B. M. Imbert, et al. (1998). "A polymorphism in the major immediate-early gene delineates groups among cytomegalovirus clinical isolates." *Virus Res* 57(1): 43-51.

Riddell, S. R., K. S. Watanabe, et al. (1992). "Restoration of viral immunity in immunodeficient humans by the adoptive transfer of T cell clones." *Science* 257(5067): 238-241.

Rock, K. L. (2006). "Exiting the outside world for cross-presentation." *Immunity* 25(4): 523-525.

Rock, K. L. and L. Shen (2005). "Cross-presentation: underlying mechanisms and role in immune surveillance." *Immunol Rev* 207: 166-183.

Rook, A. H., G. V. Quinnan, Jr., et al. (1984). "Importance of cytotoxic lymphocytes during cytomegalovirus infection in renal transplant recipients." *Am J Med* 76(3): 385-392.

Salmon-Ceron, D., M. C. Mazeron, et al. (2000). "Plasma cytomegalovirus DNA, pp65 antigenaemia and a low CD4 cell count remain risk factors for cytomegalovirus disease in patients receiving highly active antiretroviral therapy." *AIDS* 14(8): 1041-1049.

Seder, R. A., P. A. Darrah, et al. (2008). "T-cell quality in memory and protection: implications for vaccine design." *Nat Rev Immunol* 8(4): 247-258.

Shen, L., L. J. Sigal, et al. (2004). "Important role of cathepsin S in generating peptides for TAP-independent MHC class I crosspresentation in vivo." *Immunity* 21(2): 155-165.

Soderberg-Naucler, C. (2006). "Does cytomegalovirus play a causative role in the development of various inflammatory diseases and cancer?" *J Intern Med* 259(3): 219-246.

Solache, A., C. L. Morgan, et al. (1999). "Identification of three HLA-A*0201-restricted cytotoxic T cell epitopes in the cytomegalovirus protein pp65 that are conserved between eight strains of the virus." *J Immunol* 163(10): 5512-5518.

Sylwester, A. W., B. L. Mitchell, et al. (2005). "Broadly targeted human cytomegalovirus-specific CD4+ and CD8+ T cells dominate the memory compartments of exposed subjects." *J Exp Med* 202(5): 673-685.

Uebel, S., K. H. Wiesmuller, et al. (1999). "Peptide libraries in cellular immune recognition." *Curr Top Microbiol Immunol* 243: 1-21.

Walter, E. A., P. D. Greenberg, et al. (1995). "Reconstitution of cellular immunity against cytomegalovirus in recipients of allogeneic bone marrow by transfer of T-cell clones from the donor." *N Engl J Med* 333(16): 1038-1044.

Webb, J. L., B. Ravikumar, et al. (2003). "Alpha-Synuclein is degraded by both autophagy and the proteasome." *J Biol Chem* 278(27): 25009-25013.

Wloch, M. K., L. R. Smith, et al. (2008). "Safety and immunogenicity of a bivalent cytomegalovirus DNA vaccine in healthy adult subjects." *J Infect Dis* 197(12): 1634-1642.

Zhong, J. and R. Khanna (2009). "Ad-gBCMVpoly: A novel chimeric vaccine strategy for human cytomegalovirus-associated diseases." *J Clin Virol.*

Zhong, J., M. Rist, et al. (2008). "Induction of pluripotent protective immunity following immunisation with a chimeric vaccine against human cytomegalovirus." *PLoS ONE* 3(9): e3256.

TABLE 1

List of HLA class-1 restricted Epitopes included in the CMV polyepitope 13, 14, 15 & 20mer

| HLA restriction | CMV antigen | SEQ ID NO | Sequence | Location | Code | 13mer | 14mer | 15mer | 20mer |
|---|---|---|---|---|---|---|---|---|---|
| HLA A1 | pp50 | 11 | VTEHDTLLY | 245-253 | VTE | + | + | + | + |
| HLA A2 | pp65 | 12 | NLVPMVATV | 495-503 | NLV | + | + | + | + |
|  | IE-1 | 13 | VLEETSVML | 316-324 | VLE | + | + | + | + |
| HLA A3 | IE-1 | 8 | KLGGALQAK | 184-192 | KLG | + |  |  | + |
|  | pp150 | 14 | TTVYPPSSTAK | 945-955 | TTV |  | + | + |  |
| HLA 11 | pp65 | 2 | GPISHGHVLK | 16-24 | GPI | + | + | + | + |
| HLA A23/24 | pp65 | 15 | AYAQKIFKIL | 248-257 | AYA |  | + | + | + |
| HLA A24 | pp65 | 3 | QYDPVAALF | 341-349 | QYD | + | + | + | + |
| HLA B7 | pp65 | 5 | TPRVTGGGAM | 417-426 | TPR | + | + | + | + |
|  | pp65 | 9 | RPHERNGFTVL | 265-275 | RPH | + | + | + | + |
| HLA B8 | IE-1 | 6 | QIKVRVDMV | 88-96 | QIK | + | + | + | + |
|  | IE-1 | 10 | ELRRKMMYM | 199-207 | ELR | + | + | + | + |
| HLA B27 | DNAse | 16 | ARVYEIKCR | 274-282 | ARV |  |  |  | + |
| HLA B35 | pp65 | 1 | FPTKDVAL | 188-195 | FPT | + | + | + | + |
|  | pp65 | 7 | IPSINVHHY | 123-131 | IPS | + | + | + | + |
|  | pp65 | 17 | CPSQEPMSIYVY | 103-114 | CPS |  |  |  | + |
| HLA B40/60 | pp65 | 18 | CEDVPSGKL | 232-240 | CED |  |  |  | + |
| HLA B41 | gB | 19 | YAYIYTTYL | 153-161 | YAY |  |  |  | + |
| HLA B44 | pp65 | 4 | QEFFWDANDIY | 511-521 | QEFF | + | + | + | + |
| HLA B57 | pp65 | 20 | QAIRETVEL | 331-339 | QAI |  |  |  | + |
| HLA cw6 | pp65 | 21 | TRATKMQVI | 211-219 | TRA |  |  | + | + |

TABLE 2

| SEQ ID No. | *CTL epitope sequence | HLA restriction | Antigen |
|---|---|---|---|
| 1 | FPTKDVALADRIW | B35 | pp65 |
| 2 | GPISGHVLKADNQY | A11 | pp65 |
| 3 | QYDPVAALFADRQW | A24 | pp65 |
| 4 | QEFFWDANDIYADRIW | B44/DRw52 | pp65 |
| 5 | TPRVTGGGAMRNIW | B7 | pp65 |
| 6 | QIKVRVDMVRNQY | B8 | IE-1 |
| 7 | IPSINVHHYRNQY | B35 | pp65 |
| 8 | KLGGALQAKADRIW | A3 | pp65 |
| 9 | RPHERNGFTVRNIW | B7 | pp65 |
| 10 | ELRRKMMYMADNIW | B8 | IE-1 |
| 11 | VTEHDTLLYKRQW | A1 | pp50 |
| 12 | NLVPMVATVKRQW | A2 | pp65 |
| 13 | VLEETSVMLKNIW | A2 | IE-1 |

*CTL epitope sequence is in bold, TAP sequence is in italics and proteasome Processing sequence is underlined. SEQ ID NOS refer to bolded epitope sequence. Full-length sequences disclosed as SEQ ID NOS 62-74, respectively, in order of appearance.

TABLE 3

List of HLA class-1 restricted Epitopes included in the EBV polyepitope 20mer

| HLA Restriction | EBV antigens | SEQ ID no | Sequence | Amino acid location | Abbreviated code |
|---|---|---|---|---|---|
| HLA A2 | BMLF1 | 22 | GLCTLVAML | 280-288 | GLC |
|  | LMP2a | 23 | CLGGLLTMV | 426-434 | CLG |
| HLA A3 | BRLF1 | 24 | RVRAYTYSK | 148-156 | RVR |
| HLA A11 | BRLF1 | 25 | ATIGTAMYK | 134-142 | ATI |
|  | LMP2a | 26 | SSCSSCPLSKI | 340-350 | SSC |
| HLA A23 | LMP2 | 27 | PYLFWLAAI | 131-139 | PYL |
| HLA A24 | LMP2a | 28 | TYGPVFMCL | 419-427 | TYG |
| HLA A30 | EBNA3A | 29 | AYSSWMYSY | 176-184 | AYS |
| HLA B7 | EBNA 3A | 30 | RPPIFIRRL | 379-387 | RPP |
| HLA B8 | EBNA3A | 31 | FLRGRAYGL | 325-333 | FLR |
|  | BZLF1 | 32 | RAKFKQLL | 190-197 | RAK |
| HLA B15 | EBNA3C | 33 | QNGALAINTF | 213-222 | QNG |
| HLA B27 | EBNA3C | 34 | RRIYDLIEL | 258-266 | RRI |
| HLA B35/B*5301 | EBNA1 | 35 | HPVGEADYFEY | 407-417 | HPV |
|  | BZLF1 | 36 | LPEPLPQGQLTAY | 52-64 | LPE |
| HLA B40 | LMP2a | 37 | IEDPPFNSL | 200-208 | IED |
| HLA B44 | EBNA3C | 38 | EENLLDFVRFMGV | 281-293 | EEN |
|  | EBNA3B | 39 | VEITPYKPTW | 657-666 | VEI |
|  | BZLF1 | 40 | EECDSELEIKRY | 169-180 | EEC |
| HLA B57/B58 | EBNA3B | 41 | VSFIEFVGW | 279-287 | VSF |

Throughout the specification the aim has been to describe the preferred embodiments of the invention without limiting the invention to any one embodiment or specific collection of features. It will therefore be appreciated by those of skill in the art that, in light of the instant disclosure, various modifications and changes can be made in the particular embodiments exemplified without departing from the scope of the present invention.

All computer programs, algorithms, patent and scientific literature referred to herein is incorporated herein by reference in their entirety.

The invention claimed is:

1. A protein comprising amino acid sequence selected from the amino acid sequences set forth in SEQ ID NOS: 42-46 and SEQ ID NO: 48, wherein the protein comprises a plurality epitopes.

2. The protein of claim 1, wherein the protein further comprises at least one CMV CTL epitope derived from pp50, pp65, and pp 150 and/or IE-1.

3. The protein of claim 2, wherein the at least one CTL epitope has an amino acid sequence selected from the amino acid sequences set forth in SEQ ID NOS: 1-21.

4. The isolated protein of claim 3, wherein the at least one CTL epitope has an amino acid sequence selected from the amino acid sequences set forth in SEQ ID NOS: 1-13.

5. The protein of claim 3, wherein the at least one CTL epitope has an amino acid sequence set forth in SEQ ID NO:11.

6. The protein of claim 1, wherein the protein further CTL epitopes comprises at least one EBV CTL epitope derived from one or more antigens selected from the group consisting of: BMLF1, LMP2a, BRLF1, LMP2, EBNA3A, BZLF1, EBNA3C, EBNA1 and EBNA3B.

7. The protein of claim 6, wherein the at least one CTL epitope has an amino acid sequence selected from the amino acid sequences set forth in SEQ ID NOS: 22-41.

8. The protein of claim 1, wherein the protein further comprises an amino acid sequence set forth in SEQ ID NO:49.

9. A nucleic acid encoding the protein of claim 1.

10. A genetic construct comprising the nucleic acid of claim 9 operably linked to one or more regulatory sequences in an expression vector.

11. A pharmaceutical composition comprising one or more of the proteins of claim 1, and a pharmaceutically-acceptable carrier, diluent or excipient.

12. The pharmaceutical composition of claim 11, further comprising an immunostimulatory molecule or adjuvant.

13. The pharmaceutical composition of claim 12, wherein the immunostimulatory molecule or adjuvant is one or more TLR agonists that include a TLR4 agonist and/or a TLR9 agonist.

14. The pharmaceutical composition of claim 11, which is a vaccine for eliciting a protective immune response against a herpesvirus in a human.

15. The pharmaceutical composition of claim 12, which is a vaccine for eliciting a cytotoxic T-lymphocyte (CTL) immune response in an animal.

16. The protein of claim 1, further comprising a Transporter Associated with Antigen Processing (TAP) recognition motif.

17. The protein of claim 1, wherein the protein comprises the amino acid sequence set forth in SEQ ID NO: 42.

18. The protein of claim 1, wherein the protein comprises the amino acid sequence set forth in SEQ ID NO: 43.

19. The protein of claim 1, wherein the protein comprises the amino acid sequence set forth in SEQ ID NO: 44.

20. The protein of claim 1, wherein the protein comprises the amino acid sequence set forth in SEQ ID NO: 45.

21. The protein of claim 1, wherein the protein comprises the amino acid sequence set forth in SEQ ID NO: 46.

22. The protein of claim 1, wherein the protein comprises the amino acid sequence set forth in SEQ ID NO: 48.

* * * * *

UNITED STATES PATENT AND TRADEMARK OFFICE
CERTIFICATE OF CORRECTION

PATENT NO. : 9,901,632 B2
APPLICATION NO. : 14/436239
DATED : February 27, 2018
INVENTOR(S) : Rajiv Khanna et al.

It is certified that error appears in the above-identified patent and that said Letters Patent is hereby corrected as shown below:

In the Specification

Column 1, Line numbers 9-11, please delete:
", which applications are herein incorporated by reference in their entireties and to which priority is claimed".

Signed and Sealed this
Eighth Day of May, 2018

Andrei Iancu
*Director of the United States Patent and Trademark Office*